United States Patent
Frey

(10) Patent No.: US 9,679,115 B2
(45) Date of Patent: Jun. 13, 2017

(54) METHODS AND DEVICES FOR REDUCING TRANSFUSIONS DURING OR AFTER SURGERY AND FOR IMPROVING QUALITY OF LIFE AND FUNCTION IN CHRONIC DISEASE

(76) Inventor: Kathrine P. Frey, Edina, MN (US)

( * ) Notice: Subject to any disclaimer, the term of this patent is extended or adjusted under 35 U.S.C. 154(b) by 889 days.

(21) Appl. No.: 13/576,874

(22) PCT Filed: Feb. 2, 2011

(86) PCT No.: PCT/US2011/023498
§ 371 (c)(1),
(2), (4) Date: Oct. 24, 2012

(87) PCT Pub. No.: WO2011/097313
PCT Pub. Date: Aug. 11, 2011

(65) Prior Publication Data
US 2013/0035951 A1 Feb. 7, 2013

Related U.S. Application Data

(60) Provisional application No. 61/300,684, filed on Feb. 2, 2010.

(51) Int. Cl.
*G06Q 50/22* (2012.01)
*G06Q 50/24* (2012.01)
*G06F 19/00* (2011.01)

(52) U.S. Cl.
CPC ...... *G06F 19/3481* (2013.01); *G06F 19/3431* (2013.01)

(58) Field of Classification Search
CPC . G06F 19/3481; G06F 19/3431; G06Q 50/22; G06Q 50/23
(Continued)

(56) References Cited

U.S. PATENT DOCUMENTS 6,304,767 B1* 10/2001 Soller ............... A61B 5/14535
356/39
7,430,478 B2* 9/2008 Fletcher-Haynes . A61M 1/3693
600/300
(Continued)

FOREIGN PATENT DOCUMENTS

WO WO-2006/113987 A1 11/2006

OTHER PUBLICATIONS

McCluskey et al., "Derivation of a risk index for the prediction of massive blood transfusion in liver transplantation," Liver Transpl. 12(11):1584-93 (2006).
(Continued)

*Primary Examiner* — Eliza Lam
(74) *Attorney, Agent, or Firm* — Clark & Elbing LLP; Kristina Bieker-Brady

(57) ABSTRACT

The present Invention relates to methods of treating subjects preparing to undergo surgery or methods of treating chronic disease and methods for reducing transfusions and a computer readable storage medium and a physical computing device for carrying out these methods which include: a) receiving a profile of said subject, in a physical computing device, including a level of hemoglobin of said subject, level of creatinine of said subject, and information regarding current or past history of disease; b) applying said level of hemoglobin and said level of creatinine, in said physical computing device, to determine level of transfusion risk; c) applying said information regarding current or past history of disease of said subject, in said physical computing device, to determine level of comorbidity; d) applying said level of hemoglobin, said level of transfusion risk, and said level of comorbidity, in said physical computing device, to determine a patient care plan.

91 Claims, 38 Drawing Sheets

(58) Field of Classification Search
USPC .......................................................... 705/2–3
See application file for complete search history.

(56) References Cited

U.S. PATENT DOCUMENTS

| | | | |
|---|---|---|---|
| 7,650,291 | B2 | 1/2010 | Rosenfeld et al. |
| 2003/0154109 | A1* | 8/2003 | Martin ................... G06Q 50/24 705/3 |
| 2007/0214013 | A1 | 9/2007 | Silverman |
| 2009/0130702 | A1 | 5/2009 | Goldstein |
| 2009/0281839 | A1* | 11/2009 | Lynn ..................... G06F 19/321 705/3 |
| 2012/0016685 | A1 | 1/2012 | Ryan et al. |
| 2012/0016686 | A1 | 1/2012 | Ryan et al. |

OTHER PUBLICATIONS

Supplementary European Search Report for European Patent Application 11740310.5, mailed Jul. 21, 2015 (10 pages).
Dilla et al., "The effect of automated alerts on preoperative anemia management," Hematology. 20(3):160-4 (2015) (6 pages).
Guinn et al., "How do we develop and implement a preoperative anemia clinic designed to improve perioperative outcomes and reduce cost?" Transfusion. 56(2):297-303 (2016).
Muñoz et al., "'Fit to fly': overcoming barriers to preoperative haemoglobin optimization in surgical patients," Br J Anaesth. 115(1):15-24 (2015) (11 pages).
Office Action for European Patent Application No. 11740310.5, dated Nov. 24, 2016 (9 pages).
Office Action for Canadian Patent Application No. 2,788,650, dated Jan. 30, 2017 (4 pages).
Alghamdi et al., "Development and Validation of Transfusion Risk Understanding Scoring Tool (TRUST) to Stratify Cardiac Surgery Patients According to their Blood Transfusion Needs," Transfusion 46:1120-1129 (2006).
Anker et al., "Ferric Carboxymaltose in Patients with Heart Failure and Iron Deficiency," N. Engl. J. Med. 361: 2436-2448 (2009).
Bernard et al., "Intraoperative Transfusion of 1 U to 2 U Packed Red Blood Cells is Associated with Increased 30-Day Mortality; Surgical-Site Infection, Pneumonia, and Sepsis in General Surgery Patients," J. Am. Coll. Surg. 208: 931-937 (2009).
Bisbe et al., "Prevalence of Preoperative Anemia and Hematinic Deficiencies in Patients Scheduled for Elective Major Orthopedic Surgery," Transfusion Alternatives in Transfusion Medicine 10: 166-173 (2008).
Brevig et al., "Blood Transfusion Reduction in Cardiac Surgery: Multidisciplinary Approach at a Community Hospital," Ann. Thorac. Surg. 87: 532-539 (2009).
Despotis et al., "Monitoring of Hemostasis in Cardiac Surgical Patients: Impact of Point-of-Care Testing on Blood Loss and Transfusion Outcomes," Clin. Chem. 43: 1684-1696 (1997).
Deyo et al., "Adapting a Clinical Comorbidity Index for Use with ICD-9-CM Administrative Databases," J. Clin. Epidemiol. 45: 613-619 (1992).
Ereth et al., "Does the Platelet-Activated Clotting Test (HemoSTATUS®) Predict Blood Loss and Platelet Dysfunction Associated with Cardiopulmonary Bypass?," Anesth. Analg. 85: 259-264 (1997).
Gombotz et al., "Blood Use in Elective Surgery: The Austrian Benchmark Study," Transfusion 47: 1468-1480 (2007).

Goodnough and Shander, "Blood Management," Arch. Pathol. Lab. Med. 131:695-701 (2007).
Goodnough et al., "Detection, Evaluation, and Management of Anemia in the Elective Surgical Patient," Anesth. Analg. 101:1858-1861 (2005).
Gross, "Estimating Allowable Blood Loss: Corrected for Dilution," Anesthesiology 58: 277-280 (1983).
Gruson et al., "The Relationship Between Admission Hemoglobin Level and Outcome After Hip Fracture," J. Orthop. Trauma 16: 39-44 (2002).
Hall et al., "National Hospital Discharge Survey: 2007 Summary," National Health Statistics Reports No. 29 (2010) (21 pages).
Joehl, Preoperative Evaluation: Pulmonary, Cardiac, Renal Dysfunction and Comorbidities, Surg. Clin. North. Am. 85: 1061-1073 (2005).
Karkouti et al., "Risk Associated with Preoperative Anemia in Cardiac Surgery: A Multicenter Cohort Study," Circulation 117: 478-484 (2008).
Keeler et al., "Changes in Sickness at Admission Following the Introduction of the Prospective Payment System," JAMA 264: 1962-1968 (1990).
Lenoir et al., "Individual Probability of Allogenic Erythrocyte Transfusion in Elective Spine Surgery," Anesthesiology 110:1050-1060 (2009).
Levit et al., "HCUP Facts and Figures: Statistics on Hospital-Based Care in the United States," (Rockville, MD: Agency for Healthcare Research and Quality, 2009) (90 pages).
Paxton, "Easy Does It-Showing Caution with RBC Transfusions," CAP Today (2009) (4 pages).
Phend, "Group Questions Appropriateness of Most Blood Transfusions," MedPage Today (2009) (3 pages).
Shander et al., "Estimating the Cost of Blood: Past, Present, and Future Directions," Best Prac. Res. Clin. Anaesthesiol. 21: 271-289 (2007).
Shander, "Financial and Clinical Oucomes Associated with Surgical Bleeding Complications," Surgery 142 (4 Suppl.): S20-S25 (2007).
Shander et al., "Timing and Incidence of Postoperative Infections Associated with Blood Transfusion: Analysis of 1,489 Orthopedic and Cardiac Surgery Patients," Surg. Infect. 10: 277-283 (2009).
Shander et al., "The True Cost of Red Blood Cell Transfusion in Surgical Patients," 50th ASH Annual Meeting and Exposition, http://ash.confex.com/ash/2008/webprogram/Paper11923.html, accessed Jan. 5, 2010 (2008). (Abstract, 2 pages).
Stubbs, "Allogeneic Blood Transfusions Why Do We Even Care?," Division of Transfusion Medicine, Dept. of Laboratory Medicine & Pathology, Mayo Clinic, Rochester, Minnesota (2009) (12 pages).
The United States Department of Health and Human Services, The 2007 National Blood Collection and Utilization Survey Report, accessible on http://www.hhs.gov/ash/bloodsafety/nbcus/index.html (66 pages).
Wang, "What's the Shelf Life of Blood?: Focus on Whether Older Donations Impair Recovery of Transfusion Recipients," The Wall Street Journal, http://online.wsj.com/article/SB10001424052748703939404574567771, accessed Jan. 5, 2010 (2009) (3 pages).
Wong et al., "A Cluster-Randomized Controlled Trial of a Blood Conservation Algorithm in Patients Undergoing Total Hip Joint Arthroplasty," Transfusion 47:832-841 (2007).
International Search Report and Written Opinion of the International Searching Authority for International Application No. PCT/US2011/023498, dated Mar. 30, 2011 (20 pages).

* cited by examiner

METHODS AND DEVICES FOR REDUCING TRANSFUSIONS DURING OR AFTER SURGERY AND FOR IMPROVING QUALITY OF LIFE AND FUNCTION IN CHRONIC DISEASE

CROSS REFERENCE TO RELATED APPLICATIONS

This application claims priority under 35 U.S.C. §371 of International Application No. PCT/US2011/023498, filed Feb. 2, 2011, which claims benefit of U.S. Provisional Application No. 61/300,684, filed on Feb. 2, 2010, each of which is hereby incorporated by reference in its entirety.

FIELD OF THE INVENTION

The present invention relates to methods for establishing a diagnosis of blood health and for developing related treatment plans.

BACKGROUND OF THE INVENTION

Overuse of blood components in the hospital is an identified medical problem and is addressed by a new medical field termed "blood management." Nationally, greater than 50% of transfusions administered do not meet hospital guidelines, thereby resulting in over-treatment of large numbers of patients with a biologic product associated with significant risk and expense. These risks include, but are not limited to, cardiac overload, infection, increased length of hospital stay, and death. Risk can increase in a dose-dependent manner, and even a small amount of blood received, such as transfusion of one unnecessary unit of blood, is considered an undesirable event.

Despite these risks, blood transfusion is the most common procedure in hospitals, and blood transfusion has increased in U.S. hospitals by 140% over the last 10 years. Approximately 17 million transfusions of red blood cells are performed annually in the U.S. The direct cost for the blood component and infusion accounts for about 5% of a hospital's budget. For a single transfusion of red blood cells, the direct cost is about $1,000. However, when the cost associated with adverse events is considered (increased length of stay, infection, etc.), the true cost doubles to $2,000 to $2,500 per transfusion.

Blood management is defined as the appropriate use of blood components with a focus on minimizing blood use and currently is directed at in-hospital transfusion practice. This focus fails to consider the significant population of patients who present for non-emergent scheduled surgeries routinely associated with high blood loss, such as cardiovascular and orthopedic procedures, with low blood counts (anemia) and, thus, have a predictable risk of receiving allogeneic donor blood. Other surgeries associated with high blood loss include gastrointestinal surgery, gynecologic oncology surgery, vascular surgery, urologic surgery, neurosurgery, and others.

Approximately 2.5 million patients in the United States undergo non-emergent high blood loss surgeries annually, and up to 40% are anemic on presentation to the hospital. Anemia prevalence varies by surgical demographic group with 35% anemia prevalence in joint replacement patients and 60% anemia prevalence rate in cardiac valve replacement patients. Current practice is to conduct a preoperative history and physical examination with lab work, including hemoglobin evaluation, in the week prior to surgery. The timeframe for this assessment does not allow for either etiology determination or treatment of anemia prior to surgery, and surgery is cancelled for only profoundly anemic patients. As many as fifty five (55%) percent of non-emergent surgical patients have no preoperative anemia screening. The screening process is generally not standardized, and there is no expectation that treatable anemia be corrected before surgery is performed. Prospective risk assessment for transfusion, irrespective of anemia, is not performed to stratify surgical patients into high or low risk for receipt of stored blood and, as such, methods to decrease blood loss are generally not employed for high risk patients.

New protocols and tools are needed to effectively assess and treat patients scheduled for high blood loss procedures or having other indications that increase the likelihood of transfusion. These protocols and methods need to be reliable, reproducible, and measurable from a risk reduction and financial savings standpoint.

SUMMARY OF THE INVENTION

The methods and devices described herein can be readily applied to evaluate and treat certain chronic disease populations with high prevalence of anemia (e.g., chronic heart failure (CHF), inflammatory bowel disease, autoimmune disease, chronic viral disease and diabetes) and a subset of these patients without anemia but symptomatic from associated elemental deficiency states, such as iron-depletion or iron-deficiency (e.g., CHF patients).

In particular, the invention provides methods of identifying and treating patients preparing to undergo non-emergent surgery or suffering from chronic disease. In these patient populations, treatment for underlying symptoms related to anemia or iron-depleted states can result in better health outcomes. Accordingly, the invention provides methods for identifying a subject with anemia and/or otherwise a high risk of receiving a transfusion (e.g., receiving allogeneic blood) and treating a subject to minimize that risk by use of a patient care plan. In particular, the method relates to mitigating the risk of receiving allogeneic blood, such as by preoperatively assessing the patient within a timeframe that allows for correction or minimization of anemia prior to surgery and for development of an in-hospital transfusion minimization strategy for patients having a risk of transfusion at the time of surgery. Furthermore, the invention provides methods for identifying and treating a subject having a chronic disease associated with anemia, iron-depletion, or iron-deficiency by use of a patient care plan.

In a first aspect, the invention features a method of treating a subject preparing to undergo a non-emergent surgery, the method including: receiving a profile of the subject, in a physical computing device, where the profile includes level of hemoglobin of the subject, level of creatinine of the subject, and information regarding current or past history of disease of the subject; applying the level of hemoglobin and the level of creatinine, in the physical computing device, to determine level of transfusion risk; applying the information regarding current or past history of disease of the subject, in the physical computing device, to determine level of comorbidity; applying the level of hemoglobin, the level of transfusion risk, and the level of comorbidity, in the physical computing device, to determine a patient care plan; and administering the patient care plan to treat the subject prior to the subject undergoing the non-emergent surgery. In a further embodiment of the first aspect, the profile further includes type of the non-emergent surgery and red cell antibody information, and the method includes: applying the type of the non-emergent surgery, in the physical computing device, to determine a range of anticipated loss of blood volume; applying the range of anticipated loss of blood volume and the level of comorbidity, in the physical computing device, to determine a range of tolerable loss of blood volume; applying the red cell antibody information, in the physical computing device, to determine one or more compatible blood types; applying the range of anticipated loss of blood volume, the range of tolerable loss of blood volume, and the one or more compatible blood types, in the physical computing device, to determine an in-hospital transfusion minimization care plan; and administering the in-hospital transfusion minimization care plan to treat the subject during or after undergoing the non-emergent surgery.

In a second aspect, the invention features a method of treating a subject preparing to undergo a non-emergent surgery, the method including: receiving a profile of the subject, in a physical computing device, where the profile includes level of hemoglobin of the subject, level of creatinine of the subject, and information regarding current or past history of disease of the subject; applying the level of hemoglobin and the level of creatinine, in the physical computing device, to determine level of transfusion risk using a physical computing device, where the applying includes comparing the level of hemoglobin to a predetermined threshold for hemoglobin (e.g., 9.0 g/dL, 9.4 g/dL, 9.5 g/dL, 9.9 g/dL, 10.0 g/dL, 10.4 g/dL, 10.5 g/dL, 10.9 g/dL, 11.0 g/dL, 11.4 g/dL, 11.5 g/dL, 11.9 g/dL, 12.0 g/dL, 12.4 g/dL, 12.5 g/dL, 12.9 g/dL, 13.0 g/dL, 13.4 g/dL, 13.5 g/dL, 13.9 g/dL, 14.0 g/dL, 14.4 g/dL, 14.5 g/dL, or 14.9 g/dL, such as about 10.0 g/dL, 11.4 g/dL, 11.5 g/dl, 12.9 g/dL, 13.0 g/dL, or 13.4 g/dL), where the level of hemoglobin lower than the predetermined threshold indicates increased level of transfusion risk, and comparing the level of creatinine to a predetermined threshold for creatinine (e.g., 1.0 mg/dL, 1.1 mg/dL, 1.2 mg/dL, 1.3 mg/dL, 1.4 mg/dL, 1.5 mg/dL, 1.6 mg/dL, 1.7 mg/dL, 1.8 mg/dL, 1.9 mg/dL, 2.0 mg/dL, 2.1 mg/dL, 2.2 mg/dL, 2.3 mg/dL, 2.4 mg/dL, or 2.5 mg/dL, such as about 1.2 mg/dL, 1.9 mg/dL, or 2.0 mg/dL), where the level of creatinine higher than the predetermined threshold indicates increased level of transfusion risk; applying the information regarding current or past history of disease of the subject, in the physical computing device, to determine level of comorbidity using a physical computing device, where the applying includes comparing the information to a predetermined comorbid condition (e.g., cardiovascular disease, cerebrovascular disease, pulmonary disease, renal disease, cancer, autoimmune disease, gastrointestinal disease, inflammatory disease, active infection, or blood clotting disorder), where the presence of the predetermined comorbid condition in the information indicates increased level of comorbidity; applying the level of hemoglobin, the level of transfusion risk, and the level of comorbidity, in the physical computing device, to determine a patient care plan using a physical computing device, where the determining includes comparing the level of hemoglobin to a predetermined value of hemoglobin indicative of anemia (e.g., 9.0 g/dL, 9.4 g/dL, 9.5 g/dL, 9.9 g/dL, 10.0 g/dL, 10.4 g/dL, 10.5 g/dL, 10.9 g/dL, 11.0 g/dL, 11.4 g/dL, 11.5 g/dL, 11.9 g/dL, 12.0 g/dL, 12.4 g/dL, 12.5 g/dL, 12.9 g/dL, 13.0 g/dL, 13.4 g/dL, 13.5 g/dL, 13.9 g/dL, or 14.0 g/dL, such as about 12.9 g/dL, 13.0 g/dL, or 13.4 g/dL) and the patient care plan includes one or more treatments for the anemia, the increased level of transfusion risk, or the increased level of comorbidity; and administering the patient care plan to treat the subject prior to the subject undergoing the non-emergent surgery. In a further embodiment of the second aspect, the profile further includes type of said non-emergent surgery and red cell antibody information, and the method includes: applying the type of the non-emergent surgery, in the physical computing device, to determine a range of anticipated loss of blood volume, where the applying includes comparing the type of the non-emergent surgery to a predetermined threshold range of anticipated loss of blood volume (e.g. between 500 mL-5,000 mL, 500 mL-4,500 mL, 500 mL-4,000 mL, 500 mL-3,500 mL, 500 mL-3,000 mL, 500 mL-2,500 mL, 500 mL-2,000 mL, 500 mL-1,500 mL, 500 mL-1,000 mL, 1,000 mL-5,000 mL, 1,000 mL-4,500 mL, 1,000 mL-4,000 mL, 1,000 mL-3,500 mL, 1,000 mL-3,000 mL, 1,000 mL-2,500 mL, 1,000 mL-2,000 mL, 1,500 mL-5,000 mL, 1,500 mL-4,500 mL, 1,500 mL-4,000 mL, 1,500 mL-3,500 mL, 1,500 mL-3,000 mL, 1,5000 mL-2,500 mL, 1,500 mL-2,000 mL, 2,000 mL-5,000 mL, 2,000 mL-4,500 mL, 2,000 mL-4,000 mL, 2,000 mL-3,500 mL, 2,000 mL-3,000 mL, 2,000 mL-2,500 mL, 2,500 mL-5,000 mL, 2,500 mL-4,500 mL, 2,500 mL-4,000 mL, 2,500 mL-3,500 mL, 2,500 mL-3,000 mL, 3,000 mL-5,000 mL, 3,000 mL-4,500 mL, 3,000 mL-4,000 mL, or 3,000 mL-3,500 mL, such as 2,000 mL-2,500 mL for cardiovascular surgery, 1,000 mL-3,000 mL for spinal surgery, and 500 mL-2,500 for hip and knee arthroplasty); applying the range of anticipated loss of blood volume and the level of comorbidity, in the physical computing device, to determine a range of tolerable loss of blood volume (e.g., 10%, 11%, 12%, 13%, 14%, 15%, 16% 17%, 18%, 19%, 20%, 21%, 22%, 23%, 24%, or 25%, such as about 20%, as compared to initial blood volume prior to the non-emergent surgery), where the applying includes determining the range of tolerable loss of blood volume based on a minimum tolerable hematocrit associated with the level of comorbidity (e.g., a minimum tolerable hematocrit of between 18%-33%, 18%-30%, 18%-27%, 18%-24%, 18%-21%, 21%-33%, 21%-30%, 21%-27%, 21%-24%, 24%-33%, 24%-30%, or 24%-27% for no comorbid conditions, including 21%-24% without significant comorbid conditions, such as active cardiovascular disease; or a minimum tolerable hematocrit of between 18%-33%, 18%-30%, 18%-27%, 18%-24%, 18%-21%, 21%-33%, 21%-30%, 21%-27%, 21%-24%, 24%-33%, 24%-30%, or 24%-27% for one or more comorbid conditions, including 24%-30% with one or more comorbid conditions, such as cardiovascular disease); applying the red cell antibody information, in the physical computing device, to determine one or more compatible blood types, where the applying includes determining one or more blood types compatible with the presence of one or more red cell antibodies identified in the red cell antibody information (e.g., using an ABO typing test and/or a Rh typing test); applying the range of anticipated loss of blood volume, the range of tolerable loss of blood volume, and the one or more compatible blood types, in the physical computing device, to determine an in-hospital transfusion minimization care plan, where the in-hospital transfusion minimization care plan includes use of one or more blood components having the range of anticipated loss of blood volume and having the compatible blood type when the subject loses more blood than the range of tolerable loss of blood volume during the non-emergent surgery; and administering the in-hospital transfusion minimization care plan to treat the subject during or after undergoing the non-emergent surgery.

In a third aspect, the invention features a method of treating a subject preparing to undergo a non-emergent surgery, the method including: receiving a profile of the subject, in a physical computing device, where the profile includes level of hemoglobin of the subject, level of creatinine of the subject, information regarding current or past history of disease of the subject, type of the non-emergent surgery, and red cell antibody information of the subject; receiving a patient care plan, in the physical computing device, where the level of hemoglobin, the level of creatinine, and the profile is used to determine the patient care plan; administering the patient care plan to treat the subject prior to the subject undergoing the non-emergent surgery; managing the subject though notification and support, in the physical computing device; receiving an in-hospital transfusion minimization care plan, in the physical computing device, including a range of anticipated loss of blood volume, a range of tolerable loss of blood volume, and one or more compatible blood types, where the profile is used to determine the range of anticipated loss of blood volume, the range of tolerable loss of blood volume, and the one or more compatible blood types; and administering the in-hospital transfusion minimization care plan to treat the subject prior to the subject undergoing the non-emergent surgery.

In a fourth aspect, the invention features a method of reducing transfusions during or after a non-emergent surgery, the method including: receiving a profile of a subject preparing to undergo a non-emergent surgery, in a physical computing device, where the profile contains level of hemoglobin of the subject, level of creatinine of the subject, and information regarding current or past history of disease of the subject; applying the profile, in the physical computing device, to determine level of transfusion risk and level of comorbidity; applying the level of hemoglobin, the level of transfusion risk, and the level of comorbidity, in the physical computing device, to determine a patient care plan; applying the profile, in the physical computing device, to determine level of bleeding risk; applying the level of hemoglobin, the level of creatinine, and the level of bleeding risk, in the physical computing device, to determine a first test panel, where the first test panel indicates whether or not one or more laboratory tests need to be performed; and outputting the patient care plan and the first test panel to one or more of a computer readable medium, a server, a network, a display device, or a printed report. In a further embodiment of the fourth aspect, the profile further contains the type of the non-emergent surgery and red cell antibody information of the subject, and the method further includes the steps of: applying the type of the non-emergent surgery, in the physical computing device, to determine a range of anticipated loss of blood volume; applying the range of anticipated loss of blood volume and the level of comorbidity, in the physical computing device, to determine a range of tolerable loss of blood volume; applying the red cell antibody information, in the physical computing device, to determine one or more compatible blood types; applying the range of anticipated loss of blood volume, the range of tolerable loss of blood volume, the one or more compatible blood types, and the level of comorbidity, in the physical computing device, to determine an in-hospital transfusion minimization plan; applying the red cell antibody information, in the physical computing device, to determine a second test panel, where the second test panel indicates whether or not one or more laboratory tests need to be performed; and outputting the in-hospital transfusion minimization plan and the second test panel to one or more of the computer readable medium, the server, the network, the display device, or the printed report.

In a fifth aspect, the invention features a method of reducing transfusions during or after a non-emergent surgery, the method including: receiving a profile of a subject preparing to undergo a non-emergent surgery, in a physical computing device, where the profile includes level of hemoglobin of the subject, level of creatinine of the subject, and information regarding current or past history of disease of the subject; applying the profile, in the physical computing device, to determine level of transfusion risk and level of comorbidity, where the applying includes: comparing the level of hemoglobin to a predetermined threshold for hemoglobin (e.g., 9.0 g/dL, 9.4 g/dL, 9.5 g/dL, 9.9 g/dL, 10.0 g/dL, 10.4 g/dL, 10.5 g/dL, 10.9 g/dL, 11.0 g/dL, 11.4 g/dL, 11.5 g/dL, 11.9 g/dL, 12.0 g/dL, 12.4 g/dL, 12.5 g/dL, 12.9 g/dL, 13.0 g/dL, 13.4 g/dL, 13.5 g/dL, 13.9 g/dL, 14.0 g/dL, 14.4 g/dL, 14.5 g/dL, or 14.9 g/dL, such as about 10.0 g/dL, 11.4 g/dL, 11.5 g/dl, 12.9 g/dL, 13.0 g/dL, or 13.4 g/dL), where the level of hemoglobin lower than the predetermined threshold indicates increased level of transfusion risk; comparing the level of creatinine to a predetermined threshold for creatinine (e.g., 1.0 mg/dL, 1.1 mg/dL, 1.2 mg/dL, 1.3 mg/dL, 1.4 mg/dL, 1.5 mg/dL, 1.6 mg/dL, 1.7 mg/dL, 1.8 mg/dL, 1.9 mg/dL, 2.0 mg/dL, 2.1 mg/dL, 2.2 mg/dL, 2.3 mg/dL, 2.4 mg/dL, or 2.5 mg/dL, such as about 1.2 mg/dL, 1.9 mg/dL, or 2.0 mg/dL), where the level of creatinine higher than the predetermined threshold indicates increased level of transfusion risk; and comparing the information to a predetermined comorbid condition (e.g., cardiovascular disease, cerebrovascular disease, pulmonary disease, renal disease, cancer, autoimmune disease, gastrointestinal disease, inflammatory disease, active infection, or blood clotting disorder), where the presence of the predetermined comorbid condition in the information indicates increased level of comorbidity; applying the level of hemoglobin, the level of transfusion risk, and the level of comorbidity, in the physical computing device, to determine a patient care plan, where the determining includes comparing the level of hemoglobin to a predetermined value of hemoglobin indicative of anemia (e.g., 9.0 g/dL, 9.4 g/dL, 9.5 g/dL, 9.9 g/dL, 10.0 g/dL, 10.4 g/dL, 10.5 g/dL, 10.9 g/dL, 11.0 g/dL, 11.4 g/dL, 11.5 g/dL, 11.9 g/dL, 12.0 g/dL, 12.4 g/dL, 12.5 g/dL, 12.9 g/dL, 13.0 g/dL, 13.4 g/dL, 13.5 g/dL, 13.9 g/dL, or 14.0 g/dL, such as about 12.9 g/dL, 13.0 g/dL, or 13.4 g/dL) and the patient care plan includes one or more treatments for the anemia, the increased level of transfusion risk, or the increased level of comorbidity; applying the profile, in the physical computing device, to determine level of bleeding risk, where the applying includes comparing the information to a predetermined bleeding risk condition (e.g., history of abnormal coagulopathy, such as hemophilia A or B, von Willebrand disease, liver disease, or vitamin K deficiency; whether the subject has a past history of bleeding; or whether the subject takes one or more procoagulant medications) and where the presence of the predetermined bleeding risk condition in the information indicates increased level of bleeding risk; applying the level of hemoglobin, the level of creatinine, and the level of bleeding risk, in the physical computing device, to determine a first test panel, where the first test panel indicates whether or not one or more laboratory tests need to be performed; and outputting the patient care plan and the first test panel to one or more of a computer readable medium, a server, a network, a display device, or a printed report. In a further embodiment, the profile further includes type of the non-emergent surgery and red cell antibody information of the subject, and the method further includes: applying the type of the non-emergent surgery, in the physical computing device, to determine a range of anticipated loss of blood volume, where the applying includes comparing the type of the non-emergent surgery to a predetermined threshold range of anticipated loss of blood volume (e.g. between 500 mL-5, 000 mL, 500 mL-4,500 mL, 500 mL-4,000 mL, 500 mL-3,500 Ml, 500 mL-3,000 mL, 500 mL-2,500 mL, 500 mL-2,000 mL, 500 mL-1,500 mL, 500 mL-1,000 mL, 1,000 mL-5,000 mL, 1,000 mL-4,500 mL, 1,000 mL-4,000 mL, 1,000 mL-3,500 mL, 1,000 mL-3,000 mL, 1,000 mL-2,500 mL, 1,000 mL-2,000 mL, 1,500 mL-5,000 mL, 1,500 mL-4,500 mL, 1,500 mL-4,000 mL, 1,500 mL-3,500 mL, 1,500 mL-3,000 mL, 1,5000 mL-2,500 mL, 1,500 mL-2,000 mL, 2,000 mL-5,000 mL, 2,000 mL-4,500 mL, 2,000 mL-4,000 mL, 2,000 mL-3,500 mL, 2,000 mL-3,000 mL, 2,000 mL-2,500 mL, 2,500 mL-5,000 mL, 2,500 mL-4,500 mL, 2,500 mL-4,000 mL, 2,500 mL-3,500 mL, 2,500 mL-3,000 mL, 3,000 mL-5,000 mL, 3,000 mL-4,500 mL, 3,000 mL-4,000 mL, or 3,000 mL-3,500 mL, such as 2,000 mL-2,500 mL for cardiovascular surgery, 1,000 mL-3,000 mL for spinal surgery, and 500 mL-2,500 for hip and knee arthroplasty); applying the range of anticipated loss of blood volume and the level of comorbidity, in the physical computing device, to determine a range of tolerable loss of blood volume (e.g., 10%, 11%, 12%, 13%, 14%, 15%, 16% 17%, 18%, 19%, 20%, 21%, 22%, 23%, 24%, or 25%, such as about 20%, as compared to initial blood volume prior to the non-emergent surgery), where the applying includes determining the range of tolerable loss of blood volume based on a minimum tolerable hematocrit associated with the level of comorbidity (e.g., a minimum tolerable hematocrit of between 18%-33%, 18%-30%, 18%-27%, 18%-24%, 18%-21%, 21%-33%, 21%-30%, 21%-27%, 21%-24%, 24%-33%, 24%-30%, or 24%-27% for no comorbid conditions, including 21%-24% without significant comorbid conditions, such as active cardiovascular disease; or a minimum tolerable hematocrit of between 18%-33%, 18%-30%, 18%-27%, 18%-24%, 18% 21%, 21%-33%, 21%-30%, 21%-27%, 21%-24%, 24%-33%, 24%-30%, or 24%-27% for one or more comorbid conditions, including 24%-30% with one or more comorbid conditions, such as cardiovascular disease); applying red cell antibody information, in the physical computing device, to determine one or more compatible blood types, where the applying includes determining one or more blood types compatible with the presence of one or more red cell antibodies identified in the red cell antibody information (e.g., using an ABO typing test and/or a Rh typing test); applying the range of anticipated loss of blood volume, the range of tolerable loss of blood volume, the one or more compatible blood types, and the level of comorbidity, in the physical computing device, to determine an in-hospital transfusion minimization care plan, where the in-hospital transfusion minimization care plan includes use of one or more blood components having the range of anticipated loss of blood volume and having the compatible blood type when the subject loses more blood than the range of tolerable loss of blood volume during the non-emergent surgery; applying the red cell antibody information, in the physical computing device, to determine a second test panel, where the second test panel indicates whether or not one or more laboratory tests need to be performed; and outputting the in-hospital transfusion minimization care plan and the second test panel to one or more of the computer readable medium, the server, the network, the display device, or the printed report.

In further embodiments of any of the above aspects, the non-emergent surgery is an orthopedic surgery (e.g., primary or revision total knee replacement surgery that is single or bilateral, primary or revision partial knee replacement surgery that is single or bilateral, primary or revision total hip joint arthroplasty, or spine surgery), a cardiovascular surgery (e.g., of cardiac valve replacement, cardiac valve repair, coronary artery bypass surgery, coronary artery bypass surgery with cardiac valve repair or replacement, and aortic replacement surgery), a genitourinary surgery (e.g., radical retropubic prostatectomy or cystectomy), a gastrointestinal surgery (e.g., to treat cancer, such as an esophagectomy, a gastrectomy, or a colectomy, or to treat an inflammatory bowel disease, such as a colectomy), other vascular surgery (e.g., aneurysm repair), a gynecology surgery (e.g., gynecological oncology surgery or uterine cancer surgery, such as a hysterectomy with or without bilateral salpingo-oophorectomy, tumor debulking, omentectomy, or lymph node sampling), a neurosurgery (e.g., meningioma resection or surgery to correct a vascular malformation), an oncologic thoracic surgery (e.g., for the removal of a lung tumor), a high-risk caesarian delivery, or any combination thereof.

In particular embodiments of any of the above aspects, the profile further includes information regarding a health insurance plan and a health insurance provider of the subject, and the method further includes: comparing, in the physical computing device, the medical procedure, laboratory test, treatment, or medication indicated in the patient care plan, the in-hospital transfusion minimization care plan, the first test panel, and/or the second test panel with the types of medical procedure, laboratory test, treatment, or medication allowed or restricted by the health insurance plan; determining, in the physical computing device, whether coverage of the patient care plan, the in-hospital transfusion minimization care plan, the first test panel, and/or the second test panel requires pre-authorization by the subject's healthcare provider; and requesting and documenting, in the physical computing device, approval of the pre-authorization by the health insurance provider. In further embodiments, the method includes outputting the results of the comparing, determining, requesting, and documenting steps to one or more of the computer readable medium, the server, the network, the display device, or the printed report.

In any of the above aspects, the patient care plan includes one or more of oral iron (e.g., with or without ascorbic acid), intravenous iron (e.g., ferric carboxymaltose, iron sucrose, and iron dextran), an erythropoietic medication (e.g., erythropoietin, epoetin, epoetin alfa, darbepoetin alfa, epoetin delta, PDpoetin, and methoxy polyethylene glycol-epoetin beta), folate, vitamin B12, desmopressin acetate, preoperative dialysis, preoperative coagulation therapy, preoperative autologous blood donation, cell saver, postoperative iron (e.g., oral iron with or without ascorbic acid or intravenous iron, including ferric carboxymaltose, iron sucrose, and iron dextran), use of pediatric blood tubes for blood draws, or discontinuation of one or more anticoagulant medications between about one week to about two weeks before the date of the non-emergent surgery.

In any of the above aspects, the in-hospital transfusion minimization plan may include use of a transfusion product having a shelf age of less than 14 days or having a higher than physiological range of hemoglobin.

In further embodiments of any of the above aspects, the profile further includes weight, gender, age, date of the non-emergent surgery, level of creatinine, information regarding whether the non-emergent surgery is a redo procedure, and information regarding whether the non-emergent surgery is a non-isolated procedure; and applying the profile, in the physical computing device, to determine the level of transfusion risk includes: applying the level of hemoglobin to determine a first value, where if the level of hemoglobin is between 10.0 g/dL-11.4 g/dL (e.g., or alternatively between 10.6 g/dL-11.5 g/dL), then the first value is two, where if the level of hemoglobin is above 11.4 g/dL and below 13.0 g/dL (e.g., between 11.5 g/dL-12.9 g/dL or alternatively between 11.5 g/dL-13.4 g/dL), then the first value is one, and where if the level of hemoglobin is more than or equal to 13.0 g/dL (e.g., or more than or equal to 13.5 g/dL), then the first value is zero; applying the weight to determine a second value, where if the weight is less than 50 kg, the second value is two, where if the weight is between 50 kg-75 kg, then the second value is one, and where if the weight is more than 75 kg, then the second value is zero; applying the gender to determine a third value, where if the gender is female, then the third value is one, and where if the gender is male, then the third value is zero; applying the age to determine a fourth value, where if the age is more than or equal to 65 years, then the fourth value is one, and where if the age is less than 65 years, then the fourth value is zero; applying the date of the non-emergent surgery to determine a fifth value, where if the date of the non-emergent surgery is less than two weeks away, then the fifth value is one, and where if the date of the non-emergent surgery is more than or equal to two weeks away, then the fifth value is zero; applying the level of creatinine to determine a sixth value, where if the level of creatinine is more than or equal to 2.0 mg/dL, then the sixth value is two, where if the level of creatinine is between 1.2 mg/dL-1.9 mg/dL, then the sixth value is one, and where if the level of creatinine is less than 1.2 mg/dL, then the sixth value is zero; applying the information regarding whether the non-emergent surgery is a redo procedure to determine a seventh value, where if the non-emergent surgery is a redo procedure, then the seventh value is one, and where if the non-emergent surgery is not a redo procedure, then the seventh value is zero; applying the information regarding whether the non-emergent surgery is a non-isolated procedure to determining an eighth value, where if the non-emergent surgery is a non-isolated procedure, then the eighth value is one; and where if the non-emergent surgery is an isolated procedure, then the eighth value is zero; and outputting the level of transfusion risk to one or more of the computer readable medium, the server, the network, the display device, or the printed report, where: if the sum of the first value to the eighth value is less than or equal to one, then the level of transfusion risk is low; if the sum of the first value to the eighth value is two, then the level of transfusion risk is intermediate; if the sum of the first value to the eighth value is three, then the level of transfusion risk is high; and if the sum of the first value to the eighth value is more than three, then the level of transfusion risk is very high; and where applying the profile to determine the level of comorbidity includes: applying the information regarding current or past history of disease to determine the level of comorbidity, where: if the information regarding current or past history of disease includes past history of cardiovascular disease, cerebrovascular disease, pulmonary disease, renal disease, cancer, autoimmune disease, gastrointestinal disease, inflammatory disease, active infection, or blood clotting disorder, then the level of comorbidity includes one or more comorbid conditions.

In further embodiments of any of the above aspects, applying the level of hemoglobin, the level of transfusion risk, and the level of comorbidity, in the physical computing device, to determine the patient care plan includes: determining whether the level of hemoglobin results in the first value being one or zero; determining whether the level of transfusion risk is low, intermediate, high, or very high; determining whether the level of comorbidity includes one or more comorbid conditions; and selecting the patient care plan based on the level of hemoglobin, the level of transfusion risk, and the one or more comorbid conditions, where: if the first value is zero, the level of transfusion risk is low or intermediate, and the one or more comorbid conditions are not present, then the patient care plan includes one or more of oral iron, ascorbic acid, or a multivitamin; if the one or more comorbid conditions are present, then the patient care plan includes one or more of an erythropoietic medication, intravenous iron, oral iron, desmopressin acetate, preoperative dialysis, preoperative coagulation therapy, or preoperative autologous blood donation; and if the first value is one or the level of transfusion risk is high or very high, then the patient care plan includes one or more of intravenous iron, cell saver, preoperative autologous blood donation, postoperative iron, or use of pediatric blood tubes for blood draws. In a further embodiment, the profile further includes information regarding medication taken by the subject, and applying the level of hemoglobin, the level of transfusion risk, and the level of comorbidity, in the physical computing device, to determine the patient care plan further includes: applying the information regarding medication taken by the subject to determine a ninth value, where if the information regarding medication taken by the subject includes one or more anticoagulant medications, then the ninth value is positive; and applying the ninth value to further determine the patient care plan, where if the ninth value is positive, then the patient care plan further includes discontinuation of the one or more anticoagulant medications between about one week to about two weeks before the date of the non-emergent surgery. In another embodiment, applying the level of hemoglobin, the level of transfusion risk, and the level of comorbidity, in the physical computing device, to determine the patient care plan further includes: applying the date of the non-emergent surgery to determine a tenth value, where if the date of the non-emergent surgery is more than one week away, then the tenth value is zero; and applying the first value and the tenth value to further determine the patient care plan, where if the first value is positive (e.g., one, two, or any positive integer) and the tenth value is zero, then the patient care plan further includes administration of one or more of oral iron (e.g., with or without ascorbic acid), intravenous iron, ferric carboxymaltose, iron sucrose, iron dextran, ascorbic acid, erythropoietin, folate, vitamin B12, epoetin, epoetin alfa, darbepoetin alfa, epoetin delta, PDpoetin, or methoxy polyethylene glycol-epoetin beta.

In additional embodiments of any of the above aspects, the method further includes: receiving a revised level of hemoglobin of the subject, in the physical computing device, where the revised level of hemoglobin is determined after the subject is treated with the patient care plan; receiving a revised profile of the subject, in the physical computing device, where the revised profile is determined after the subject is treated with the patient care plan; applying the revised level of hemoglobin and the revised profile, in the physical computing device, to determine a revised level of transfusion risk; applying the revised level of hemoglobin and the revised level of transfusion risk, in the physical computing device, to determine a revised patient care plan; and outputting the revised level of hemoglobin and the revised patient care plan to one or more of the computer readable medium, the server, the network, the display device, or the printed report. In particular embodiments, the revised profile further includes revised weight, gender, revised age, revised date of the non-emergent surgery, revised level of creatinine, revised information regarding whether or not the non-emergent surgery is a redo procedure, and revised information regarding whether or not the non-emergent surgery is a non-isolated procedure.

In additional embodiments of any of the above aspects, applying the level of comorbidity, in the physical computing device, to determine an in-hospital transfusion minimization care plan includes: determining whether the level of comorbidity includes one or more comorbid conditions; and selecting a transfusion product based on the level of comorbidity, where if the one or more comorbid conditions are present, then the transfusion product has a shelf age of less than 14 days or contains a higher than physiological range of hemoglobin.

In yet other embodiments of any of the above aspects, the method further includes: receiving information regarding the subject after undergoing the non-emergent surgery, in the physical computing device, where the information regarding the subject after undergoing the non-emergent surgery includes information regarding loss of blood volume during the non-emergent surgery, information regarding whether the subject had a transfusion during the non-emergent surgery, and information regarding adverse events; applying the information regarding the subject after undergoing the non-emergent surgery, the profile, the level of transfusion risk, the level of comorbidity, the patient care plan, and the in-hospital transfusion minimization care plan, in the physical computing device, to determine a patient outcome report; and outputting the patient outcome report to one or more of a computer readable medium, a server, a network, a display device, or a printed report. In further embodiments, the method further includes applying the patient outcome report to treat the subject after undergoing the non-emergent surgery.

In other embodiments of any of the above aspects, the method further includes: applying the profile, in the physical computing device, to determine level of bleeding risk; applying the level of hemoglobin, the level of creatinine, and the level of bleeding risk, in the physical computing device, to determine a first test panel, where the first test panel indicates whether or not one or more laboratory tests need to be performed; applying the red cell antibody information, in the physical computing device, to determine a second test panel, where the second test panel indicates whether or not one or more laboratory tests need to be performed; and outputting the first test panel and the second test panel to one or more of a computer readable medium, a server, a network, a display device, or a printed report.

In additional embodiments of any of the above aspects, the profile further includes information regarding medication taken by the subject, and applying the profile, in the physical computing device, to determine the level of bleeding risk includes: applying the information regarding current or past history of disease to determine an eleventh value, where if the information regarding current or past history of disease includes past history of bleeding, then the eleventh value is positive; and applying the information regarding medication taken by the subject to determine a twelfth value, where: if the information regarding medication taken by the subject includes one or more procoagulant medications, then the twelfth value is positive; and if one or more of the eleventh value to the twelfth value are positive, then the level of bleeding risk is high.

In other embodiments of any of the above aspects, applying the level of bleeding risk, in the physical computing device, to determine the first test panel includes: using the eleventh value and twelfth value to determine the level of bleeding risk; and selecting the one or more laboratory tests if the level of bleeding risk is high, where the one or more laboratory tests are selected from the group consisting of a screening coagulation panel and a special coagulation test.

In additional embodiments of any of the above aspects, applying the level of hemoglobin and the level of creatinine, in the physical computing device, to determine the first test panel includes: applying the level of hemoglobin to determine whether the subject is anemic or whether the level of hemoglobin has been determined recently; selecting the one or more laboratory tests if the subject is anemic or if the level of hemoglobin is not recent, where the one or more laboratory tests are selected from the group consisting of an iron assessment panel, a complete blood count, a hemoglobin test, a vitamin B12 test, a folate test, and a C reactive protein assay; applying the level of creatinine to determine whether the level of creatinine has been determined recently; and selecting the one or more laboratory tests if the level of creatinine is not recent, where the one or more laboratory tests are selected from the group consisting of a creatinine test (e.g., with calculated glomerular filtration rate) and a blood urea nitrogen test.

In particular embodiments of any of the above aspects, applying the red cell antibody information, in the physical computing device, to determine the second test panel includes: applying the red cell antibody information to determine whether one or more red cell antibodies are present; and selecting the one or more laboratory tests if the one or more red cell antibodies are present, where the one or more laboratory tests are selected from the group consisting of a red cell antibody identification test, a direct antiglobulin test, an indirect antiglobulin test, and a blood typing test. In further embodiments, the method further includes outputting the results of the one or more laboratory tests if the one or more red cell antibodies are present, and providing the results to a healthcare provider to ensure that blood components compatible with the one or more red cell antibodies are available for transfusion during the non-emergent surgery.

In further embodiments of any of the above aspects, the method further includes: applying the information regarding current or past history of disease, in the physical computing device, to determine level of renal risk, where if the information regarding current or past history of disease includes current or past history of renal disease or current or past history of diabetes, then the level of renal risk is high; applying the level of renal risk, in the physical computing device, to determine a third test panel, where the third test panel indicates whether one or more laboratory tests need to be performed, and where if the level of renal risk is high, then the third test panel includes one or more of a creatinine test with calculated glomerular filtration rate or a blood urea nitrogen test; and outputting the third test panel to one or more of the computer readable medium, the server, the network, the display device, or the printed report. In some embodiments, where if the level of renal risk is high, then the patient care plan further includes a consultation with a renal specialist, and where if the level of creatinine is more than 2 mg/dL, then the patient care plan further includes dialysis.

In any of the above aspects, the method further includes outputting a patient satisfaction outcome report, a hospital satisfaction outcome report, an adverse event outcome report, or a surgical outcome-specific report including the patient care plan, the in-hospital transfusion minimization care plan, the revised patient care plan, the first test panel, the second test panel, and/or the third test panel to one or more of the computer readable medium, the server, the network, the display device, or the printed report.

In a sixth aspect, the invention features a method of continuously treating (e.g., at least 2, 3, 4, 5, 6, 7, 8, 9, 10, 11, 12, or more times a year) a subject having a chronic disease, the method including: receiving a profile of the subject, in a physical computing device, where the profile includes level of hemoglobin of the subject and level of blood health index of the subject; applying the level of hemoglobin or the level of blood health index, in the physical computing device, to determine a patient care plan; administering the patient care plan to treat the subject; selecting one or more laboratory tests, in the physical computing device, where the one or more laboratory tests are selected from the group consisting of a creatinine test (e.g., with a calculated glomerular filtration rate test), a glomerular filtration rate test, a vitamin B12 test, and a folate test; receiving a revised level of hemoglobin of the subject or a revised level of blood health index of the subject, in the physical computing device, where the revised levels are determined after the subject is treated with the patient care plan and the revised levels are determined on a continuous basis for a year (e.g., determined at least 2, 3, 4, 5, 6, 7, 8, 9, 10, 11, 12, or more times a year); applying the revised level of hemoglobin or the revised level of blood health index, in the physical computing device, to determine a revised patient care plan; and administering the revised patient care plan to treat the subject.

In a seventh aspect, the invention features a method of continuously treating (e.g., at least 2, 3, 4, 5, 6, 7, 8, 9, 10, 11, 12, or more times a year) a subject having a chronic disease, the method including: receiving a profile of the subject, in a physical computing device, where the profile includes level of hemoglobin of the subject and level of blood health index of the subject; applying the level of hemoglobin or the level of blood health index, in the physical computing device, to determine a patient care plan, where the applying includes comparing the level of hemoglobin to a predetermined threshold for hemoglobin (e.g., 9.0 g/dL, 9.4 g/dL, 9.5 g/dL, 9.9 g/dL, 10.0 g/dL, 10.4 g/dL, 10.5 g/dL, 10.9 g/dL, 11.0 g/dL, 11.4 g/dL, 11.5 g/dL, 11.9 g/dL, 12.0 g/dL, 12.4 g/dL, 12.5 g/dL, 12.9 g/dL, 13.0 g/dL, 13.4 g/dL, 13.5 g/dL, 13.9 g/dL, or 14.0 g/dL, such as about 10.0 g/dL, 11.4 g/dL, 11.5 g/dl, 12.9 g/dL, 13.0 g/dL, or 13.4 g/dL), where the level of hemoglobin lower than the predetermined threshold indicates anemia; comparing the level of blood health index to a predetermined threshold for blood health index, where the level of blood health index either higher or lower than the predetermined threshold indicates iron-depletion or iron-deficiency; and selecting a patient care plan to treat the anemia, the iron-depletion, or the iron-deficiency; administering the patient care plan to treat the subject; selecting one or more laboratory tests, in the physical computing device, where the one or more laboratory tests are selected from the group consisting of a creatinine test (e.g., with a calculated glomerular filtration rate test), a glomerular filtration rate test, a vitamin B12 test, and a folate test; receiving a revised level of hemoglobin of the subject or a revised level of blood health index of the subject, in the physical computing device, where the revised levels are determined after the subject is treated with the patient care plan and the revised levels are determined on a continuous basis for a year (e.g., determined at least 2, 3, 4, 5, 6, 7, 8, 9, 10, 11, 12, or more times a year); applying the revised level of hemoglobin or the revised level of blood health index, in the physical computing device, to determine a revised patient care plan, where the applying includes comparing the revised level of hemoglobin to the predetermined threshold for hemoglobin, where the revised level of hemoglobin lower than the predetermined threshold indicates anemia; comparing the revised level of blood health index to the predetermined threshold, where the level of blood health index either higher or lower than the predetermined threshold indicates iron-depletion or iron-deficiency; and selecting the revised patient care plan to treat the anemia, the iron-depletion, or the iron-deficiency; and administering the revised patient care plan to treat the subject. In particular embodiments of the fourth and fifth aspect, the chronic disease is not chronic heart failure.

In further embodiments of the sixth and seventh aspects, the chronic disease is selected from the group consisting of a chronic heart failure, an inflammatory gastrointestinal disease (e.g., chronic inflammatory bowel disease or chronic autoimmune bowel disease), a rheumatologic inflammatory disease (e.g., rheumatologic diseases and autoimmune diseases), a chronic viral disease (e.g., hepatitis C infection, hepatitis B infection, or HIV infection), a chronic inflammatory state (e.g., diabetes, chronic renal disease, and obesity), a gynecological state (e.g., patients who are pregnant or have excessive uterine loss), or a post-surgical state (e.g., a patient who had bariatric surgery).

In additional embodiments of the sixth and seventh aspects, the profile further includes information regarding a health insurance plan and a health insurance provider of the subject, and where the method further includes: comparing, in the physical computing device, a medical procedure, a laboratory test, a treatment, or a medication indicated in the patient care plan with the types of medical procedure, laboratory test, treatment, or medication allowed or restricted by the health insurance plan; determining, in the physical computing device, whether coverage of the patient care plan requires pre-authorization by the subject's healthcare provider; and requesting and documenting, in the physical computing device, approval of the pre-authorization by the health insurance provider.

In any of the sixth and seventh aspects, the patient care plan includes one or more of oral iron (e.g., with or without ascorbic acid), intravenous iron (e.g., ferric carboxymaltose, iron sucrose (Venofer®), iron dextran (InFeD®)), an erythropoietic medication (e.g., erythropoietin, epoetin, epoetin alfa, darbepoetin alfa, epoetin delta, PDpoetin, or methoxy polyethylene glycol-epoetin beta), folate, vitamin B12, desmopressin acetate, or dialysis.

In further embodiments of the sixth and seventh aspects, the profile further includes information regarding current or past history of disease of the subject and glomerular filtration rate and where the level of blood health index includes one or more of level of serum iron, level of % iron saturation, level of ferritin, level of C reactive protein, mean corpuscular volume, mean corpuscular hemoglobin, level of vitamin B12, or level of folate.

In particular embodiments of the sixth and seventh aspects, the method further includes applying the profile and the level of blood health index, in the physical computing device, to determine level of renal risk, where if the history of disease includes diabetes or chronic renal disease and the level of blood health index is either more or less than the predetermined threshold, then the level of renal risk is high, and where the patient care plan for treating the high level of renal risk includes administration of one or more medication from oral iron, intravenous iron, ferric carboxymaltose, iron sucrose, iron dextran, erythropoietin, folate, vitamin B12, epoetin, epoetin alfa, darbepoetin alfa, epoetin delta, PDpoetin, and methoxy polyethylene glycol-epoetin beta.

In additional embodiments of the sixth and seventh aspects, the predetermined threshold for blood health index includes one or more of level of serum iron of about 35 µg/dL (e.g., 20 µg/dL, 25 µg/dL, 30 µg/dL, 35 µg/dL, 40

μg/dL, or 45 μg/dL), level of % iron saturation of about 25% (e.g., 15%, 20%, 25%, 30%, or 35%), level of ferritin of about 125 ng/mL (e.g., 100 ng/mL, 110 ng/mL, 115 ng/mL, 120 ng/mL, 125 ng/mL, 130 ng/mL, 135 ng/mL, or 140 ng/mL), level of C reactive protein of about 8 mg/L (e.g., 6 mg/L, 7 mg/L, 8 mg/L, 9 mg/L, or 10 mg/L), mean corpuscular volume of about 82 fL (e.g., 70 fL, 74 fL, 78 fL, 80 fL, 82 fL, 84 fL, 88 fL, 90 fL, or 92 fL) or of about 100 fL (e.g., 98 fL, 100 fL, 110 fL, 115 fL, 120 fL, 130 fL, 140 fL, 145 fL, or 150 fL), or mean corpuscular hemoglobin of about 30 pg (e.g., 24 pg, 25 pg, 28 pg, 30 pg, 32 pg, 34 pg, 35 pg, or 36 pg), and where the level of blood health index includes one or more of level of serum iron equal to or less than about 35 μg/dL (e.g., 20 μg/dL, 25 μg/dL, 30 μg/dL, 35 μg/dL, 40 μg/dL, or 45 μg/dL), level of % iron saturation equal to or less than about 25% (e.g., 15%, 20%, 25%, 30%, or 35%), level of ferritin equal to or less than about 125 ng/mL (e.g., 100 ng/mL, 110 ng/mL, 115 ng/mL, 120 ng/mL, 125 ng/mL, 130 ng/mL, 135 ng/mL, or 140 ng/mL), level of C reactive protein equal to or more than about 8 mg/L (e.g., 6 mg/L, 7 mg/L, 8 mg/L, 9 mg/L, or 10 mg/L), mean corpuscular volume equal to or less than about 82 fL (e.g., 70 fL, 74 fL, 78 fL, 80 fL, 82 fL, 84 fL, 88 fL, 90 fL, or 92 fL) and more than about 100 fL (e.g., 98 fL, 100 fL, 110 fL, 115 fL, 120 fL, 130 fL, 140 fL, 145 fL, or 150 fL), or mean corpuscular hemoglobin equal to or less than about 30 pg (e.g., 24 pg, 25 pg, 28 pg, 30 pg, 32 pg, 34 pg, 35 pg, or 36 pg).

In other embodiments of the sixth and seventh aspects, the method further includes: receiving a revised level of hemoglobin of the subject and a revised level of blood health index, in the physical computing device, where the revised levels are determined after the subject is treated with the patient care plan; applying the revised level of hemoglobin and the revised level of blood health index, in the physical computing device, to determine a revised patient care plan; and outputting the revised patient care plan to one or more of the computer readable medium, the server, the network, the display device, or the printed report.

In further embodiments of the sixth and seventh aspects, the method includes outputting a patient satisfaction outcome report, a hospital satisfaction outcome report, an adverse event outcome report, or a surgical outcome-specific report including the patient care plan, the revised patient care plan, and/or the one or more laboratory tests to one or more of the computer readable medium, the server, the network, the display device, or the printed report.

In any of the above aspects, the invention relates to a computer readable storage media including an executable code that causes a physical computing device to perform any of the methods described herein.

In an eighth aspect, the invention relates to computer readable storage media containing an executable code that causes a physical computing device to perform a method requiring the steps of: receiving data containing a profile of a subject preparing to undergo a non-emergent surgery, in the physical computing device, where the profile contains the level of hemoglobin of the subject, level of creatinine of the subject, and information regarding the current or past history of disease of the subject; applying the profile, in the physical computing device, to determine the level of transfusion risk and level of comorbidity; applying the level of hemoglobin, the level of transfusion risk, and the level of comorbidity, in the physical computing device, to determine a patient care plan; applying the profile, in the physical computing device, to determine the level of bleeding risk; applying the level of hemoglobin, the level of creatinine, and the level of bleeding risk, in the physical computing device, to determine a first test panel, where the first test panel indicates whether or not one or more laboratory tests need to be performed; and outputting the patient care plan and the first test panel to one or more of a computer, a server, a network, a display device, or a printed report.

The computer readable storage media of the invention may receive data containing a profile of a subject, which further includes the type of the non-emergent surgery and the red cell antibody information of the subject, and the executable code of the physical computing device may perform a method further requiring the steps of applying the type of the non-emergent surgery, in the physical computing device, to determine a range of anticipated loss of blood volume; applying the range of anticipated loss of blood volume and the level of comorbidity, in the physical computing device, to determine a range of tolerable loss of blood volume; applying the red blood cell antibody information, in the physical computing device, to determine one or more compatible blood types; applying the range of anticipated loss of blood volume, the range of tolerable loss of blood volume, the one or more compatible blood types, and the level of comorbidity, in the physical computing device, to determine an in-hospital transfusion minimization plan; applying the red cell antibody information, in the physical computing device, to determine a second test panel, where the second test panel indicates whether or not one or more laboratory tests need to be performed; and outputting the in-hospital transfusion minimization plan and the second test panel to one or more of the computer readable medium, the server, the network, the display device, or the printed report.

In further embodiments of the computer readable storage medium, the profile further includes information regarding a health insurance plan and a health insurance provider of the subject, and the method further includes: comparing a medical procedure, a laboratory test, a treatment, or a medication indicated in the patient care plan, the in-hospital transfusion minimization care plan, the first test panel, and/or the second test panel with the types of medical procedure, laboratory test, treatment, or medication allowed or restricted by the health insurance plan; determining whether coverage of the patient care plan, the in-hospital transfusion minimization care plan, the first test panel, and/or the second test panel requires pre-authorization by the subject's healthcare provider; requesting and documenting approval of the pre-authorization by the health insurance provider; and outputting the results of the comparing, determining, requesting, and documenting steps to one or more of the computer readable medium, the server, the network, the display device, or the printed report.

The computer readable storage media, as described above, may receive data containing a profile of a subject, which further includes the weight, gender, age, date of the non-emergent surgery, information regarding whether the non-emergent surgery is a redo procedure, and information regarding whether the non-emergent surgery is a non-isolated procedure; and the executable code of the physical computing device applies the profile to determine the level of transfusion risk by the steps of: applying the level of hemoglobin to determine a first value, where if the level of hemoglobin is between 10.0 g/dL-11.4 g/dL (e.g., or between 10.0 g/dL-11.5 g/dL), then the first value is two, where if the level of hemoglobin is above 11.4 g/dL and below 13.0 g/dL (e.g., between 11.5 g/dL-12.9 g/dL or alternatively between 11.5 g/dL-13.4 g/dL), then the first value is one, and where if the level of hemoglobin is more than or equal to 13.0 g/dL (e.g., or more than or equal to 13.5 g/dL), then the first value is zero; applying the weight to determine a second value, where if the weight is less than 50 kg, then the second value is two, where if the weight is between 50 kg-75 kg, then the second value is one, and where if the weight is more than 75 kg, then the second value is zero; applying the gender to determine a third value, where if the gender is female, then the third value is one, and where if the gender is male, then the third value is zero; applying the age to determine a fourth value, where if the age is more than or equal to 65 years, then the fourth value is one, and where if the age is less than 65 years, then the fourth value is zero; applying the date of the non-emergent surgery to determine a fifth value, where if the date of the non-emergent surgery is less than two weeks away, then the fifth value is one, and where if the date of the non-emergent surgery is more than or equal to two weeks away, then the fifth value is zero; applying the level of creatinine to determine a sixth value, where if the level of creatinine is more than or equal to 2.0 mg/dL, then the sixth value is two, where if the level of creatinine is between 1.2 mg/dL-1.9 mg/dL, then the sixth value is one, and where if the level of creatinine is less than 1.2 mg/dL, then the sixth value is zero; applying the information regarding whether the non-emergent surgery is a redo procedure to determine a seventh value, where if the non-emergent surgery is a redo procedure, then the seventh value is one, and where if the non-emergent surgery is not a redo procedure, then the seventh value is zero; applying the information regarding whether the non-emergent surgery is a non-isolated procedure to determining an eighth value, where if the non-emergent surgery is a non-isolated procedure, then the eighth value is one, where if the non-emergent surgery is an isolated procedure, then the eighth value is zero; and outputting the level of transfusion risk to one or more of the computer readable medium, the server, the network, the display device, or the printed report where if the sum of the first value to the eighth value is less than or equal to one, then the level of transfusion risk is low, if the sum of the first value to the eighth value is two, then the level of transfusion risk is intermediate, if the sum of the first value to the eighth value is three, then the level of transfusion risk is high, and if the sum of the first value to the eighth value is three, then the level of transfusion is high, and if the sum of the first value to the eighth value is more than three, then the level of transfusion risk is very high; and where applying the profile, in the physical computing device, to determine the level of comorbidity includes applying the information regarding current or past history of disease to determine the level of comorbidity, where if the information regarding current or past history of disease contains past history of cardiovascular disease, cerebrovascular disease, pulmonary disease, renal disease, cancer, autoimmune disease, gastrointestinal disease, inflammatory disease, active infection, or blood clotting disorder, then the level of comorbidity contains one or more comorbid conditions.

In additional embodiments of the computer readable storage media, as described above, applying of the level of hemoglobin, the level of transfusion risk, and the level of comorbidity, in the physical computing device, to determine the patient care plan includes the steps of: determining whether the level of hemoglobin results in the first value being one or zero; determining whether the level of transfusion risk is low, intermediate, high, or very high; determining whether the level of comorbidity contains one or more comorbid conditions; and selecting the patient care plan based on the level of hemoglobin, the level of transfusion risk, and the one or more comorbid conditions, where if the first value is zero, the level of transfusion risk is low or intermediate, and the one or more comorbid conditions are not present, then the patient care plan includes one or more of oral iron or a multivitamin; if the one or more comorbid conditions are present, then the patient care plan includes one or more of an erythropoietic medication, intravenous iron, oral iron, desmopressin acetate, preoperative dialysis, preoperative coagulation therapy, or preoperative autologous blood donation; and if the first value is one or the level of transfusion risk is high or very high, then the patient care plan includes one or more of intravenous iron, cell saver, preoperative autologous blood donation, postoperative iron, or use of pediatric blood tubes for blood draws.

The computer readable storage media, as described above, may receive data containing a profile of a subject, which further contains information regarding medication taken by the subject, and where applying the level of hemoglobin, the level of transfusion risk, and the level of comorbidity, in the physical computing device, to determine the patient care plan may further require: applying the information regarding medication taken by the subject to determine a ninth value, where if the information regarding medication taken by the subject contains one or more anticoagulant medications, then said ninth value is positive; and applying the ninth value to further determine the patient care plan, where if the ninth value is positive, then the patient care plan further includes the discontinuation of the one or more anticoagulant medications between about one week to about two weeks (e.g., about one week) before the date of the non-emergent surgery.

The computer readable storage media, as described above, when applying the level of hemoglobin, the level of transfusion risk, and the level of comorbidity, in the physical computing device, to determine the patient care plan may further require: applying the date of the non-emergent surgery to determine a tenth value, where if the date of the non-emergent surgery is more than one week away, then the tenth value is zero; and applying the first value and the tenth value to further determine the patient care plan, where if the first value is positive (e.g., one, two, or any positive integer) and the tenth value is zero, then the patient care plan further includes one or more of iron (e.g., oral iron with or without ascorbic acid or intravenous iron, such as ferric carboxymaltose, iron sucrose (Venofer®), iron dextran (InFeD®)), ascorbic acid, vitamin B12, folate, or an erythropoietic medication (e.g., erythropoietin, folate, vitamin B12, epoetin, epoetin alfa, darbepoetin alfa, epoetin delta, PDpoetin, and methoxy polyethylene glycol-epoetin beta).

In addition, the computer readable storage media, as described above, may cause a physical computing device to perform a method that further includes the steps of: receiving data containing a revised level of hemoglobin of the subject, where the revised level of hemoglobin is determined after the subject is treated with the patient care plan; receiving data containing a revised profile of the subject, where the revised profile is determined after the subject is treated with the patient care plan; applying the revised level of hemoglobin and the revised profile, in the physical computing device, to determine a revised level of transfusion risk; applying the revised level of hemoglobin and the revised level of transfusion risk, in the physical computing device, to determine a revised patient care plan; and outputting the revised level of hemoglobin and the revised patient care plan to one or more of the computer readable medium, the server, the network, the display device, or the printed report.

In additional embodiments of the computer readable storage media, as described above, the revised profile further contains revised weight, gender, revised age, revised date of the non-emergent surgery, revised level of creatinine, revised information regarding whether the non-emergent surgery is a redo procedure, and revised information regarding whether the non-emergent surgery is a non-isolated procedure.

In other embodiments of the computer readable storage media, as described above, the profile further contains information regarding medication taken by the subject, and where applying the profile, in the physical computing device, to determine the level of bleeding risk includes the steps of: applying the information regarding current or past history of disease to determine an eleventh value, where if the information regarding current or past history of disease contains past history of bleeding, then the eleventh value is positive; and applying the information regarding medication taken by the subject to determine a twelfth value, where if the information regarding medication taken by the subject contains one or more procoagulant medications, then the twelfth value is positive; and if one or more of the eleventh value to the twelfth value are positive, then the level of bleeding risk is high.

In additional embodiments of the computer readable storage media, as described above, applying of the level of bleeding risk, in the physical computing device, to determine the first test panel includes: using the eleventh value and twelfth value to determine the level of bleeding risk; and selecting one or more laboratory tests if the level of bleeding risk is high, where the one or more laboratory tests are selected from the group of a screening coagulation panel and a special coagulation test.

In other embodiments of the computer readable storage media, as described above, applying of the level of hemoglobin and the level of creatinine, in the physical computing device, to determine the first test panel includes the steps of: applying the level of hemoglobin to determine whether the subject is anemic or whether the level of hemoglobin has been determined recently; selecting the one or more laboratory tests if the subject is anemic or if the level of hemoglobin is not recent, where the one or more laboratory tests are selected from the group of an iron assessment panel, a complete blood count, a hemoglobin test, a vitamin B12 test, and a folate test; applying the level of creatinine to determine whether the level of creatinine has been determined recently; and selecting the one or more laboratory tests if the level of creatinine is not recent, where the one or more laboratory tests are selected from the group of a creatinine test (e.g., with calculated glomerular filtration rate) and a blood urea nitrogen test.

In additional embodiments of the computer readable storage media, as described above, applying of the level of comorbidity, in the physical computing device, to determine an in-hospital transfusion minimization plan includes the steps of: determining whether the level of comorbidity includes one or more comorbid conditions; and selecting a transfusion product based on the level of comorbidity, where if the one or more comorbid conditions are present, then the transfusion product has a higher than physiological range of hemoglobin or has a shelf age of less than 14 days.

In further embodiments, the computer readable storage media, as described above, the applying of the red cell antibody information, in the physical computing device, to determine the second test panel includes the steps of: applying the red cell antibody information to determine whether one or more red cell antibodies are present; and selecting one or more laboratory tests if the one or more red cell antibodies are present, where the one or more laboratory tests are selected from the group of a red cell antibody identification test, a direct antiglobulin test, an indirect antiglobulin test, and a blood typing test. In further embodiment, the method further includes outputting the results of the one or more laboratory tests if one or more red cell antibodies are present, and providing the results to a healthcare provider to ensure that blood components compatible with the one or more red cell antibodies are available for transfusion during the non-emergent surgery.

In additional embodiments of the computer readable storage media, as described above, the method further includes: applying the information regarding current or past history of disease, in the physical computing device, to determine level of renal risk, where if the information regarding current or past history of disease contains current or past history of renal disease or current or past history of diabetes, then the level of renal risk is high; applying the level of renal risk, in the physical computing device, to determine a third test panel, where the third test panel indicates whether or not one or more laboratory tests need to be performed, and where if the level of renal risk is high, then the third test panel contains one or more of a creatinine test (e.g., with calculated glomerular filtration rate) or a blood urea nitrogen test; and outputting the third test panel to one or more of the computer readable medium, the server, the network, the display device, or the printed report. In further embodiments, if the level of renal risk is high, then the patient care plan further includes a consultation with a renal specialist, and where if the level of creatinine is more than 2 mg/dL, then the patient care plan further includes dialysis.

In further embodiments of the computer readable storage media, as described above, the method further includes the steps of: receiving data of the subject after undergoing the non-emergent surgery, where the data of the subject after undergoing the non-emergent surgery contains information regarding loss of blood volume during the non-emergent surgery, information regarding whether the subject had a transfusion during the non-emergent surgery, and information regarding adverse events; applying the data of the subject after undergoing the non-emergent surgery, the profile, the level of transfusion risk, the level of comorbidity, the patient care plan, and the in-hospital transfusion minimization plan, in the physical computing device, to determine a patient outcome report; and outputting the patient outcome report to one or more of the computer readable medium, the server, the network, the display device, or the printed report.

In particular embodiments of the computer readable storage media, as described above, the method further includes outputting a patient satisfaction outcome report, a hospital satisfaction outcome report, an adverse event outcome report, or a surgical outcome-specific report comprising the patient care plan, the in-hospital transfusion minimization care plan, the revised patient care plan, the first test panel, the second test panel, and/or the third test panel to one or more of a computer readable medium, a server, a network, a display device, or a printed report.

The invention further provides physical computing devices including a processor, a memory, and an interconnection mechanism coupling the processor and the memory, where the memory contains data and an executable code that causes the processor to perform any methods described herein.

The invention further provides physical computing devices including any computer readable storage media described herein.

In any of the methods and computer readable storage media described herein, the non-emergent surgery is either a high blood loss surgery, such as knee replacement surgery (e.g., single or bilateral surgeries, or total or partial knee replacement surgery (primary or revision)), total hip joint arthroplasty (also known as total hip replacement surgery (primary or revision)), or spine surgery (e.g., involving three or more vertebras); cardiovascular surgery, such as valve surgery (e.g., cardiac valve replacement or cardiac valve repair), coronary artery bypass surgery (e.g., with or without cardiac valve repair or replacement), or aortic replacement surgery; genitourinary surgery (e.g., radical retropubic prostatectomy or cystectomy); gastrointestinal surgery, such as to treat cancer (e.g., esophagectomy, gastrectomy, or colectomy) or inflammatory bowel disease (e.g., colectomy); other vascular surgery (e.g., aneurysm repair); gynecology surgery, such as gynecological oncology surgery or uterine cancer surgery (e.g., hysterectomy with or without bilateral salpingo-oophorectomy, tumor debulking, omentectomy, and lymph node sampling); neurosurgery (e.g., meningioma resection or surgery to correct vascular malformations); an oncologic thoracic surgery (e.g., removal of lung tumors); a high-risk cesarean delivery; or any combination thereof; or a low blood loss surgery in a patient population with high anemia prevalence, such as a benign gynecologic surgery performed to ameliorate symptoms from blood loss and anemia (e.g., hysterectomy, myomectomy for leiomyomata, or hysterectomy for endometrial abnormalities including hyperplasia or polyps).

In any of the methods and computer readable storage media described herein, the chronic disease is one or more disease selected from chronic heart failure, an inflammatory gastrointestinal disease (e.g., chronic inflammatory bowel disease or chronic autoimmune bowel disease), a chronic inflammatory disease (e.g., rheumatologic disease or autoimmune disease), a chronic viral disease (e.g., hepatitis C infection, hepatitis B infection, or HIV infection), a chronic inflammatory state (e.g., diabetes, chronic renal disease, or obesity), a gynecological state (e.g., patients who are pregnant or have excessive uterine loss), and a post-surgical state (e.g., a patient who had bariatric surgery).

In any of the methods and computer readable storage media described herein, the profile includes one or more level of hemoglobin; level of creatinine; red cell antibody information; information regarding current and past history of disease, such as current and past history of anemia, autoimmune disease, bleeding (including a history of any bleeding disorder, e.g., history of coagulopathy, a blood clotting disorder, excessive bleeding, excessive clotting, etc.), cancer, cardiovascular disease (e.g., angina, myocardial infarction, valve disease, arrhythmia), cerebrovascular disease (e.g., stroke or transient ischemic attack), diabetes, gastrointestinal disease, infection (e.g., active infection), inflammatory disease, renal disease (e.g., renal failure), pulmonary disease (e.g., chronic obstructive pulmonary disease or pulmonary fibrosis), or previous surgeries; information regarding medication taken by said subject, such as one or more of anticoagulant medications (e.g., heparin, warfarin (Coumadin), clopidogrel (Plavix®), dong quoi, bromelain, chamomile, dandelion root, garlic, ginger, gingko biloba, St. John's wort, or vitamin C), procoagulant medications (e.g., a zeolite, desmopressin, a coagulation factor, such as factor VII, tranexamic acid, aminocaproic acid, or aprotinin), insulin, or erythropoietic medications (e.g., erythropoietin, epoetin, epoetin alfa, darbepoetin alfa, epoetin delta, PDpoetin, and methoxy polyethylene glycol-epoetin beta); subject demographics, such as height, weight, gender, date of birth, or age; information regarding the subject's lifestyle habits, such as diet, exercise, tobacco use, or alcohol use; date of said non-emergent surgery; type of non-emergent surgery; information regarding whether said non-emergent surgery is a redo procedure; or information regarding whether said non-emergent surgery is non-isolated, such as a bilateral knee surgery that requires both knees to be operated or a combination of a coronary artery bypass and valve surgery being scheduled at the same time.

In any of the methods and computer readable storage media described herein, the profile can further include information of a blood health index, for example, a level determined by one or more of laboratory tests selected from the group of complete blood count (e.g., with reticulocyte count, platelet count, white blood cell (WBC) count, red blood cell (RBC) count, a hemoglobin (Hgb) test, a hematocrit (Hct) test, mean corpuscular volume (MCV), mean corpuscular hemoglobin (MCH), mean corpuscular hemoglobin concentration (MCHC), red cell distribution width (RDW), and reticulocyte hemoglobin concentration), complete iron studies or an iron assessment panel (e.g., serum iron, transferrin, % iron saturation (or % saturation of transferrin by iron), total iron binding capacity, and ferritin), a hemoglobin (Hgb) test, a vitamin B12 test, a folate test, a reticulocyte count, a platelet count, a WBC count, serum iron, iron binding capacity, % iron saturation (or % saturation of transferrin by iron), a ferritin assay, a C reactive protein (non-cardiac, inflammatory) assay, a creatinine test, a glomerular filtration rate (GFR) test, a creatinine test with calculated GFR, a blood urea nitrogen test, a methylmalonic acid (MMA) test, a transferrin assay, a soluble transferrin receptor assay, a hepcidin assay, an interleukin-6 assay, and an epoetin or erythropoietin test. In further embodiments, the blood health index includes one or more assessments for quality of life and physical function, such as heart failure-specific questionnaires (e.g., the Minnesota Living with Heart Failure Questionnaire (MLWHFQ) or the Kansas City Cardiomyopathy Questionnaire (KCCQ)), general quality of life questionnaires (e.g., a Patient Global Assessment test or European Quality of Life-5 Dimensions test), and a heart function test (e.g., the 6 minute walk test or the New York Heart Association functional class).

In any of the methods and computer readable storage media described herein, the patient care plan includes one or more of oral iron (e.g., with or without ascorbic acid), intravenous iron (e.g., ferric carboxymaltose, iron sucrose, or iron dextran), an erythropoietic medication (e.g., erythropoietin, epoetin, epoetin alfa, darbepoetin alfa, epoetin delta, PDpoetin, or methoxy polyethylene glycol-epoetin beta), folate, vitamin B12, desmopressin acetate, preoperative dialysis, preoperative coagulation therapy, preoperative autologous blood donation, cell saver, postoperative iron (e.g., postoperative oral iron (with or without ascorbic acid) or intravenous iron, such as ferric carboxymaltose, iron sucrose, and iron dextran), use of pediatric blood tubes for blood draws, and/or discontinuation of one or more anticoagulant medications between about one week to about two weeks before the date of the non-emergent surgery.

In any of the methods and computer readable storage media described herein, the in-hospital transfusion minimization plan may include use of a transfusion product having a shelf age of less than 14 days or having a higher than physiological range of hemoglobin.

In any of the methods and computer readable storage media described herein, the patient care plan is a blood health treatment plan (e.g., treatment with one or more of oral iron with or without ascorbic acid; intravenous iron, such as ferric carboxymaltose, iron sucrose, and iron dextran; ascorbic acid; folate; vitamin B12; or an erythropoietic medication, such as erythropoietin, epoetin, epoetin alfa, darbepoetin alfa, epoetin delta, PDpoetin, and methoxy polyethylene glycol-epoetin beta), as defined herein. In particular embodiments, the blood health treatment plan includes erythropoietin and one of oral iron, intravenous iron, ferric carboxymaltose, iron sucrose, iron dextran, ascorbic acid, folate, and vitamin B12. In other embodiments, the blood health treatment plan includes epoetin alfa and one of oral iron, intravenous iron, ferric carboxymaltose, iron sucrose, iron dextran, ascorbic acid, folate, and vitamin B12.

In any of the methods and computer readable storage media described herein, the method further includes managing the subject though notification and support in the physical computing device.

In further embodiments of any of the methods and computer readable storage media described herein, the steps are performed in a physical computing device or the steps are encoded in executable code to be performed in said physical computing device.

DEFINITIONS

By "adverse events" is meant one or more undesired changes in a subject's health before, during, or after a non-emergent surgery.

By "anticoagulant medication" is meant one or more medications that decrease or prevent clotting of blood.

By "applying" is using information from a subject, a healthcare provider, a health insurance provider, or a database, in a blood health management program to determine a prediction of risk, a patient care plan, an in-hospital transfusion minimization care plan, or an outcome report, as described herein.

By "blood draw" is meant a procedure to obtain blood from a subject.

By "blood health index" is meant a level of a chemical or biological analyte in a blood sample determined by a laboratory test or a level of quality life determined by a scoring tool and/or a functional, physical test.

By "blood health treatment plan" is meant a care plan for treatment of anemia or, for subject having chronic heart failure, treatment of iron-depletion with or without anemia.

By "chronic disease" is meant a recurrent disease having underlying symptoms related to anemia, iron-depletion, or iron-deficiency.

By "continuous basis" is meant performing a laboratory test and/or administering a treatment to a subject at least 2 times a year (e.g., 3, 4, 5, 6, 7, 8, 9, 10, 11, 12, or more times a year).

By "continuously treating" is meant a treatment, as described herein, that is administered to a subject at least 2 times a year (e.g., 3, 4, 5, 6, 7, 8, 9, 10, 1, 12, or more times a year).

By "comorbid condition" or "comorbidity" is meant a disease or condition of a subject, other than the primary disease of interest, that could affect the subject's morbidity, mortality, or surgical outcome.

By "erythropoietic medication" is meant one or more medications that increases erythropoiesis.

By "healthcare provider" is meant a person or entity that provides, facilitates, or coordinates medical care for a subject. Exemplary healthcare providers include any hospital staff member, such as a physician (e.g., primary care physician (PCP), a specialist, a surgeon, or a hematologist), a nurse, a nurse's assistant, a physician's assistant (PA); a hospital administrator; a support staff member; or a hospital.

By "health insurance plan" is meant a subject's policy providing information for allowed and restricted medical procedures, laboratory tests, treatments, or medications. Exemplary information includes allowed and not allowed treatments; restricted medical procedures, laboratory tests, treatments, or medications that require preauthorization; allowed or not allowed medications; and "rules" of use of medications, where certain therapeutic agents are used as first line therapy and failure must be documented before other medications can be used.

By "health insurance provider" is meant a person or entity that provides health insurance coverage for the subject.

By "in-hospital transfusion minimization care plan" is meant to a plan for avoiding an unnecessary or excessive transfusion, for determining when a transfusion would be necessary, or for administering a transfusion product to a subject during or after a non-emergent surgery.

By "level of bleeding risk" is meant a prediction of risk that a subject on procoagulant medication, with history of bleeding condition, and/or with documented renal disease will experience loss of blood during or after a non-emergent surgery.

By "level of comorbidity" is meant a prediction of risk that a subject will have complications based on the presence of one or more diseases. Exemplary diseases include one or more comorbid conditions, as described herein.

By "level of renal risk" is meant a prediction of risk that a subject will experience renal dysfunction or failure during or after a non-emergent surgery.

By "level of transfusion risk" is meant a prediction of risk that a subject will need a transfusion during or after a non-emergent surgery.

By "non-emergent surgery" is meant a scheduled surgical procedure. The surgical procedure is typically scheduled in advance of the date of surgery by any number of days (e.g., more than one day, three days, one week, or two weeks away).

By "non-isolated procedure" is meant that more than one surgical procedure is being performed on a subject.

By "patient care plan" or "care plan" is meant a preoperative, intraoperative (or in-hospital), or postoperative plan for administering a treatment, as described herein, to a subject. Examples of care plans include a preoperative blood health preparedness ("BHP") care plan or an in-hospital transfusion minimization ("TM") care plan.

By "patient outcome report" is meant a report about the subject before, during, and after the non-emergent surgery; before, during, and after treatment for anemia for a subject having a chronic disease; or before, during, and after treatment for iron depletion in a subject having chronic heart failure.

By "physiological range" is meant a normal concentration range of a particular component within a subject.

By "predetermined comorbid condition" is meant one or more conditions that indicate an increased risk of comorbidity before, during, or after the non-emergent surgery.

By "predetermined bleeding risk condition" is meant one or more conditions that indicate an increased risk of bleeding during or after the non-emergent surgery.

By "predetermined threshold" is meant a cut-off value or a cut-off range of values that indicate an increased risk for a transfusion or for a diagnosis of anemia, iron-depletion, or iron-deficiency.

By "procoagulant medication" is meant one or more medications that increases or promotes clotting of blood.

By "profile" is meant information relating to a subject who is preparing to undergo a non-emergent surgery or who has a chronic disease and is being evaluated and treated, if necessary, for anemia, iron-depletion, or iron-deficiency.

By "revised," when used in conjunction with another term, is meant that the term was determined after a subject has undergone a preoperative treatment or after a subject has been treated for anemia, iron-deficiency, or iron-depletion. For example, by "revised profile" is meant a profile, as defined herein, that is determined after a subject has undergone a preoperative treatment, such as treatment of anemia.

By "range of anticipated loss of blood volume" is meant a predicted range of the volume of blood that a subject will likely lose during or after a non-emergent surgery.

By "range of tolerable loss of blood volume" is meant a predicted range of the volume of blood that a subject can lose during or after a non-emergent surgery without serious health consequences.

By "redo procedure" is meant that a surgical procedure has been performed before and that a later procedure repeats that previous surgical procedure.

By "subject" or "patient" is meant a mammal undergoing a non-emergent surgery or having a chronic disease.

By "test panel" is meant a group of one or more laboratory tests that has been or will be performed on a bodily fluid or tissue sample from a subject.

By "transfusion management healthcare provider" is meant a healthcare provider that provides, facilitates, or coordinates care for a subject by implementing a transfusion minimization protocol, as described herein.

By "transfusion product" is meant a composition infused into a subject to treat any one or all of (1) red cell loss; (2) low or dysfunctional platelets; or (3) non-platelet regulated coagulation abnormalities.

By "treatment" is meant an approach for obtaining beneficial or desired results in a subject. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment.

By "value" is meant a variable that can be assigned to one or more results. Examples of values include integer numbers (e.g., 2, 1, 0, −1, and −2), decimal numbers (e.g., 1.1, 1.2, or 1.3), and answers to decision problems (e.g., yes and no; or affirmative and negative; or positive, such as any positive integer number, and zero).

By "computer readable medium" is meant any component capable of containing, storing, communicating, propagating, or transporting one or more of executable code or data.

By "computer readable storage medium" is meant any computer readable medium capable of storing data, e.g., executable code.

By "data" is meant any information in any language capable of being used by or in connection with a physical computing device, such as a computer.

By "executable code" is meant a set of instructions in any language capable of being used by or in connection with a physical computing device, such as a computer.

By "display device" is meant any component capable of digitally, electronically, or visually displaying a result.

By "interconnection mechanism" is meant a component that couples two or more other components of a physical computing device.

By "memory" is meant any computer readable medium capable of storing data and/or executable code.

By "network" is meant two or more physical computing devices connected through any type of communications line or communications protocol.

By "output" is meant to transfer, transmit, or display one or more of information, data, executable code, or any result from executing an executable code.

By "printed report" is meant a report that is printed electronically, optically, or physically.

By "processor" is meant a component capable of performing a method encoded by an executable code.

By "receive" is meant to accept, retrieve, or obtain one or more of information, data, executable code, or any result from executing an executable code.

By "server" is meant a device or machine that serves a network.

The recitation herein of numerical ranges by endpoints is intended to include all numbers subsumed within that range (e.g., a recitation of "1-5" or "between 1-5" includes 1, 1.5, 2, 2.75, 3, 3.80, 4, and 5), unless the context clearly dictates otherwise.

As used herein, "a" or "an" means at least one or one or more unless otherwise indicated. In addition, the singular forms "a," "an," and "the," include plural referents unless the context clearly dictates otherwise.

Other features and advantages of the invention will be apparent from the following description and the claims.

BRIEF DESCRIPTION OF THE DRAWINGS

FIGS. 7B-7D shows non-limiting method for determining a BHP care plan for a subject having a chronic disease, where these methods are based on level of renal risk as measured by glomerular filtration rate (GFR) (FIG. 7B), blood health index (FIG. 7C), revised level of hemoglobin or blood health index (FIG. 7D), or revised renal risk (FIG. 7E).

FIGS. 9-1 to 9-4 are flowcharts of a non-limiting embodiment for implementing a BHP protocol.

DETAILED DESCRIPTION

In general, the invention provides methods for reducing transfusions during or after surgery, including computer readable storage media and physical computing devices for carrying out these methods. The invention also provides methods for treating a subject preparing to undergo non-emergent surgery. In particular, the invention provides a preoperative blood health preparedness protocol and an in-hospital transfusion minimization protocol to reduce transfusions during or after a non-emergent surgery, as well as a program evaluation protocol to generate reports regarding the effectiveness of these preoperative and in-hospital protocols. The methods in the invention that pertain to identifying anemia, its cause, and its proper treatment (e.g., using the blood health preparedness protocol) can be applied to identify and treat anemia, iron-depletion, or iron-deficiency in non-surgical patients, particularly those having a chronic disease with active inflammatory mediators (e.g., chronic heart failure, chronic autoimmune and inflammatory bowel disease, chronic viral infection, and chronic diabetes).

In particular, the present invention provides methods of reducing transfusion during or after surgery, as well as a computer readable storage medium and a physical computing device for carrying out these methods. The invention also relates to methods of evaluating and treating a subject preparing to undergo surgery, as well as use of data gathered from these methods in hospital spaces and outpatient spaces.

The present invention has further applications apart from mitigating the use of transfusions. The evaluative and treatment-related methodologies (e.g., as captured by the computer readable storage medium) can also be used to identify significant subpopulations having chronic heart failure (CHF) or other chronic inflammatory disease patients (e.g., patients having a chronic viral infection, autoimmune disease, inflammatory bowel disease, or diabetes). These subpopulations may not be at risk for transfusion but may have elemental deficiency states (e.g., anemia, iron-depletion, and/or iron-deficiency), and correction of these deficiency states can improve quality of life and functional capacity of a patient having a chronic disease. Accordingly, the invention further relates to methods of treating a chronic condition, as well as a computer readable storage medium and a physical computing device for carrying out these methods.

Blood Health Management Program

Figure 1A:
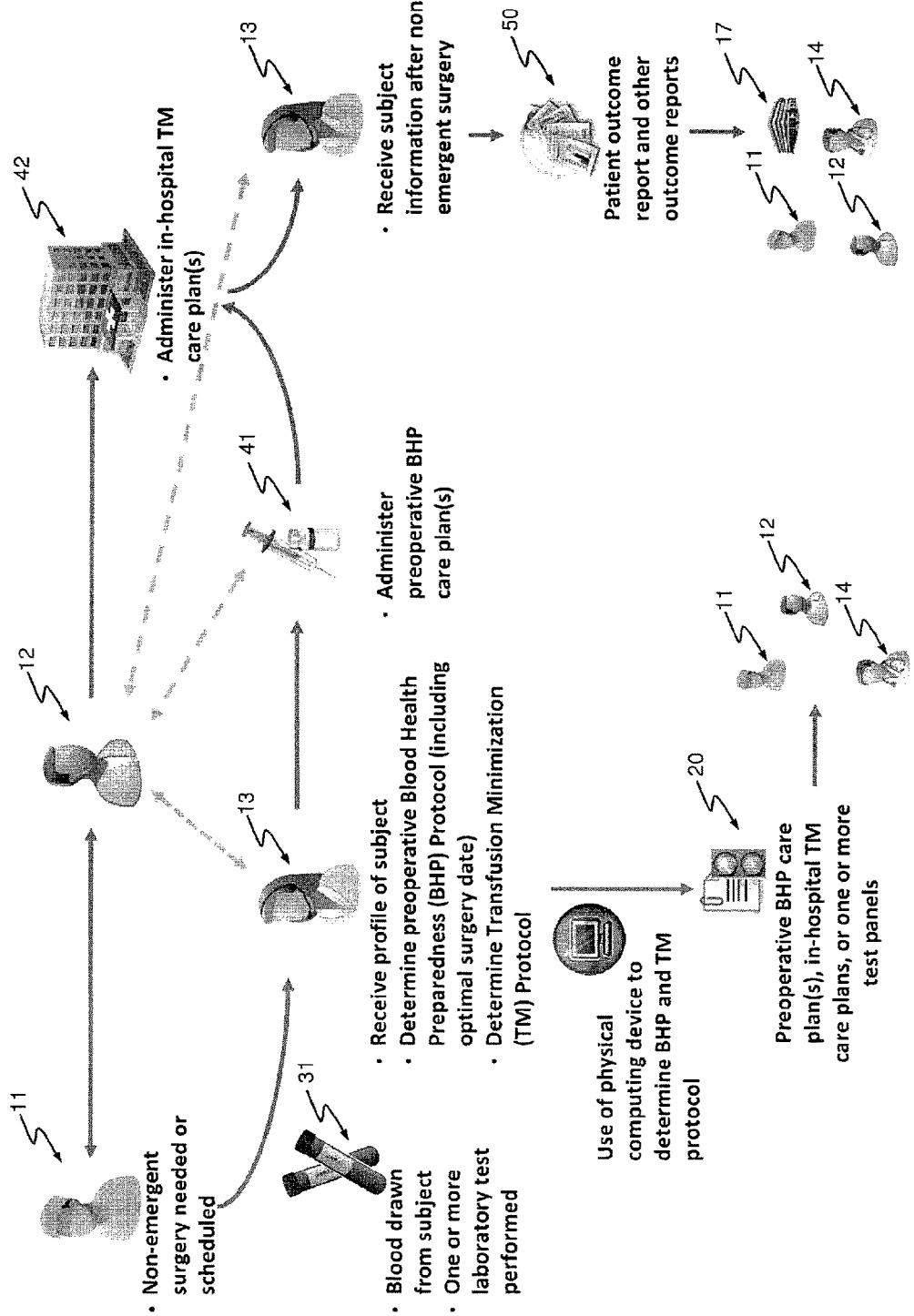
FIGS. 1A-1B are block diagrams generally showing two embodiments of implementing a blood health management program.

FIG. 1A is a block diagram generally showing one embodiment of implementing the blood health management program. The subject's healthcare provider (e.g., a surgeon) 11 schedules a non-emergent surgery for the subject 12. Then, the subject's blood is drawn 31 and one or more laboratory tests are performed on the blood sample. After the scheduling of the non-emergent surgery, a transfusion management healthcare provider 13 is contacted to evaluate the surgery date and need for pre-operative treatment protocols or in-hospital transfusion minimization plans. The transfusion management healthcare provider can also determine the patient's needs using a physical computing device to apply the program, such as by inputting and manipulating information or data in a physical computing device having executable code for performing the program.

The transfusion management healthcare provider 13 can be contacted in any way. For example, a hospital employee can personally contact the transfusion management healthcare provider; a computer system can be programmed to automatically notify the transfusion management healthcare provider when a patient has been identified as needing evaluation (e.g., when surgical need has been determined) and/or if a surgery is scheduled; or a computer system can be programmed to prompt the hospital employee to notify or contact the transfusion management healthcare provider regarding the surgery. A hospital employee includes any person employed by the subject's hospital, such as a hospital staff member (e.g., a primary care physician (PCP), a surgeon, a nurse, a nurse's assistant, or a physician's assistant (PA)); a hospital administrator; or a support staff member.

After being contacted, the transfusion management healthcare provider 13 receives a profile of the subject. When complete, the profile can include personal patient history (e.g., in an intake questionnaire format for medical and demographics information) and laboratory test results. This profile can be received from the healthcare provider's office or from the subject (as indicated by dotted line between subject 12 and transfusion management healthcare provider 13), such as through a patient questionnaire. The profile can be received from the subject in any manner, such as by interview over the phone or by filling out a questionnaire that is transmitted to the transfusion management healthcare provider. Then, the profile can be outputted by the physical computing device to the transfusion management healthcare provider.

Based on the profile, the transfusion management healthcare provider determines the blood health preparedness ("BHP") protocol and the transfusion minimization ("TM") protocol, which results in outputting one or more of preoperative BHP care plan(s) (e.g., one or more of a preoperative BHP baseline plan or preoperative BHP special care plan(s)), in-hospital transfusion minimization care plan(s), or one or more test panels 20. The preoperative BHP care plan(s), in-hospital transfusion minimization care plan(s), or one or more test panels 20 are then transferred, transmitted, sent, or communicated to one or more of the surgeon 11, the hospital employee 14, or the subject 12.

The subject's healthcare provider (e.g., a surgeon or a primary care physician), administers the preoperative BHP care plan(s) to the subject 41. The patient care plan(s) can be administered at any useful time, such as one or more of preoperatively, intraoperatively, or postoperatively; and at any useful place, such as at the subject's home, hospital, clinic, infusion center, or retail clinic. The subject's surgeon administers the in-hospital transfusion minimization ("TM") care plan(s) to the subject 42. The in-hospital TM care plan(s) can be administered intraoperatively or on the following days after the non-emergent surgery.

The test panel can either indicate that no laboratory tests are needed or indicate that one or more laboratory tests are needed. Alternatively, the one or more test panels can include laboratory tests that have already been performed or that should be performed on blood from the subject. The laboratory tests can be performed 31 by any party, including primary parties, such as by the hospital requesting the patient care plan(s) or by the transfusion management healthcare provider's in-house laboratory; or third parties, such as by a national laboratory or by a professional blood testing laboratory.

After administering the blood health management program with preoperative BHP and in-hospital TM care plans, a patient outcome report 50 can be further determined. As shown in FIG. 1A, the transfusion management healthcare provider 13 receives information regarding the subject after undergoing the non-emergent surgery. Using this information, which has been inputted in the physical computing device, a patient outcome report 50 can be generated and then transferred, transmitted, sent, or communicated to one or more of the surgeon 11, subject 12, hospital employee 14, or health insurance provider 17.

The patient outcome report includes subject-specific information, and can optionally include other hospital-specific or diagnosis-related group (DRG)-specific information. Other types of outcome reports can also be determined 50, such as a patient satisfaction outcome report, a hospital satisfaction outcome report, an adverse event outcome report, or a surgical outcome-specific report. These reports are not specific to the subject, who is de-identified in compliance with HIPAA regulations, but relate generally to the surgeon, surgeon's practice group, hospital proper, residing state of the hospital, region of the hospital (e.g., region V is the Midwest of the U.S.), or DRG. More details about outcome reports are described herein.

Figure 1B:
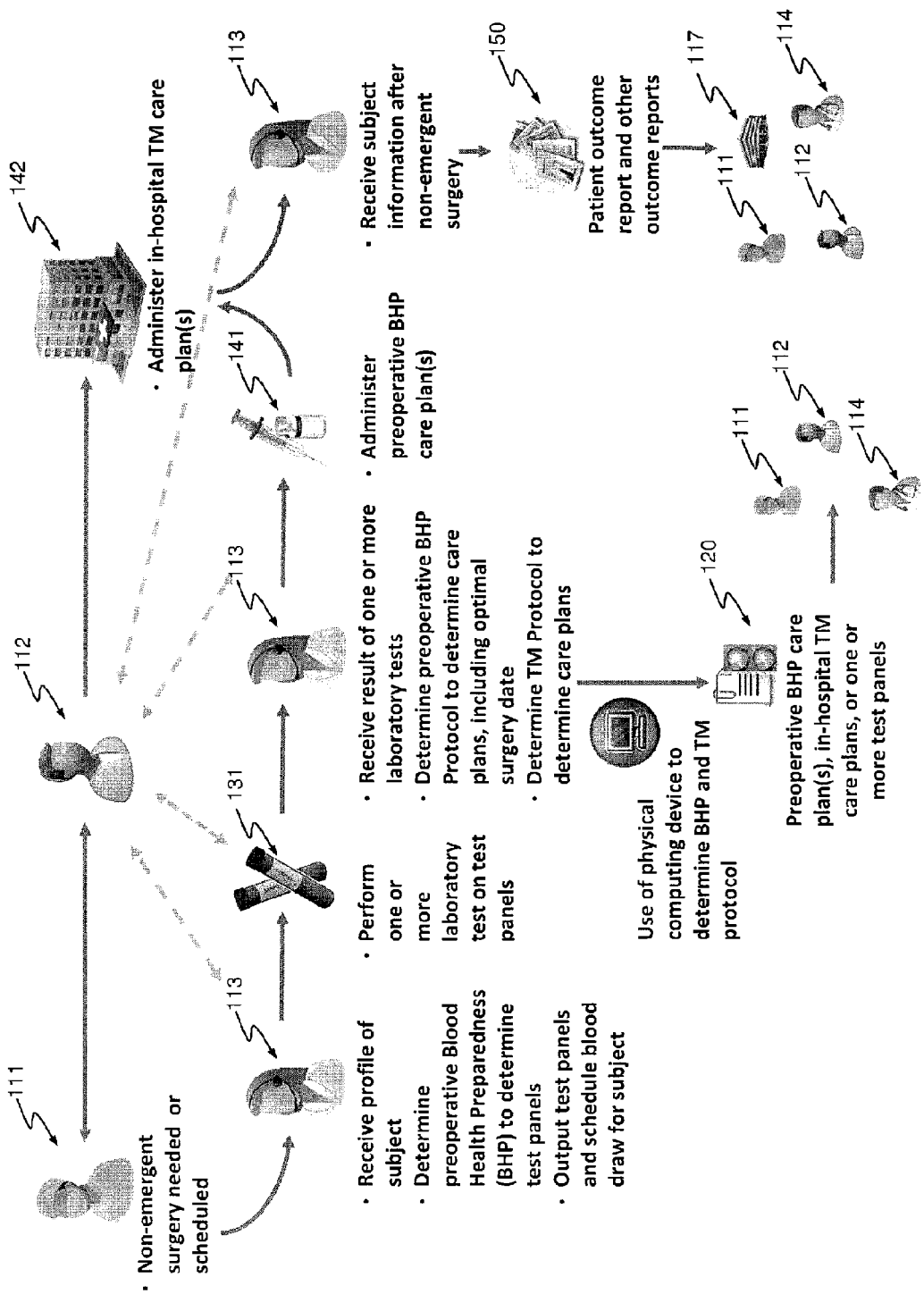

FIG. 1B is a block diagram generally showing a second embodiment of implementing the blood health management program. As compared to FIG. 1A, the embodiment of FIG. 1B shows the transfusion management healthcare provider first receiving the profile and then determining the laboratory tests to be conducted on the subject's blood sample.

Referring to FIG. 1B, the healthcare provider 111 identifies as needed or schedules a non-emergent surgery for a subject 112, which results in contacting a transfusion management healthcare provider 113 to evaluate the patient's blood health readiness and transfusion associated risk for the indicated surgery type. The transfusion management healthcare provider 113 receives a profile of the subject and performs a blood health preparedness protocol to output one or more test panels. Then, the one or more laboratory tests are ordered by the transfusion management healthcare provider 113 based on the test panel. Optionally, the transfusion management healthcare provider 113 can also schedule the blood draw for the subject 112 and refer the subject 112 to a laboratory to perform the blood draw. The laboratory tests are performed 131, and the results of the tests are then received by the transfusion management healthcare provider 113, along with the subject's profile. These data, including the profile and laboratory test, can be first inputted into the physical computing device and then outputted to the transfusion management healthcare provider on a computer readable medium, server, network, display device (e.g., a computer dashboard providing a user interface to access the subject's profile, outcome report, or care plans), or printed report. All results are considered to be part of the subject's composite profile, which is used to determine the blood health preparedness protocol and the in-hospital transfusion minimization plan.

After performing the blood health preparedness protocol, one or more of the preoperative care plan(s), in-hospital transfusion minimization care plan(s), or a test panel 120 are transferred, transmitted, sent, or communicated to one or more of the surgeon 111, hospital employee 114, or subject 112. The subject's healthcare provider (e.g., surgeon or a primary care physician) administers the preoperative care plan(s) to the subject 141 and the in-hospital transfusion minimization care plan(s) to the subject 142. The transfusion management healthcare provider 113 receives information regarding the subject, initially inputted in the physical computing device. When information has been received, or identified as missing, needed data are outputted to the transfusion management healthcare provider, after undergoing the non-emergent surgery. Using this information, a patient outcome report or other outcome reports 150 can be determined and then transferred, transmitted, sent, or communicated to one or more of the surgeon 111, subject 112, hospital employee 114, or health insurance provider 117. Using this program in a reiterative manner, the blood health preparedness protocol described herein can be used to manage the subject though computer-aided notification and support after administering a care plan.

The implementation of the blood health management program can include other additional embodiments. For example, the protocol can include the assignment of an off-site physician or other trained healthcare provider to the subject, subject's caregiver, or subject's physician. The off-site physician would be available to answer any questions about the outpatient special care plan(s) or in-hospital transfusion minimization care plan(s) (e.g., the off-site physician can be available 24 hours a day for questions regarding anemia evaluation, anemia treatment, safe transfusion avoidance, safe transfusion minimization, transfusion risks, transfusion effectiveness, transfusion appropriateness, transfusion administration, and transfusion reactions, including serious adverse events such as hemolytic and pulmonary reactions). In another example, the blood health management program can include additional information for physicians. Specific examples of additional information include a transfusion safety education module with continuing medical education credits and annual documentation; or availability of evidence-based transfusion guidelines provided by the representative. In yet another example, the blood health management program can include additional information for subjects, such as self-advocacy information; or educational information regarding the medical necessity of transfusions.

Figure 1C:
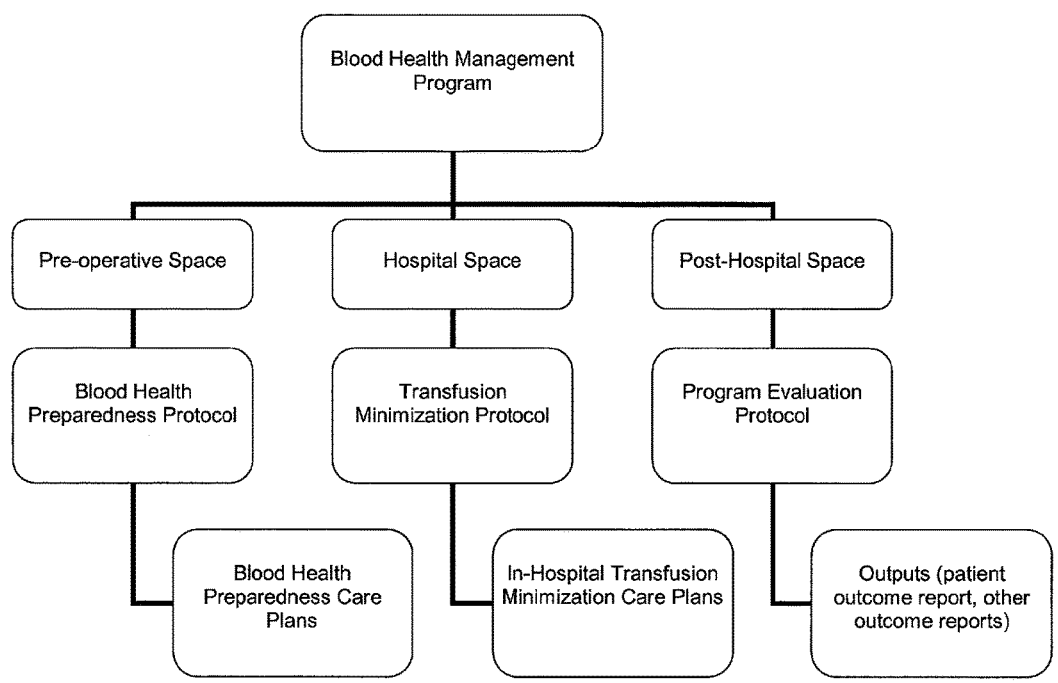
FIG. 1C is a flowchart showing an exemplary blood management health protocol including a blood health preparedness protocol, a transfusion minimization protocol, and a program evaluation protocol.

FIG. 1C is a flowchart showing an exemplary blood health management program showing various components of the protocol that relate to different times during the non-emergent surgery process. In the preoperative space, the blood health preparedness ("BHP") protocol is implemented to determine various preoperative BHP care plans. Exemplary BHP care plans are described herein (e.g., baseline plan and special care plans 1-6 in FIG. 8H). In the hospital space, the transfusion minimization protocol is implemented to determine various in-hospital transfusion minimization ("TM") care plans. Exemplary TM care plans are described herein (e.g., hospital plans A-G in FIG. 8I). In the post-hospital space, the program evaluation protocol is implemented to determine various outputs. Exemplary outputs include the patient output report and other outcome reports, as described herein.

Generally, the blood health management program is a method of applying a subject's profile to determine one or more predictions and applying those predictions to output one or more of a preoperative BHP protocol with special care plans (or a BHP protocol for anemic patients with chronic diseases and chronic heart failure patients with iron depletion), an in-hospital transfusion minimization protocol with in-hospital transfusion care plan(s), or test panel(s). Specific examples of one or more predictions include level of transfusion risk, level of comorbidity, level of bleeding risk, range of anticipated loss of blood volume, or range of tolerable loss of blood volume. Provided herein are methods of reducing transfusions during or after a surgery by performing a blood health management program, these methods also able to identify and treat anemia in non-surgical chronic disease patients, as well as methods for treating a subject undergoing a non-emergent surgery by administering one or more of a preoperative BHP special care plans and an in-hospital transfusion minimization protocol with care plan(s) to the subject.

Types of Non-Emergent Surgery

The blood health management program can be used in situations involving a non-emergent surgery, where there is sufficient time to apply the BHP protocol. Typically, a non-emergent surgery is a scheduled surgical procedure and one with high anticipated blood loss (e.g., about 600 mL). Examples of types of non-emergent high blood loss surgery include, but are not limited to, orthopedic joint replacement and spine surgeries, such as knee replacement surgery (e.g., single or bilateral surgeries, or total or partial knee replacement surgery (primary or revision)), total hip joint arthroplasty (also known as total hip replacement surgery (primary or revision)), or spine surgery (e.g., involving three or more vertebras); cardiovascular surgery, such as valve surgery (e.g., cardiac valve replacement or cardiac valve repair), coronary artery bypass surgery (e.g., with or without cardiac valve repair or replacement), or aortic replacement surgery; genitourinary surgery (e.g., radical retropubic prostatectomy and cystectomy); gastrointestinal surgery, such as to treat cancer (e.g., esophagectomy, gastrectomy, or colectomy), or inflammatory bowel disease (e.g., colectomy); other vascular surgery (e.g., aneurysm repair); gynecology surgery, including gynecological oncology surgery and uterine cancer surgery (e.g., hysterectomy with or without bilateral salpingo-oophorectomy, tumor debulking, omentectomy, and lymph node sampling); neurosurgery (e.g., meningioma resection or surgery to correct vascular malformations); an oncologic thoracic surgery (e.g., removal of lung tumors); a high-risk cesarean delivery; or any combination thereof. In particular, the method is performed to reduce transfusions during or after a surgery that would likely result in a high loss of blood volume by the subject.

Blood Health Management Program for Chronic Disease

The blood health management program described herein for a subject having non-emergent surgery can be modified for treating a subject having a chronic disease but not scheduled for a surgery. For example, the blood health management program would include many of the same features described above for FIGS. 1A-1B, but a transfusion minimization ("TM") protocol would not be generated by the management healthcare provider. Thus, a BHP care plan would be prepared but not an in-hospital transfusion minimization plan. Further details for a BHP care plan for subjects with chronic disease are described herein.

Types of Chronic Disease

The blood health management program can also be used by patients with certain chronic diseases associated with symptoms related to one or more of anemia, iron-depletion, or iron-deficiency. Generally, subject having a chronic disease have an underlying diagnosis of anemia, iron-depletion, or iron-deficiency, which can be determined by any useful assay or test described herein. Thus, the protocols and care plans described herein can be used to treat subject undergoing non-emergent surgery (either having or not having a chronic disease) or a subject having a chronic disease but not undergoing non-emergent surgery. Exemplary chronic diseases include a chronic heart failure, an inflammatory gastrointestinal disease (e.g., chronic inflammatory bowel disease or chronic autoimmune bowel disease), a rheumatologic inflammatory disease (e.g., a rheumatologic disease or an autoimmune disease), a chronic viral disease (e.g., hepatitis C infection, hepatitis B infection, or HIV infection), a chronic inflammatory state (e.g., diabetes, chronic renal disease, or obesity), a gynecological state (e.g., patients who are pregnant or have excessive uterine loss), and a post-surgical state (e.g., a patient who had bariatric surgery). For subject having a chronic disease and isolated deficiencies, the care plan will generally include treatment with the absent agent (e.g., iron-depleted or iron-deficient subjects will be treated with intravenous iron, vitamin B12-deficient subjects will be treated with intramuscular vitamin B12, and folate-deficient subjects will be treated with oral folate). Erythropoietin-stimulating agents (ESAs) may be given to patients who fulfill treatment requirements in regard to renal failure and to those who fail a single agent therapy. ESA's include erythropoietin (e.g., epoetin, epoetin alfa, darbepoetin, epoetin delta, PDpoetin, and methoxy polyethylene glycol-epoetin beta).

Health Insurance Plans

Further embodiments can include ensuring that the BHP care plans, for pre-surgical and chronic disease patients, and in-hospital TM plans include treatments that are covered by the subject's health insurance provider. For example, the BHP protocol can include one or more queries about the subject's health insurance plan (e.g., using a patient intake questionnaire), such as the identify of the health insurance provider; the type of health insurance plan; and the coverage provided, allowed, or restricted by the subject's insurance plan, including the types of medical procedures, laboratory tests, treatments, or medications included in the subject's insurance plan. In particular, the blood health management program can be tailored to the requirements of an insurance plan in order to maximize coverage for the medical procedures, laboratory tests, treatments, or medications in the care plans and to minimize waste, expense and frustration of offering an initial care plan that might fail an insurance plan's requirements and restrictions. For example, if an insurance plan requires pre-authorization by the subject's healthcare provider to perform a particular laboratory test or allow a particular treatment or medication, then the blood health management program will include the step of receiving and documenting approval from the subject's health insurance provider for the laboratory test, treatment, or medication.

For example, the profile can include information regarding the subject's health insurance plan, and the BHP protocol can include rules regarding allowed or restricted medical procedures, laboratory tests, treatments, or medications for a particular health insurance plan. Exemplary rules include if insurance plan A allows Venofer® for any patient, and insurance plan B only allows Venofer® if patient has a reaction to InFeD® first, then the BHP protocol accounts for these rules and ensures that appropriate medications covered by insurance are provided in the patient care plan. Additional examples of these methods using insurance information are provided herein.

Blood Health Preparedness Protocol

Figure 8A:
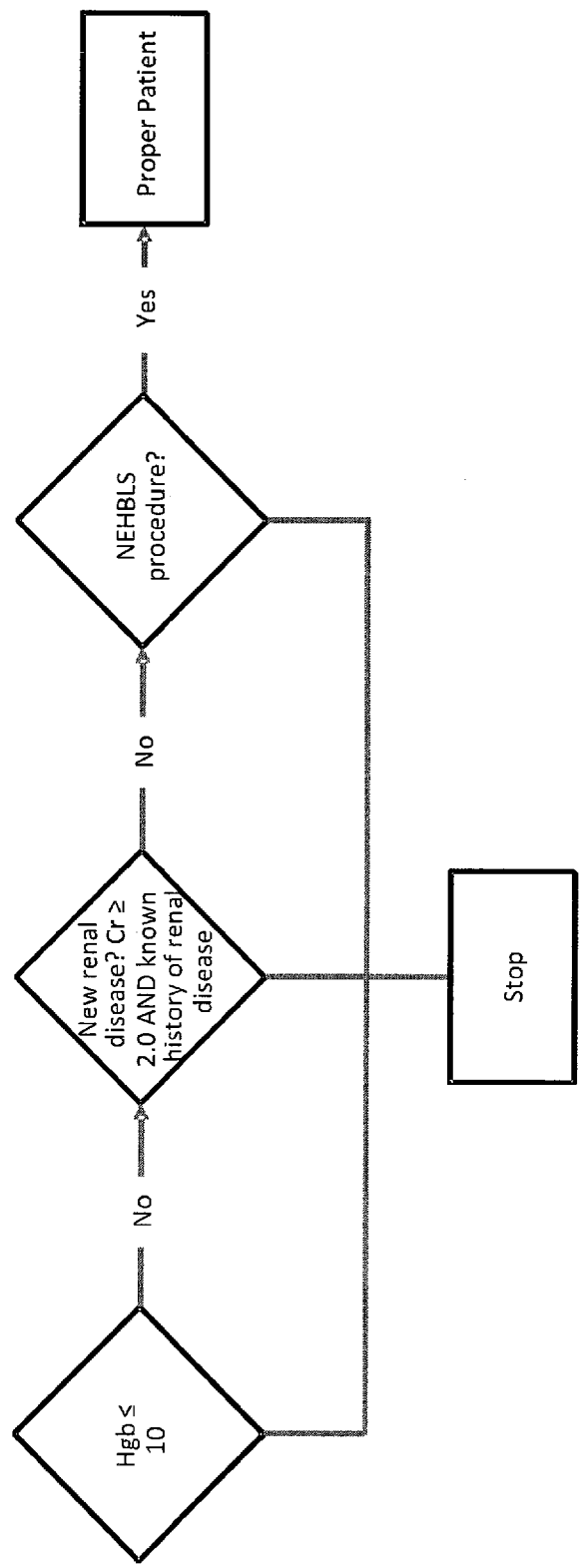
FIGS. 8A-8I are flowcharts providing a non-limiting method of reducing transfusions, including selecting patients with high risk (FIG. 8A), determining transfusion risk by using a scoring system (FIGS. 8B-1 to 8B-3), determining which patients are candidates for use of a cell saver (FIG. 8C), determining which patients are active smokers (FIG. 8D), determining which patients are taking anticoagulant medication (FIG. 8E), determining bleeding risk in a patient (FIG. 8F), determining red cell antibodies in a patient (FIG. 8G), determining a preoperative anemia care plan (FIG. 8H-1 to 8H-3), and determining an in-hospital transfusion minimization protocol with care plans (FIGS. 8I-1 to 8I-2).
Figures 1, 8B:
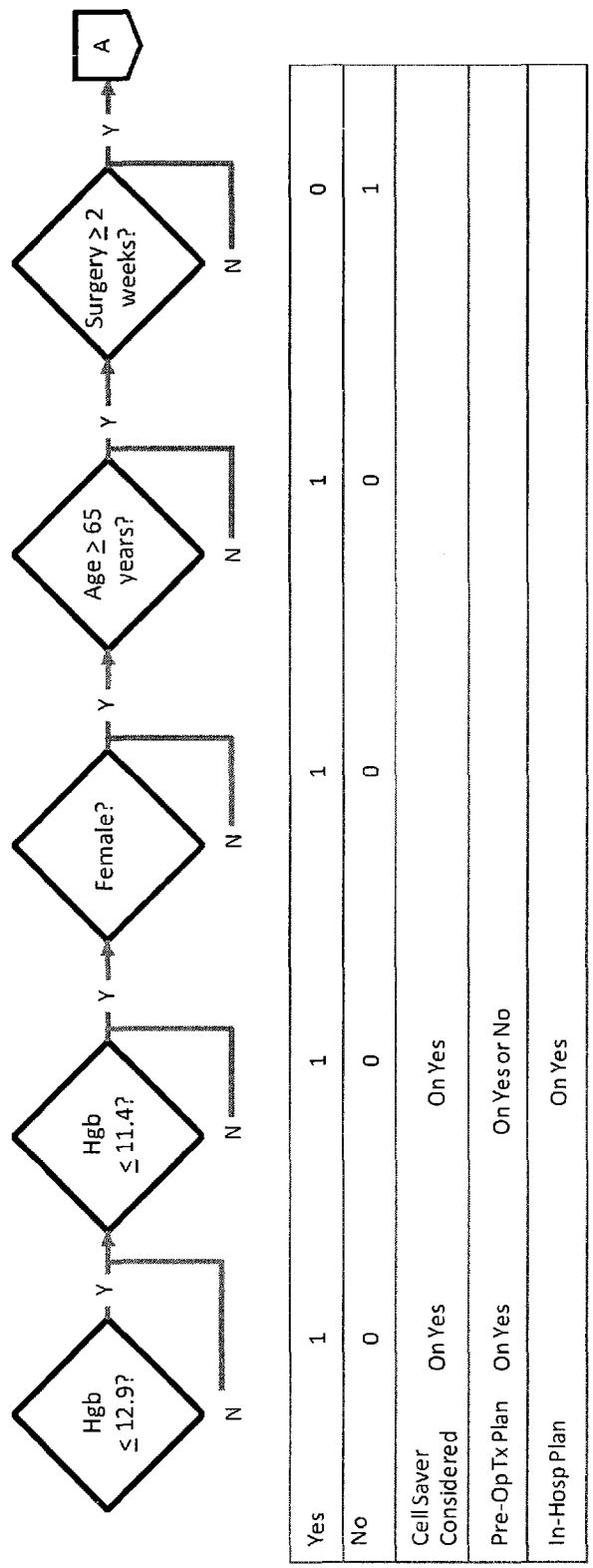
Figures 2, 8B:
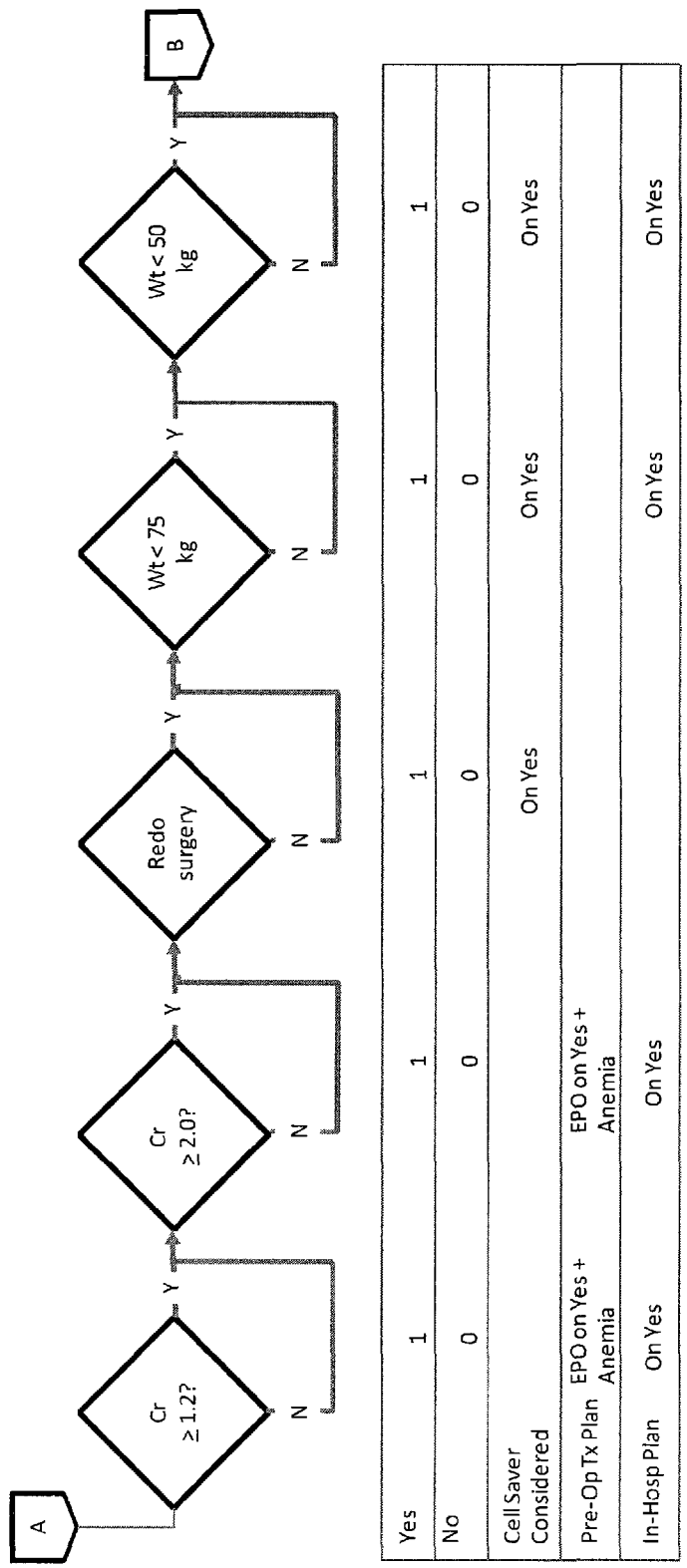

FIG. 2 shows one embodiment for a blood health preparedness protocol 200 based on a profile of the pre-surgical subject. Briefly, the method 200 comprises receiving a profile 201, determining various levels of risk based on the profile 210-212, determining a patient special care plan 220 and a first test panel 221, and outputting the patient special care plan and first test panel 230.

Profile

The profile can include any information regarding a subject preparing to undergo a non-emergent surgery. Specific examples of such information include level of hemoglobin, either obtained from the healthcare records of the subject or obtained from a laboratory test performed based on a test panel; level of creatinine, either obtained from the healthcare records of the subject or obtained from a laboratory test performed based on a test panel; red cell antibody information, either obtained from the healthcare records of the subject or obtained from a laboratory test performed based on a test panel; information regarding current and past history of disease, such as current and past history of anemia, autoimmune disease, bleeding (including a history of any bleeding disorder, e.g., history of coagulopathy, a blood clotting disorder, excessive bleeding, excessive clotting, etc.), cancer, cardiovascular disease (e.g., angina, myocardial infarction, valve disease, arrhythmia), cerebrovascular disease (e.g., stroke or transient ischemic attack), diabetes, gastrointestinal disease, infection (e.g., active infection), inflammatory disease, renal disease (e.g., renal failure), pulmonary disease (e.g., chronic obstructive pulmonary disease or pulmonary fibrosis), or previous surgeries; information regarding medication taken by said subject, such as one or more of anticoagulant medications (e.g., heparin, warfarin (Coumadin), clopidogrel (Plavix®), dong quoi, bromelain, chamomile, dandelion root, garlic, ginger, gingko biloba, St. John's wort, or vitamin C), procoagulant medications (e.g., a zeolite, desmopressin, a coagulation factor, such as factor VII, tranexamic acid, aminocaproic acid, or aprotinin), insulin, or erythropoietic medications (e.g., erythropoietin, epoetin, epoetin alfa, darbepoetin alfa, epoetin delta, PDpoetin, and methoxy polyethylene glycol-epoetin beta); subject demographics, such as height, weight, gender, date of birth, or age; information regarding the subject's lifestyle habits, such as diet, exercise, tobacco use, or alcohol use; date of said non-emergent surgery; type of non-emergent surgery; information regarding whether said non-emergent surgery is a redo procedure; or information regarding whether said non-emergent surgery is non-isolated, such as a bilateral knee surgery that requires both knees to be operated or a combination of a coronary artery bypass and valve surgery being scheduled at the same time.

The profile can further include information of a blood health index, for example, a level determined by one or more of laboratory tests selected from the group consisting of complete blood count (e.g., with reticulocyte count, platelet count, white blood cell (WBC) count, red blood cell (RBC) count, a hemoglobin (Hgb) test, a hematocrit (Hct) test, mean corpuscular volume (MCV), mean corpuscular hemoglobin (MCH), mean corpuscular hemoglobin concentration (MCHC), red cell distribution width (RDW), and reticulocyte hemoglobin concentration), complete iron studies (e.g., serum iron, transferrin, % iron saturation (or % saturation of transferrin by iron), total iron binding capacity, and ferritin), a hemoglobin (Hgb) test, a vitamin B12 test, a folate test, a reticulocyte count, a platelet count, a WBC count, serum iron, iron binding capacity, % iron saturation (or % saturation of transferrin by iron), a ferritin assay, a C reactive protein (non-cardiac) assay, a creatinine test, a glomerular filtration rate (GFR) test, a creatinine test with GFR, a methylmalonic acid (MMA) test, a transferrin assay, a soluble transferrin receptor assay, a hepcidin assay, an interleukin-6 assay, and an epoetin or erythropoietin test.

The profile can also include information regarding the subject's health insurance plan, such as type of coverage for one or more treatments, procedures, or medications for a possible BHP care plans, for pre-surgical and chronic disease patients, and in-hospital TM plans; and approved sites of care locations; and caveats or rules relating to allowed or restricted medical procedure(s), treatment(s), laboratory test(s), and/or medication(s).

The composite subject profile can also be obtained from any meaningful source or combination of sources to complete the required data sets, such as from the subject's physician or from the subject. For example, an initial profile can be obtained from the subject's healthcare provider and then a latter profile can be obtained from the subject by using a questionnaire. Exemplary questionnaires include the Preoperative Questionnaire from the Institute for Clinical Systems Improvement (Health Care Guideline: Preoperative Evaluation, July 2008 ($8^{th}$ edition)) and the Patient History questionnaire (Seeber and Shander, "Basics of Blood Management," Blackwell Publishing, 2007, p. 335).

Level of Comorbidity

The level of comorbidity can be determined 210 by any useful combination of predetermined comorbid conditions or risk factors that indicates an increased risk of complications for a subject during surgery, such as by the presence or absence of one or more comorbid conditions. Specific examples of particular comorbid conditions (or comorbidities) include: cardiovascular disease (e.g., recent (within 6 weeks) myocardial infarction or congestive heart failure), cerebrovascular disease (e.g., stroke, such as due to carotid atherosclerosis, or transient ischemic attacks), pulmonary disease (e.g., chronic obstructive pulmonary disease or pulmonary disease arising from other diseases, such as congestive heart failure), renal disease, cancer (e.g., active malignancy, including hematologic malignancies), autoimmune disease, gastrointestinal disease (e.g., gastrointestinal cancer or inflammatory bowel disease), history of blood clotting disorder (e.g., history of pulmonary embolism (PE) due to Factor V Leiden deficiency), or history of bleeding disorder (e.g., hemophilia).

Other examples of comorbidities include those identified in practice guidelines or checklists to be correlated with preoperative risk, such those described by the American Society of Anesthesiologists (*Anesthesiology* 105: 198-208 (2006)), Joehl (*Surg. Clin. N. Am.* 85: 1061-1073 (2005)), the Institute for Clinical Systems Improvement (Health Care Guideline: Preoperative Evaluation, July 2008 ($8^{th}$ edition)), and the American College of Cardiology and American Heart Association Task Force (Fleischer et al., *J. Am. Coll. Cardiol.* 50: e159-e242 (2007)). Exemplary comorbidities that indicate increased risk for surgery include diseases associated with organ ischemia (e.g., cardiorespiratory disease); history indicating coagulopathy (e.g., hemophilia, or use of warfarin); use of vitamins or supplements that affect coagulation (e.g., warfarin); conditions associated pulmonary dysfunction (e.g., COPD, cystic fibrosis, and asthma); conditions associated with cardiac dysfunction (e.g., coronary artery disease, unstable coronary syndromes, decompensated heart failure, significant arrhythmias, severe vascular disease, severe valvular disease, congenital heart deformities, previous myocardial infarction, or severe hypertension); conditions associated with renal dysfunction (e.g., renal failure); tobacco abuse; diabetes mellitus; and higher grades under the American Society of Anesthesiologists Physical Status ("ASA PS"), such as Grade III or IV.

The level of comorbidity or presence of a particular comorbid condition can be used to determine the severity of the level of comorbidity, which in turn can be used to determine outpatient BHP care plan(s), which takes into consideration that particular comorbidity. For example in regard to cardiovascular disease, a patient with recent (e.g., within 6 weeks) myocardial infarction without any treatment would have a higher level of comorbidity than a patient with a heart attack two years ago followed by successful stent placement, and change in lifestyle with decreased weight, lipids, and blood pressure. This higher level of comorbidity imposes higher risk for treatment, delay of surgery, or surgery itself. Further examples include: for cerebrovascular disease, a subject with prior stroke due to carotid atherosclerosis that has been treated successfully shows a lower level of comorbidity (or lower level of severity) or lesser risk than a subject with recent transient ischemic attacks for which the etiology has not been determined; for pulmonary disease, a subject with previous congestive heart failure ("CHF") shows a lower level of comorbidity or lesser risk than a subject with current CHF or a subject with any history of CHF that needs to be treated more cautiously than one without such history.

In regard to special care plans, a subject with a comorbidity of severe renal disease may be provided a care plan, where the surgery is planned in concert with immediate preoperative dialysis and administration of unique pharmacologic agents, such as DDAVP® (desmopressin acetate). In another example, an anemic patient with history of clotting disorders may be of too high risk to be treated for anemia or their treatment may need to be more carefully planned and monitored than an anemic patient without a clotting disorder.

In addition, combinations of comorbidities can be considered in determining the patient care plan. For example, subjects with cardiovascular disease who are treated for anemia may also need to be treated with anticoagulants for possible increased risk of deep vein thrombosis. In another example, the active CHF patient with anemia that is related to iron deficiency may be provided a preoperative BHP care plan including intravenous iron infusion in a solution. As the volume of this infusion may carry additional risk for this type of patient, the plan might also include giving the infusion very slowly, more so than in the patient with no history of active CHF.

Some comorbidities typically are associated with more than one disease state. For example, renal disease is typically associated with increased risk of bleeding, as well as anemia, where bleeding in these patients may be related to poor platelet function. For these subjects, the outpatient BHP care plan may include administration of erythropoietin and the in-hospital transfusion minimization care plan may need to note need for DDAVP® and platelet transfusion, in addition to red cell transfusion should excessive bleeding occur. Active cancer or the presence of certain kinds of cancer (e.g., hematologic malignancies) may indicate that anemia treatment with certain medications (e.g., erythropoietin) is contraindicated or that treatment requires other additional medications, such as anticoagulants. Autoimmune disease is frequently associated with anemia and treatment of this kind of low blood count may require erythropoietin. For gastrointestinal cancer, iron deficiency anemia is often present, which can be readily and rapidly improved with intravenous iron replacement. For gastrointestinal inflammatory conditions, the associated anemia may be related to iron loss and also iron absorption and incorporation defects, which may include a BHP care plan for anemia having both intravenous iron and, perhaps, erythropoietin.

Level of Transfusion Risk

The level of transfusion risk can be determined 211 by any useful combination of risk factors that indicates an increased risk of transfusion for a subject during surgery. For example, a scoring index for cardiac surgery is provided in Alghamdi et al., *Transfusion*, 46: 1120-1129 (2006). In another example, a scoring index for spine surgery is provided in Lenoir et al., *Anesthesiology* 110: 1050-1060 (2009). Additional transfusion related risk factors include the presence of anemia, the presence of one or more comorbid conditions, or the presence of rare red blood cell antibodies or alloantibodies, such that there is the possibility of not having a compatible blood component available for the patient.

High levels of transfusion risk may arise from a high risk of requiring a transfusion or a high risk of needing a transfusion of a rare blood component. A high risk of requiring a transfusion can arise from the presence of anemia or from the presence of a high scoring index that indicated an increased risk of transfusion. A high risk of needing a transfusion of a rare blood component can arise from the presence of rare red cell antibodies or a combination of antibodies. Determining one or more compatible blood types and incorporation that information into the in-hospital transfusion minimization care plan is described herein.

In another example, high levels of comorbidity can indicate a care plan including minimization of blood loss or return of fresh shed blood, as in using a cell saver device, if applicable (e.g., subject is without tumor or infection; the surgery doesn't involve the gastrointestinal tract; or surgery itself is the source of the blood loss, such as in hip surgery or in knee surgery). A high level of cardiovascular risk, for example, might also results in an in-hospital TM care plan suggesting transfusion at higher levels of hemoglobin and/or transfusion with fresh (e.g., less than ten days old) allogeneic blood.

Specific examples of risk factors for determining level of transfusion risk include a decreased level of hemoglobin, such as a level that indicates anemia (e.g., a level of hemoglobin that is less than or equal to 12.9 g/dL or less than or equal to 11.4 g/dL); low body weight, such as a weight of less than 75 kg or less than 50 kg; female gender; older age, such as an age of more than or equal to 65 years; whether the surgery is non-elective, such as when the date of the surgery is less than two weeks away; an increased level of creatinine, such as a level more than 1.2 mg/dL or more than 2.0 mg/dL; whether the non-emergent surgery is a redo procedure; or whether the non-emergent surgery is a non-isolated procedure.

A risk factor with a higher likelihood of increasing the level of transfusion risk would be assigned a higher value than a risk factor with a lower likelihood. Then, the risk factors are identified in a profile, values are assigned, and the sum of the values is compared to a reference range that indicates different levels of transfusion risk. In one non-limiting embodiment, a level of transfusion risk can be determined by:

receiving a profile comprising a level of hemoglobin, weight, gender, age, date of non-emergent surgery, level of creatinine, information regarding whether the non-emergent surgery is a redo procedure, and information regarding whether the non-emergent surgery is a non-isolated procedure;

applying the level of hemoglobin to determine a first value, where if the level of hemoglobin is less than or equal to 12.9 g/dL, then the first value is positive, and if the level of hemoglobin is more than 13.0 g/dL, then the first value is zero;

applying the weight to determine a second value, where if the weight is less than or equal to 75 kg, then the second value is positive;

applying the gender to determine a third value, where if the gender is female, then the third value is positive;

applying the age to determine a fourth value, where if the age is more than or equal to 65 years, then the fourth value is positive; applying the date of the non-emergent surgery to determine a fifth value, where if the date of the non-emergent surgery is less than two weeks away, then the fifth value is positive;

applying the level of creatinine to determine a sixth value, where if the level of creatinine is more than 1.2 mg/dL, then the sixth value is positive;

applying the information regarding whether the non-emergent surgery is a redo procedure to determine a seventh value, where if the information comprises a redo procedure, then the seventh value is positive;

applying the information regarding whether the non-emergent surgery is a non-isolated procedure to determining an eighth value, where if the information comprises a non-isolated procedure, then the eighth value is positive; and determining the level of transfusion risk, where if no more than one of the first value to the eighth value is positive, then the level of transfusion risk is low; if exactly two of the first value to the eighth value are positive, then the level of transfusion risk is intermediate; if exactly three of the first value to the eighth value are positive, then the level of transfusion risk is high; and if four or more of the first value to the eighth value are positive, then the level of transfusion risk is very high.

In another non-limiting embodiment, a level of transfusion risk is determined by applying the level of hemoglobin, where the level of risk is very high if the level of hemoglobin is 10.0 g/dL or lower in a non-bleeding and/or non-oncologic patient (e.g., as in an elective orthopedic surgery patient). In another non-limiting embodiment, a level of transfusion risk is determined by applying the level of creatinine, where the level of risk is very high if the level of creatinine indicates a new diagnosis of current renal disease. In situations of very high levels of transfusion risk, the risk may be so high as to result in a care plan that re-schedules the non-emergent surgery until the underlying condition is treated, unless the surgery is medically necessary as determined by a physician. For example, for a level of hemoglobin of 10.0 g/dL or lower, the etiology for the anemia should be identified and treated before pursuing surgery.

Figure 2A:
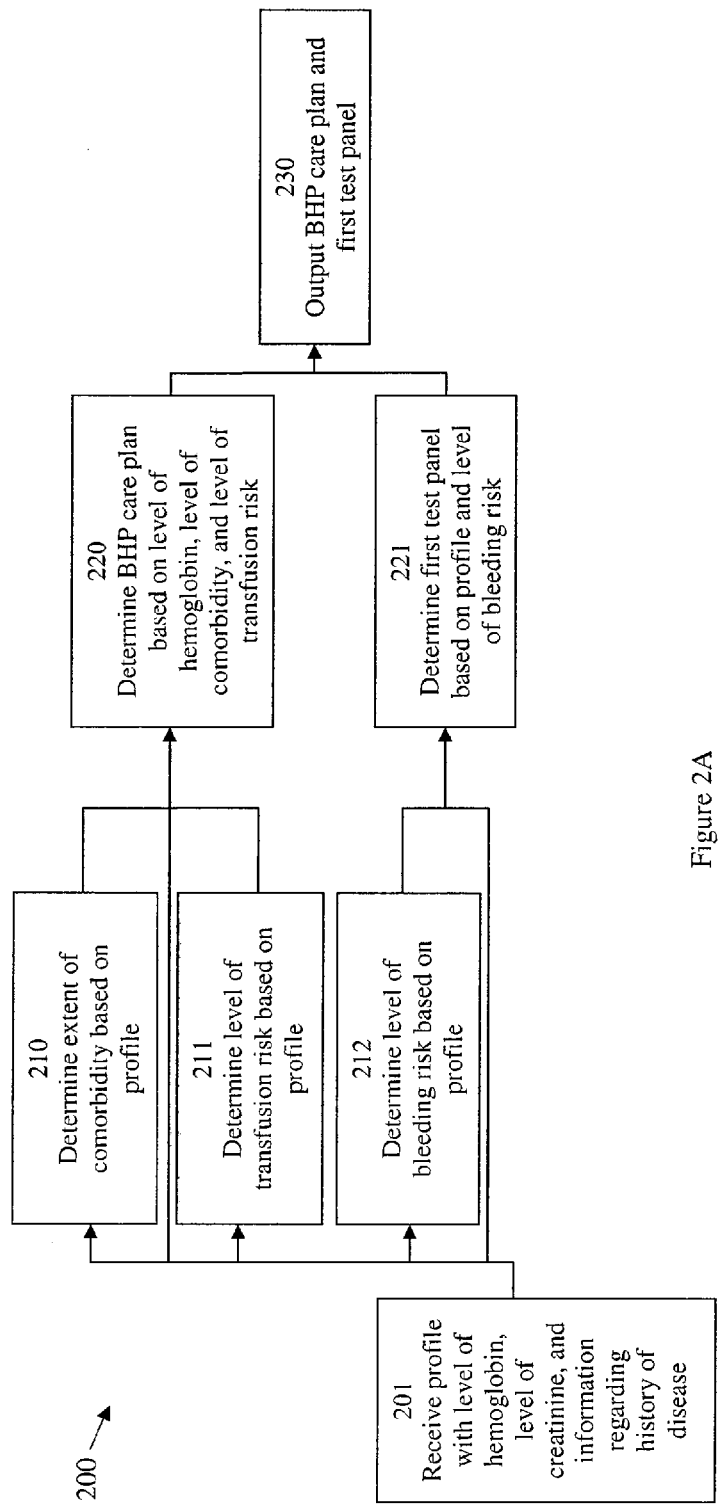
FIG. 2A is a flowchart of a first exemplary method of reducing transfusions by using a blood health preparedness ("BHP") protocol and a first test panel.
Figure 2B:
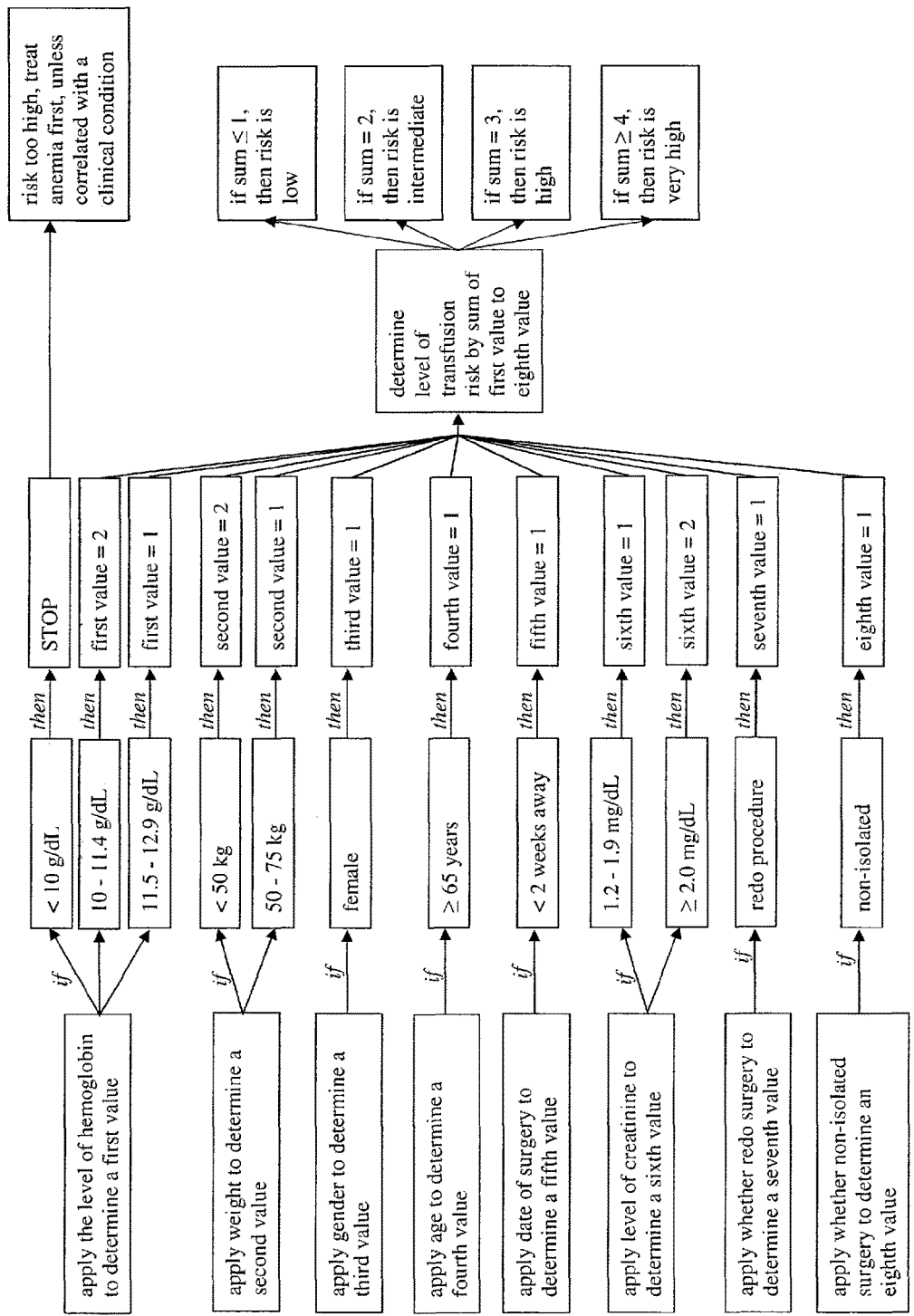
FIG. 2B is a flowchart of a non-limiting embodiment for determining level of transfusion risk.

FIG. 2B shows a preferred non-limiting embodiment for determining level of transfusion risk. In one embodiment, the level of transfusion risk is determined by assigning each risk factor with a particular value. In this figure, the profile includes information regarding a level of hemoglobin, weight, gender, age, date of non-emergent surgery, level of creatinine, information regarding whether the non-emergent surgery is a redo procedure, information regarding whether the non-emergent surgery is a non-isolated procedure, and information regarding whether the subject has chronic renal disease ("CRD" or chronic kidney disease). If the level of hemoglobin is less than or equal to 10.0 g/dL, then the subject is severely anemic. Due to such a high level of risk, the blood health management program is stopped and the subject's physician is contacted to consider identifying the cause of and treating the underlying anemic condition before going forward with the surgery. If the level of transfusion risk is too high, then anemia can be treated first. However, if severe anemia is correlated with the clinical condition, then the cause of anemia should be determined. For example, severe anemia is not expected in orthopedic patients and the cause of anemia should be determined and the patient should not have surgery. In another example, if the condition is a gastrointestinal malignancy, then severe anemia likely correlates with the clinical history. Therefore, rapid maximization of the patient's anemia in concert with getting the patient to surgery is indicated.

Overall, FIG. 2B shows that level of transfusion risk can be determined by:

receiving a profile comprising a level of hemoglobin, weight, gender, age, date of non-emergent surgery, level of creatinine, information regarding whether the non-emergent surgery is a redo procedure, information regarding whether the non-emergent surgery is a non-isolated procedure, and information regarding whether the subject has chronic renal disease;

applying the level of hemoglobin to determine a first value, where if the level of hemoglobin is less than 10.0 g/dL, then the level of transfusion risk is very high, if the level of hemoglobin is from between 10.0 g/dL-11.4 g/dL, then the first value is two, and if the level of hemoglobin is above 11.4 g/dL and below 13.0 g/dL (e.g., from 11.5 g/dL to 12.9 g/dL), then the first value is one;

applying the weight to determine a second value, where if the weight is less than 50 kg, then the second value is two and if the weight is between 50 kg and 75 kg, then the second value is one;

applying the gender to determine a third value, where if the gender is female, then the third value is one;

applying the age to determine a fourth value, where if the age is more than or equal to 65 years, then the fourth value is one;

applying the date of the non-emergent surgery to determine a fifth value, where if the date of the non-emergent surgery is less than two weeks away, then the fifth value is one;

applying the level of creatinine to determine a sixth value, where if the level of creatinine is from 1.2 mg/dL to 1.9 mg/dL, then the sixth value is one, and if the level of creatinine is more than or equal to 2.0 mg/dL, then the sixth value is two;

applying the information regarding whether the non-emergent surgery is a redo procedure to determine a seventh value, where if the information comprises a redo procedure, then the seventh value is one;

applying the information regarding whether the non-emergent surgery is a non-isolated procedure to determining an eighth value, where if the information comprises a non-isolated procedure, then the eighth value is one; and determining the level of transfusion risk, where if the sum of the first value to the eighth value is no more than one, then the level of transfusion risk is low; if the sum of the first value to the eighth value is two, then the level of transfusion risk is intermediate; if the sum of the first value to the eighth value is three, then the level of transfusion risk is intermediate; and if the sum of the first value to the eighth value is four or more, then the level of transfusion risk is very high.

Other aspects of the BHP protocol can be implemented by using this value system. For example, the level of comorbidity or the level of bleeding risk can be determined by assigning each risk factor (e.g., the presence of a particular disease or condition) with a particular value. The level of comorbidity can be determined by any useful method, such as scores under the American Society of Anesthesiologists Physical Status ("ASA PS") classification system (see, e.g., Cullen et al., *Ann. Surg.* 220: 3-9 (1994)), the Department of Veteran Affairs National Surgical Quality Improvement Program ("NSQIP") classification system (see, e.g., Davenport et al., *Ann. Surg.* 243:636-644 (2006)), a morbidity index correlated with the International Classification of Diseases (see, e.g., Deyo et al., *J. Clin. Epidemiol.* 45: 613-619 (1992)), the RAND comorbidity index (see, e.g., Keeler et al., *JAMA* 264:1962-1968 (1990)), or the comorbidity score described in Peersman et al., *Acta Orthop. Belg.* 74: 360-364 (2008).

Patient Care Plans, Including Preoperative BHP and In-Hospital TM Care Plans

A preoperative BHP care plan and/or in-hospital TM care plan can be determined by using any combination of information from the profile and any combination of risk factors. As shown in FIG. 2, the outpatient BHP care plans are determined based on level of hemoglobin, level of comorbidity, and level of transfusion risk 220. The care plans (BHP and TM) can be one or more of any useful treatment or intervention that would address the determined level of hemoglobin, level of comorbidity, or level of transfusion risk. For example, the care plans (e.g., outpatient BHP and in-patient TM care plans) can include any preoperative, intraoperative, and postoperative blood management interventions or recommendations. Examples include one or more of administration of a multivitamin; administration of oral iron with ascorbic acid or intravenous iron (e.g., ferric carboxymaltose, iron sucrose (Venofer®), or iron dextran (InFeD®)); administration of ascorbic acid, erythropoietin, folate, or vitamin B12; administration of one or more of erythropoietic medications, such as, but not limited to, erythropoietin, epoetin, epoetin alfa, darbepoetin alfa, epoetin delta, PDpoetin, or methoxy polyethylene glycol-epoetin beta; preoperative autologous blood donation; acute normovolemic hemodilution; preoperative dialysis; administration of vasopressin or analogues thereof, such as desmopressin or desmopressin acetate; and preoperative coagulation therapy. Other specific interventions include those that strictly minimize blood loss, such as by use of a cell saver with washing and immediate re-infusion of fresh shed blood; or use of pediatric blood tubes for blood draws. Details of other care plans are also described herein, such as those to address a particular comorbidity.

In one preferred embodiment, the level of hemoglobin and/or level of creatinine are determined recently (e.g., within 72 hours, one week, two weeks, three weeks, or one month). If any abnormal levels of hemoglobin have been assessed to determine its cause, then the outpatient BHP care plan is determined to specifically address the cause of the abnormal levels of hemoglobin. For example, anemia can be related to iron deficiency, and if so determined, then the outpatient special care plan (e.g., FIG. 8H-1, special care plan 1) would include medications to increase the level of iron, such as by use of oral or intravenous iron.

In another preferred embodiment, the level of hemoglobin, level of creatinine, and red cell antibody information are determined recently (e.g., within a week, two weeks, three weeks, or one month), where the first test panel includes laboratory tests to test for these values.

Figures 3, 8B:
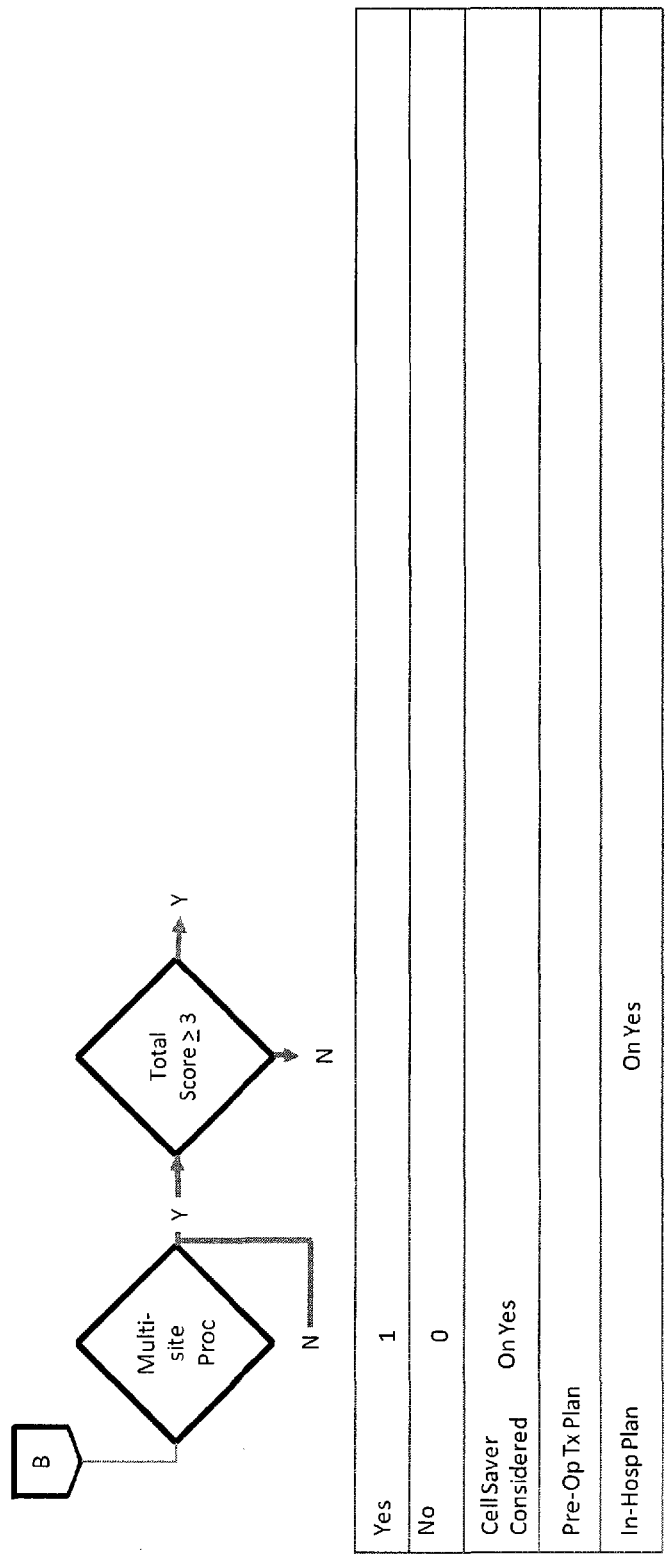
Figure 8C:
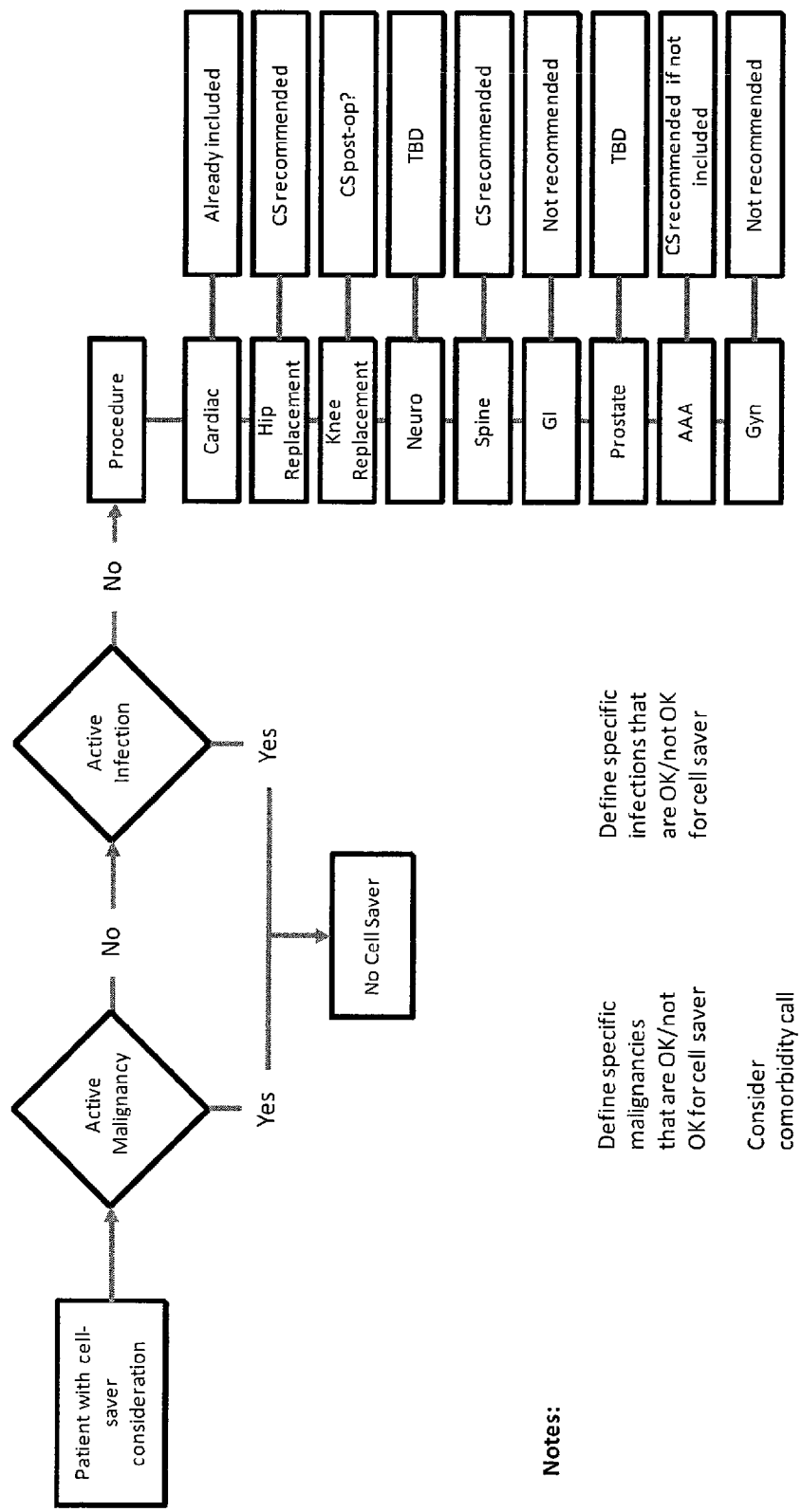
Figure 8D:
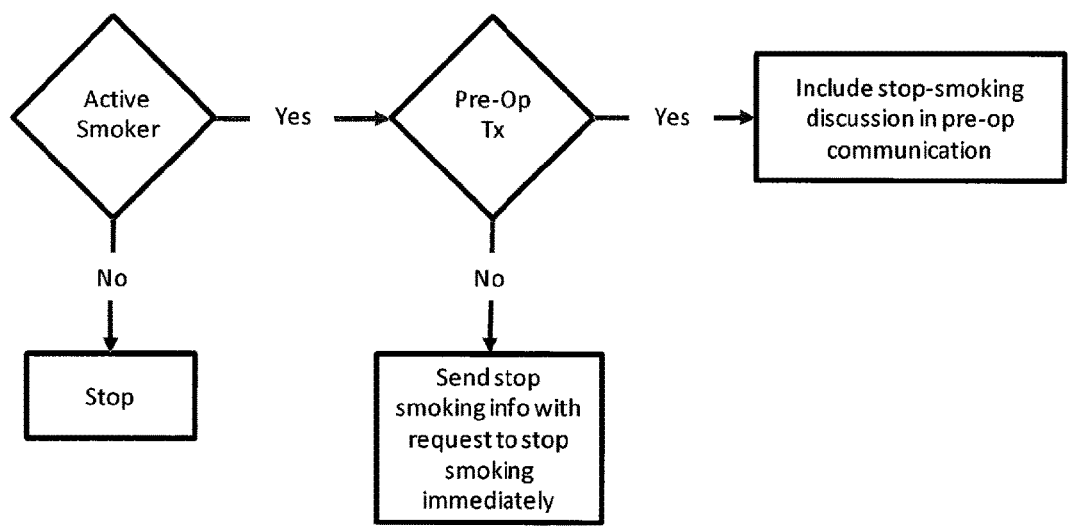
Figure 8E:
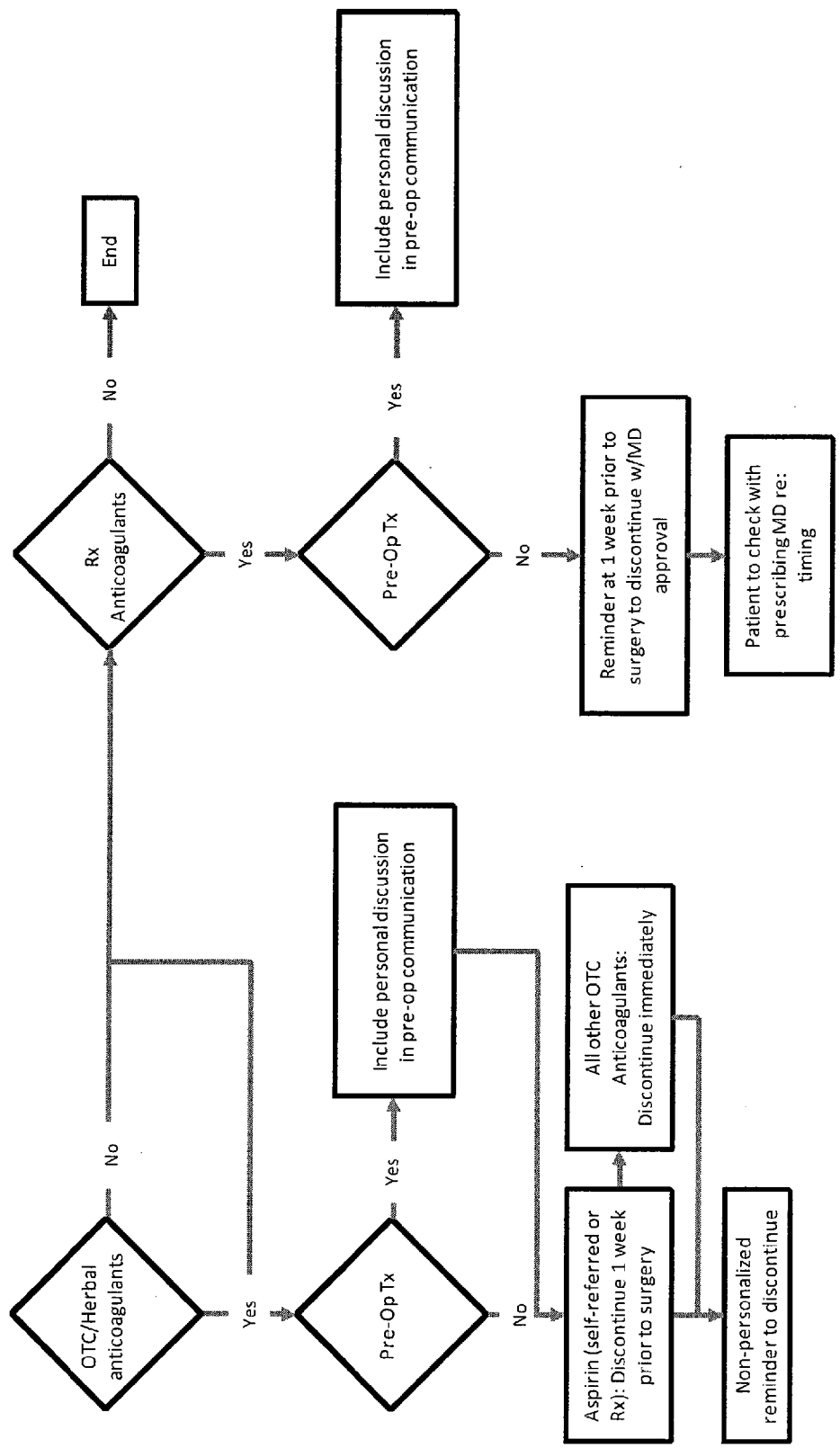
Figure 8F:
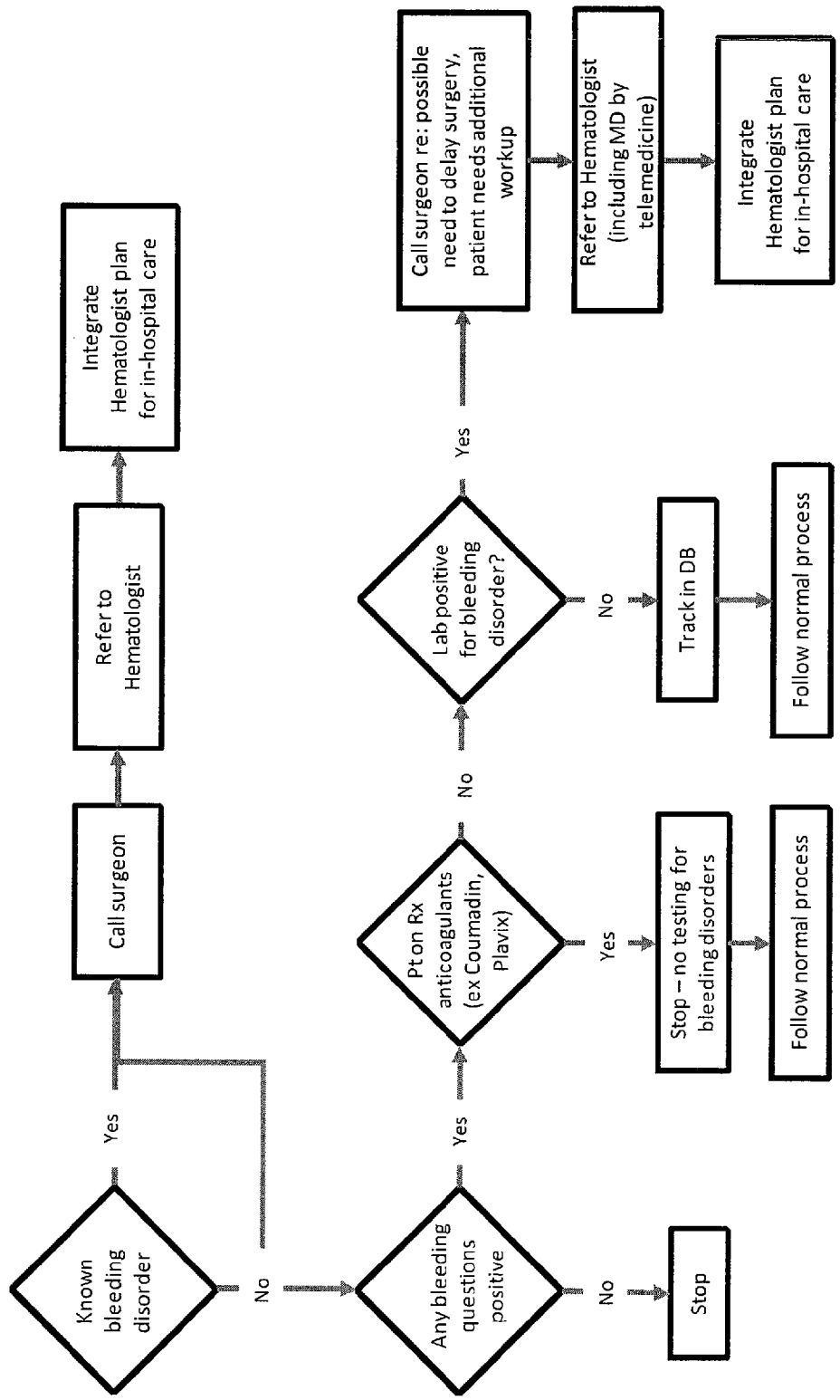
Figure 8G:
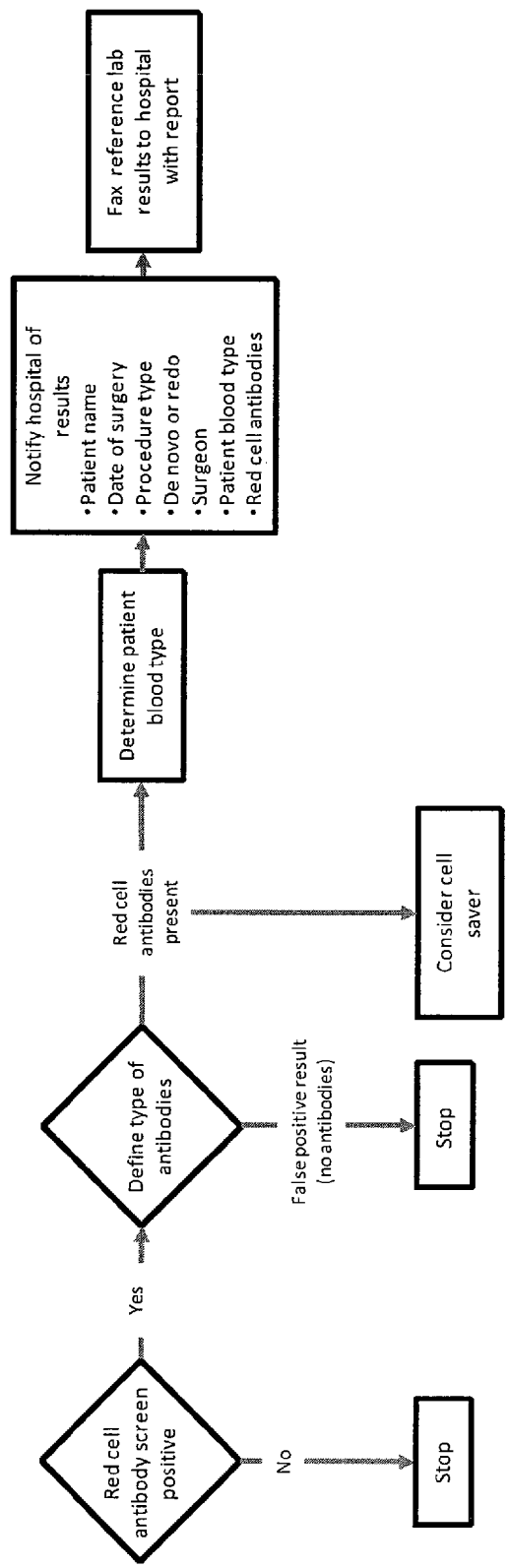
Figures 1, 8H:
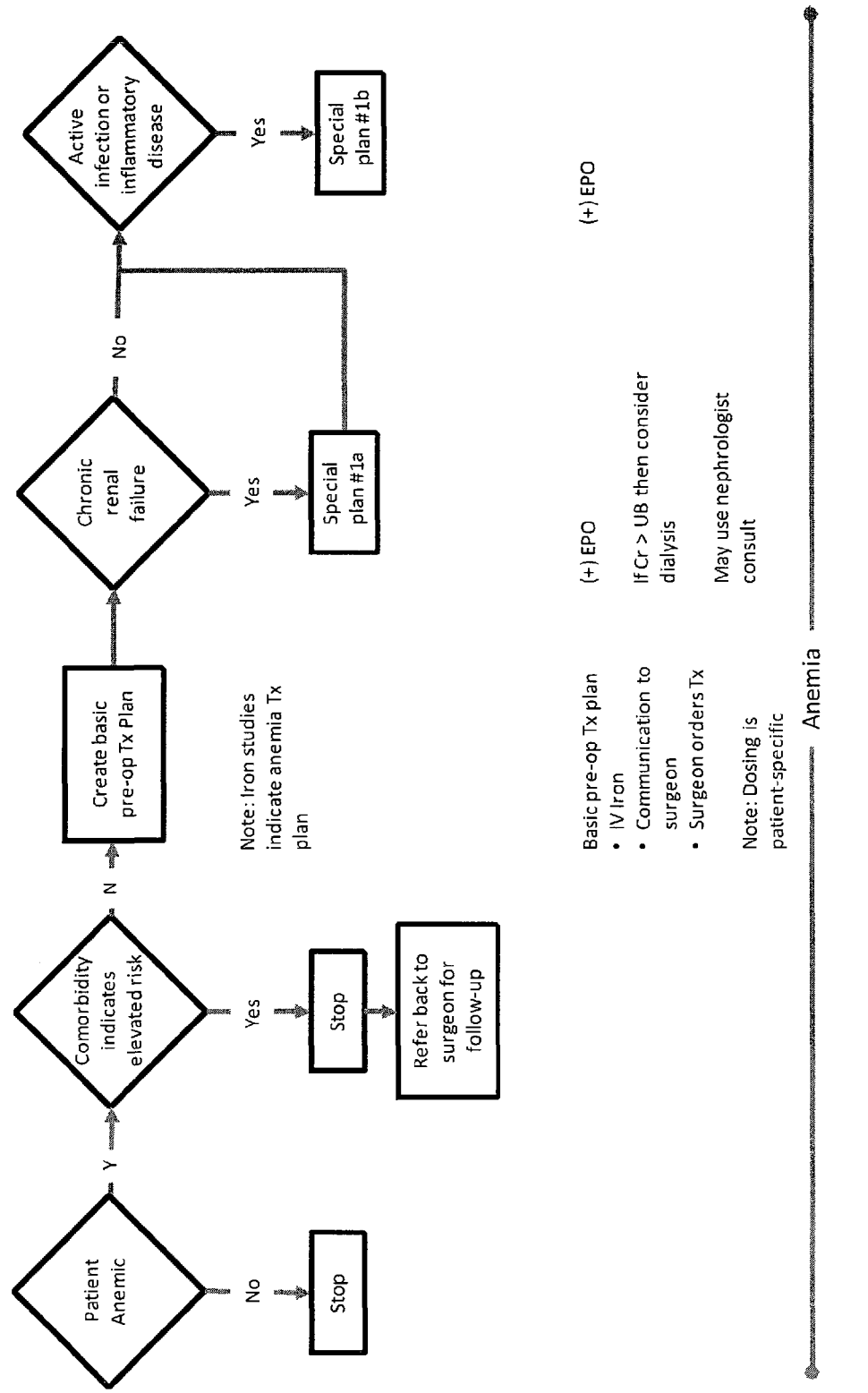
Figures 2, 8H:
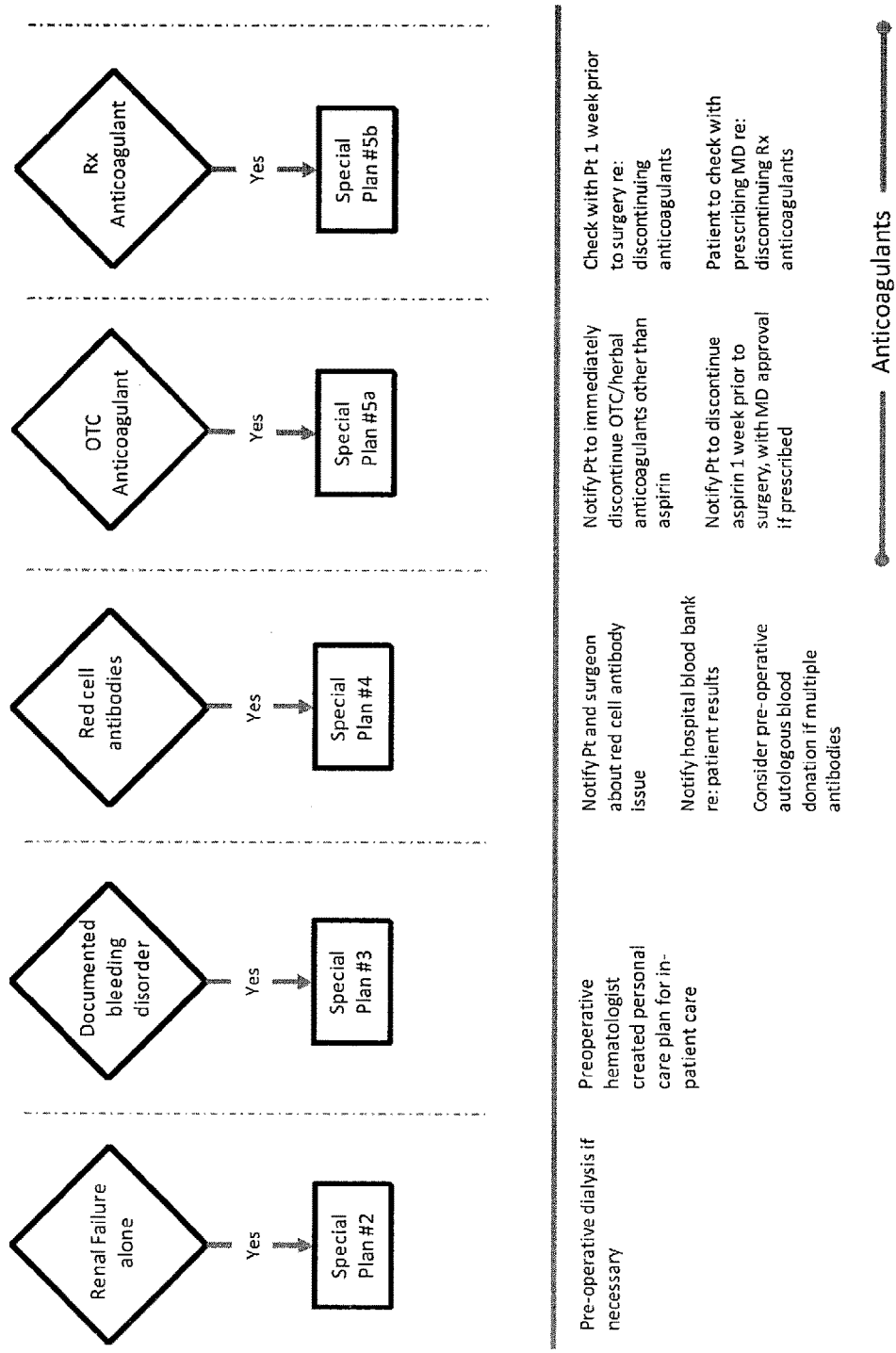
Figures 3, 8H:
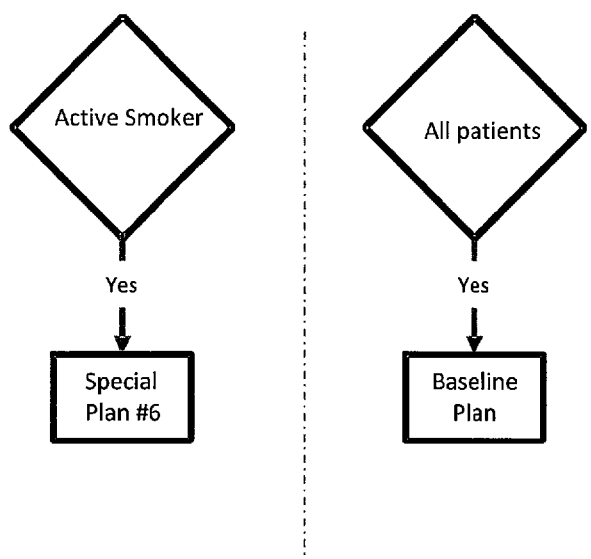

Exemplary preoperative BHP care plans include: for a subject that is not anemic with no significant history, administration of a multivitamin containing iron and separate ascorbic acid (vitamin C) concomitantly (e.g., FIG. 8H-3, baseline plan); for a subject that is not anemic with no significant history but takes aspirin prophylactically due to family history of heart attacks, administration of a multivitamin with iron and separate vitamin C and a call one week before surgery to stop taking aspirin with physician's permission; for a subject that is anemic with no comorbidities present, such that treatment is less risky than no treatment and/or receiving allogeneic transfusion (e.g., FIG. 8H-2, special plan 5*b*), the patient care plan includes those that will address the cause of anemia, where exemplary laboratory tests for the first test panel include complete blood count with reticulocyte count and platelet count, complete iron studies if the mean corpuscular volume (MCV) <80 (e.g., serum iron, transferrin, % iron saturation, total iron binding capacity, and ferritin), and a vitamin B12 and folate tests if MCV >100; for a subject with abnormal levels of creatinine (e.g., >1.2 mg/dL) or with a history or renal failure and anemia, additional testing on cause of anemia and treatment to include erythropoietin (e.g., FIG. 8H-1). Additional patient care plans are described herein (e.g., FIGS. 8H-1, 8H-2, and 8H-3).

Administration of Iron and Erythropoietic Medications

The medications described herein can be administered at any useful dose, as determined by a physician. Exemplary dosages include about 10,000 units to about 40,000 units of erythropoietin, epoetin, epoetin alfa, darbepoetin alfa, epoetin delta, PDpoetin, or methoxy polyethylene glycol-epoetin beta, subcutaneously, weekly; about 100 mg to about 500 mg (e.g., 200 mg to 300 mg) of iron sucrose (Venofer®), intravenously over 60 minutes, either with or without erythropoietin or epoetin; and about 125 mg to about 1,525 mg of iron dextran, intravenously with an initial dose, either with or without erythropoietin or epoetin. Further dosing regimens can be determined by monitoring the results from one or more laboratory tests selected from the group consisting of complete blood count (e.g., with reticulocyte count, platelet count, white blood cell (WBC) count, red blood cell (RBC) count, a hemoglobin (Hgb) test, a hematocrit (Hct) test, mean corpuscular volume (MCV), mean corpuscular hemoglobin (MCH), mean corpuscular hemoglobin concentration (MCHC), and red cell distribution width (RDW)), complete iron studies (e.g., serum iron, transferrin, % iron saturation (or % saturation of transferrin by iron), total iron binding capacity, and ferritin), a hemoglobin (Hgb) test, a vitamin B12 test, a folate test, a reticulocyte count, a platelet count, a WBC count, serum iron, iron binding capacity, % iron saturation (or % saturation of transferrin by iron), a ferritin assay, a C reactive protein (non-cardiac) assay, a creatinine test, a glomerular filtration rate (GFR) test, a creatinine test with GFR, a methylmalonic acid (MMA) test, a transferrin assay, a soluble transferrin receptor assay, a hepcidin assay, an interleukin-6 assay, a red cell hemoglobin assay, and an epoetin or erythropoietin test.

Effect of Hemoglobin on Care Plan

Anemia can be determined by any useful method (e.g., determining level of hemoglobin). As determined by the World Health Organization, the cut-off values for anemia include 12.0 mg/dL for non-pregnant women and 13.0 mg/dL for men above 15 years of age (World Health Organization, Iron Deficiency Anemia Assessment, Prevention, and Control: A guide for programme managers, Chapter 7 (2001)). However, for pre-surgical patients with planned high blood loss surgeries, a target hemoglobin of 13.0 g/dL is the value below which both males and females are considered anemic and treatments for this aim to position the subject's hemoglobin as close to 13.0 g/dL as possible. For chronic disease patients, the WHO criteria can be utilized unless iron-depletion is identified (e.g., in CHF patients). Alternatively, meta-analysis can be performed to determine cut-off values for anemia based on the patient population (see, e.g., Bisbe et al., *Transfusion Alternatives in Transfusion Medicine* 10: 166-173 (2009)).

Additional tests may be helpful to diagnose anemia and its etiology or etiologies if multifactorial, such as mean corpuscular volume (MCV), mean corpuscular hemoglobin (MCH), and mean corpuscular hemoglobin concentration (MCHC). For example, anemia can be present in a subject having a level of hemoglobin above the cut-off value but also having an abnormal level in the blood health index, including one or more abnormal levels characterized by a serum iron level <35 µg/dL, % iron saturation <25%, MCV <82 fL, MCV >100 fL, MCH <30 pg, ferritin <125 ng/mL, or C reactive protein (i) >8 mg/L.

Figure 3A:
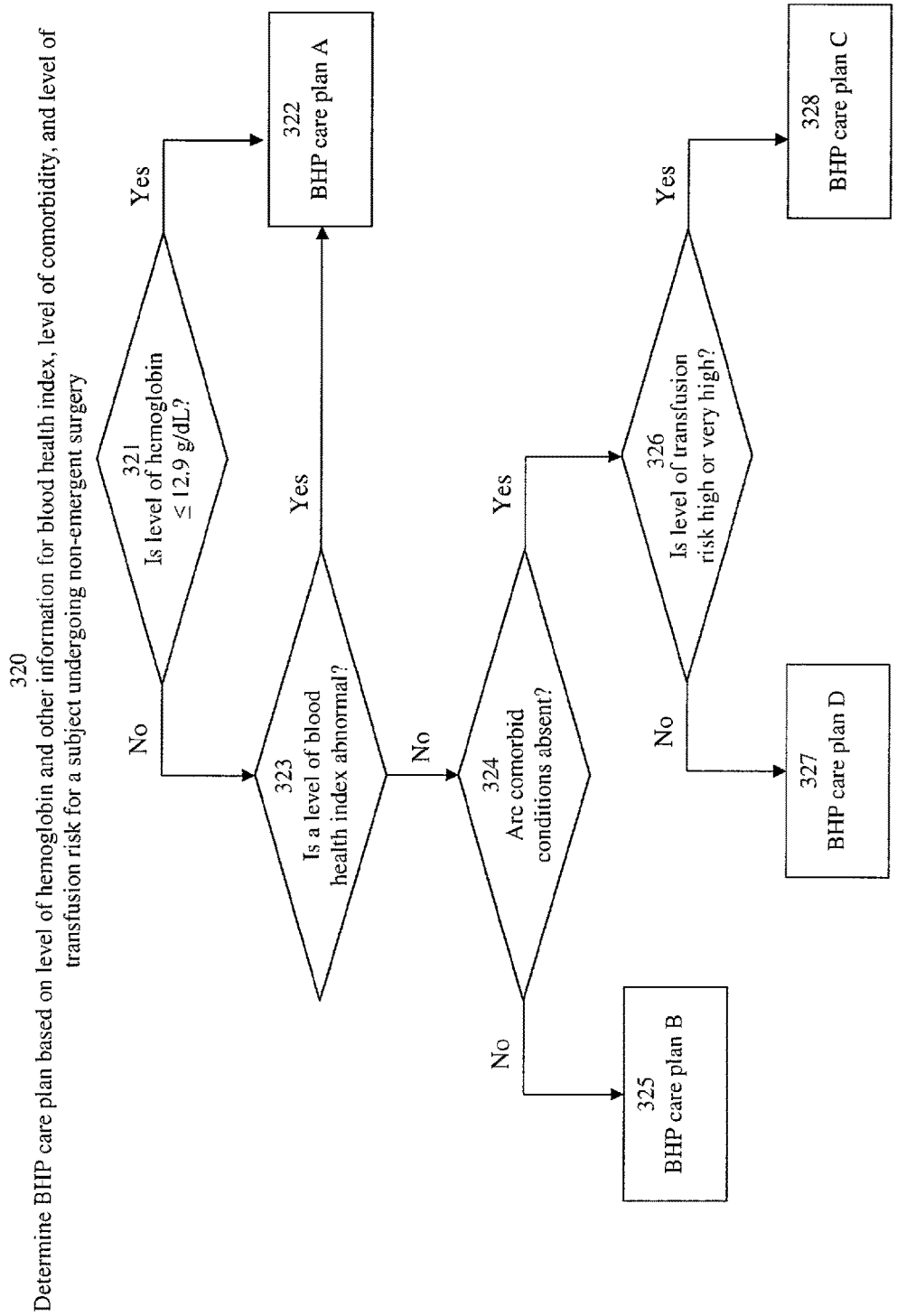
FIGS. 3A-3C are flowcharts of a non-limiting embodiment for determining BHP special care plans in a subject undergoing non-emergent surgery (FIG. 3A) or a subject having a chronic disease (FIGS. 3B-3C).

FIG. 3A is a flow diagram showing a non-limiting embodiment of determining a preoperative BHP care plan based on level of hemoglobin and other information for blood health index, level of comorbidity, and level of transfusion risk 320. Information about the level of hemoglobin is used to determine whether the subject is anemic or not 321. For example, a subject is anemic if the level of hemoglobin is less than or equal to 12.9 g/dL (or another predetermined threshold, e.g., 13.4 g/dL). A subject is also anemic if one or more levels of a blood health index is abnormal 323, such as one or more abnormal levels characterized a predetermined threshold of a serum iron level <35 µg/dL, % iron saturation <25%, MCV <82 fL, MCV >100 fL, MCH <30 pg, ferritin <125 ng/mL, or C reactive protein (i) >8 mg/L. If the subject is anemic, iron-depleted, or iron-deficient, then the subject is provided with patient care plan A 322, which addresses these issues. In another embodiment, if the subject is anemic, then the level of comorbidity is determined to determine a care plan. As described below, the care plan would be one that addresses issues relating to this extent of comorbidity.

Specific examples of outpatient and inpatient BHP care plan A might include administration of oral iron (e.g., with or without ascorbic acid) or intravenous iron (e.g., ferric carboxymaltose, iron sucrose (Venofer®), or iron dextran (InFeD®)); administration of ascorbic acid, folate, or vitamin B12; administration of erythropoietic medications, such as, but not restricted to, erythropoietin, epoetin, epoetin alfa, darbepoetin alfa, epoetin delta, PDpoetin, or methoxy polyethylene glycol-epoetin beta; use of a cell saver; use of pediatric blood tubes for blood draws; preoperative autologous blood donation; or acute normovolemic hemodilution. If the subject is not anemic, then the level of comorbidity is determined to assess possible risks of complications during surgery 323.

Effect of Hemoglobin on Care Plan for Chronic Disease

Figure 3B:
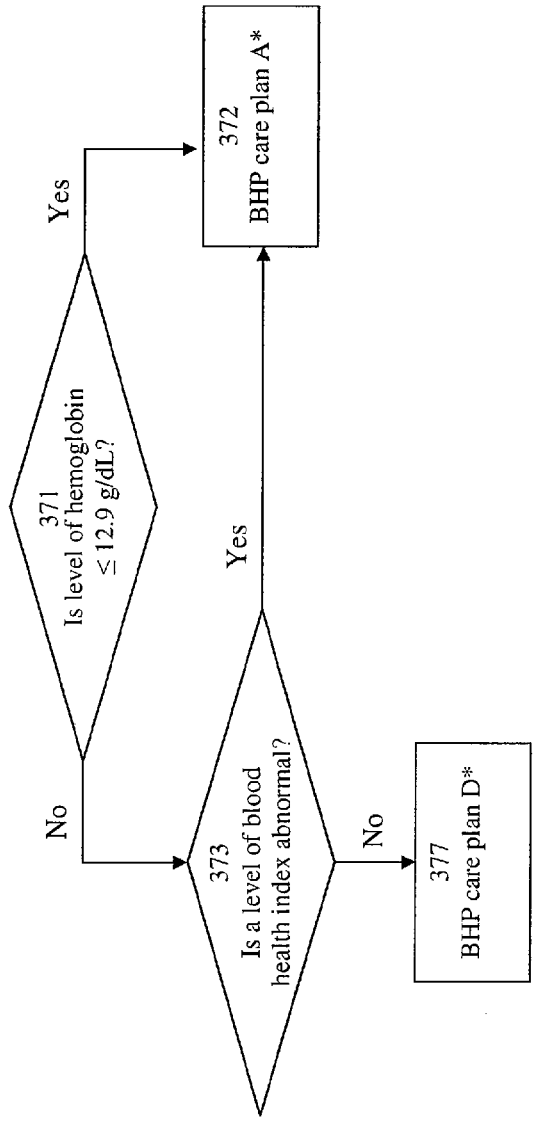

Anemia, as determined by level of hemoglobin or another abnormal test value, as described above, can be treated in a subject having a chronic disease, as shown in FIG. 3B. Information about the level of hemoglobin and other information for blood health index are used to determine whether the subject is anemic or not 370. For example, a subject is anemic if the level of hemoglobin is less than or equal to 12.9 g/dL 371. Using the WHO criteria, the subject is anemic if the level of hemoglobin is less than or equal to 12.9 g/dL if male and 11.9 g/dL if female. A subject is also anemic if one or more levels of a blood health index is abnormal 373, such as one or more abnormal levels characterized by a serum iron level <35 µg/dL, % iron saturation <25%, MCV <82 fL, MCV >100 fL, MCH <30 pg, ferritin <125 ng/mL, or C reactive protein (i) >8 mg/L. If the subject is anemic, then the subject is provided with patient care plan A\* 372, which addresses anemia or issues that arise due to anemia. Specific examples of outpatient and inpatient BHP care plan A\* might include administration of oral iron with ascorbic acid or intravenous iron (e.g., ferric carboxymaltose, iron sucrose (Venofer®), or iron dextran (InFeD®)); administration of ascorbic acid, folate, or vitamin B12; and/or administration of erythropoietic medications, such as, but not restricted to, erythropoietin, epoetin, epoetin alfa, darbepoetin alfa, epoetin delta, PDpoetin, or methoxy polyethylene glycol-epoetin beta. If the subject is not anemic, then the subject is provided with patient care plan D\*, which can include no further treatment for anemia or include administration of oral iron with ascorbic acid and/or a multivitamin.

Further assessment of subjects having chronic diseases or conditions include scoring assessments for quality of life and physical function, such as heart failure-specific questionnaires (e.g., the Minnesota Living with Heart Failure Questionnaire (MLWHFQ) or the Kansas City Cardiomyopathy Questionnaire (KCCQ)), general quality of life questionnaires (e.g., a Patient Global Assessment test or European Quality of Life-5 Dimensions test), and heart function tests (e.g., the 6 minute walk test or the New York Heart Association functional class). The results of these assessments can be included in a patient outcome report, as described herein.

Effect of Comorbidity on Care Plan

In FIG. 3A, subjects who have one or more comorbid conditions are provided with patient care plan B 324, which addresses issues relating to this level of comorbidity. Specific examples of patient care plan B include those that address that level of comorbidity or those that address that particular comorbid condition. For example, a comorbid condition may indicate a care plan that strictly minimizes blood loss, such as by using pediatric blood tubes for blood draws, and the presence of cardiovascular disease as a particular comorbid condition may further indicate a care plan that includes transfusion of fresh (e.g., less than 10 days old) allogeneic red cells, if transfusion is needed. In another example, the presence of renal disease as a particular comorbid condition may further indicate a care plan that includes preoperative dialysis and administration of desmopressin acetate (DDAVP®). Further examples of care plans relating to particular comorbidities are described herein.

Effect of Level of Transfusion Risk on Care Plan

If the subject has no comorbid conditions and no anemia, then the level of transfusion risk is determined to assess possible risks of a transfusion during surgery 325. Subjects who have a high or very high level of transfusion risk are provided with patient care plan C 327, which addresses this level of transfusion risk. Specific examples of patient care plan C can include use of a cell saver; use of pediatric blood tubes for blood draws; or acute normovolemic hemodilution. Generally, preoperative autologous blood donation is not recommended, unless the subject cannot readily receive an acceptable transfusion product (e.g., the subject's blood contains multiple red cell antibodies). Subjects who have a low or intermediate level of transfusion risk are provided with patient care plan D 326. As the subject has a low risk of transfusion during or after the surgery, patient care plan D will generally include administration of oral iron with ascorbic acid and/or a multivitamin prior to the surgery.

Effect of Level of Bleeding Risk on Care Plan

Referring to FIG. 2A, the level of bleeding risk can be determined 212 by any useful combination of predetermined bleeding risk conditions that indicates an increased risk of bleeding for a subject during surgery. Specific examples of predetermined bleeding risk conditions include whether the subject has a history of abnormal coagulopathy, such as hemophilia A or B, von Willebrand disease, liver disease, or vitamin K deficiency; whether the subject has a past history of bleeding; or whether the subject takes one or more procoagulant medications, such as a zeolite, desmopressin, a coagulation factor (e.g., factor VII), tranexamic acid, aminocaproic acid, or aprotinin.

The level of bleeding risk can be determined by history of bleeding, such as inherited or prior history of bleeding; medication-related bleeding; or the presence of a renal disease, as discussed herein. History of bleeding can be determined in any useful way, such as by using a questionnaire (see, e.g., Seeber and Shander, "Basics of Blood Management," Blackwell Publishing, 2007, p. 335) or by reviewing medical history (see, e.g., Chee et al., *Br. J. Haematol.* 140: 496-504 (2008)).

Figures 1, 8I:
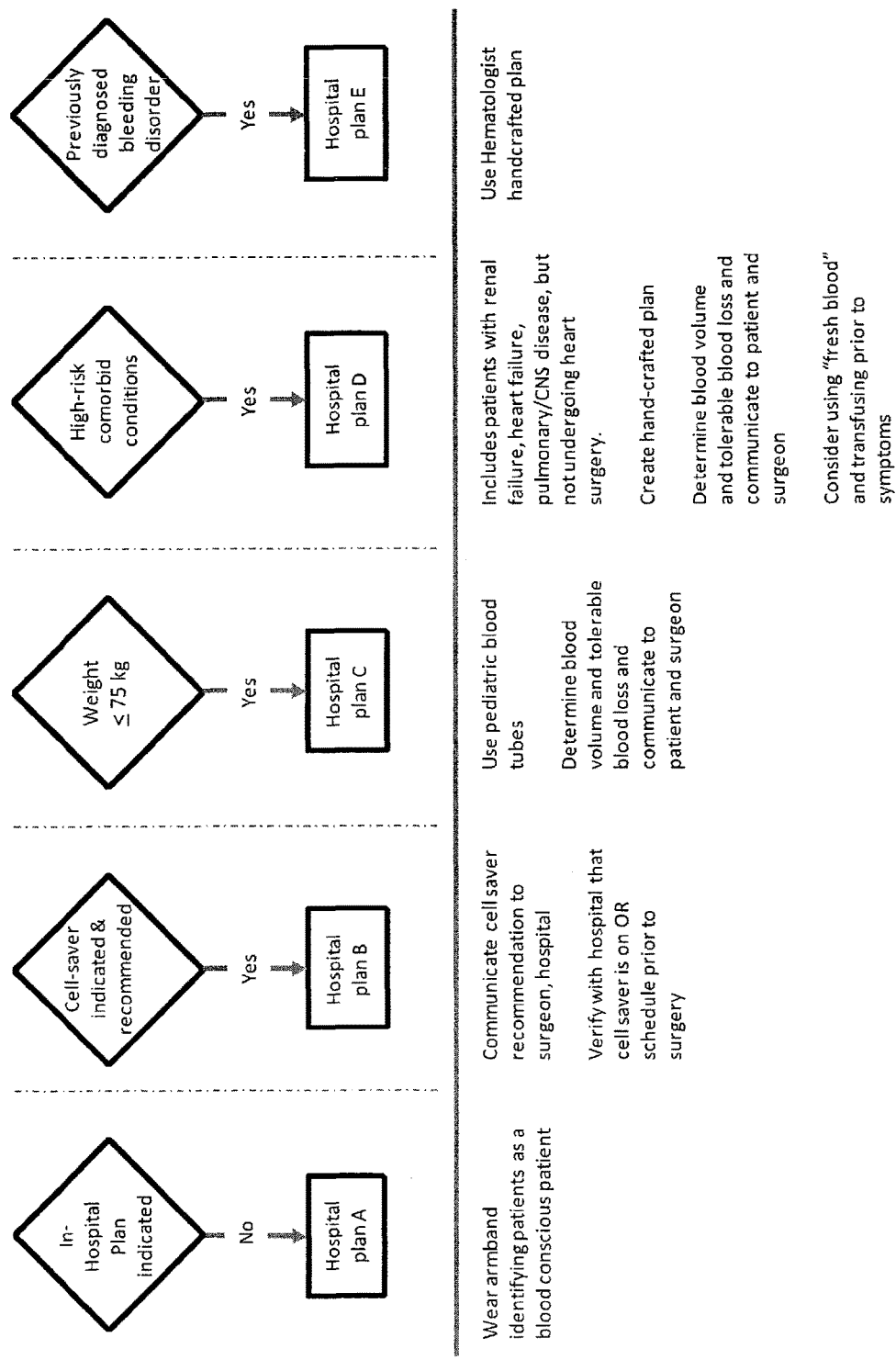
Figures 2, 8I:
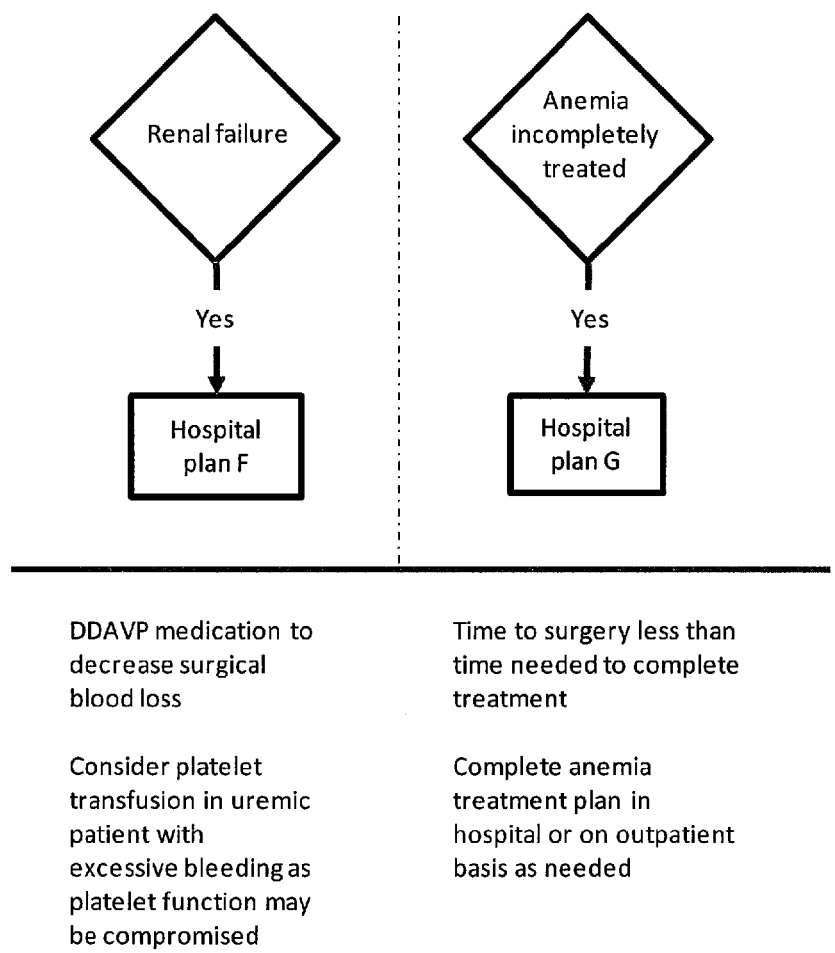

If there is a previous diagnosis of bleeding disorder, then the subject can be further asked about their hematologist and referred back to their hematologist for an in-hospital transfusion minimization care plan (e.g., hospital plan E in FIG. 8I-1 or special plan 3 in FIG. 8H-2). If the subject's history or patient questionnaire shows abnormalities but no previously diagnosed bleeding problem, then coagulation studies are done (e.g., International Normalized Ratio (INR), partial thromboplastin time (PTT), or fibrinogen with reflex to coagulation factor assays, if indicated). If laboratory results are abnormal, then either the patient is handed back to their primary care doctor to get a hematologist involved or the transfusion management healthcare provider provides a hematologist consult by telemedicine for an in-hospital transfusion minimization care plan (e.g., special plan 3 in FIG. 8H-2 or hospital plan E in FIG. 8I-1).

First Test Panel Based on Profile and Level of Bleeding Risk

Also shown in FIG. 2A is a first test panel, which is determined based on the profile and the level of bleeding risk 221. The first test panel can be based on any information of the profile. For example, the first test panel can be based on the level of hemoglobin and the level of creatinine.

When based on the level of hemoglobin, this first test panel includes one or more laboratory tests that would be performed to more accurately assess the level of hemoglobin or the cause of the abnormal level of hemoglobin or to more recently determine the level of hemoglobin. Specific examples of laboratory tests include one or more of a complete blood count (e.g., with reticulocyte count, platelet count, white blood cell (WBC) count, red blood cell (RBC) count, a hemoglobin (Hgb) test, a hematocrit (Hct) test, mean corpuscular volume (MCV), mean corpuscular hemoglobin (MCH), mean corpuscular hemoglobin concentration (MCHC), and red cell distribution width (RDW)), complete iron studies (e.g., serum iron, transferrin, % iron saturation (or % saturation of transferrin by iron), total iron binding capacity, and ferritin), a hemoglobin (Hgb) test, a vitamin B12 test, and a folate test. Further additional tests for the first test panel include a reticulocyte count, a platelet count, a WBC count, serum iron, iron binding capacity, % iron saturation (or % saturation of transferrin by iron), a ferritin assay, a C reactive protein (inflammatory, non-cardiac) assay, a creatinine test, a glomerular filtration rate (GFR) test, a creatinine test with GFR, a methylmalonic acid (MMA) test, red cell antibody screen, a red cell antibody screen, a red cell antibody identification test, a direct antiglobulin test, an indirect antiglobulin test, a red cell antigen typing test (e.g., ABO and/or Rh), a transferrin assay, a soluble transferrin receptor assay, a hepcidin assay, an interleukin-6 assay, and a reticulocyte hemoglobin concentration assay.

When based on the level of creatinine, this first test panel includes one or more laboratory tests that would be performed to more accurately assess the level of creatinine or to more recently determine the level of creatinine. Specific examples of laboratory tests include one or more of a creatinine test with calculated glomerular filtration rate and a blood urea nitrogen test.

The first test panel can also be based on the time at which any information of the profile was obtained. For example, although medical records will typically have some information about the results from some laboratory studies, more recent laboratory values may be needed to reflect the subject's current medical state. Therefore, the first test panel can also include laboratory tests in order to obtain current information about the subject (e.g., within 72 hours, one week, two weeks, three weeks, or one month). Specific examples of laboratory tests for more recent or current information include one or more of a hemoglobin test, creatinine test, or a red cell antibody screen.

When the first test panel is based on level of bleeding risk, the first test panel includes one or more laboratory tests that would be performed to more accurately assess bleeding risk. Specific examples of laboratory tests include a screening coagulation panel, which can include one or more of a complete blood count with differential and platelet count, prothrombin time with international normalized ratio, activated partial thromboplastin time, bleeding time, factor VIII clotting activity, or plasma fibrinogen level; a lupus anticoagulant assay, including mixing studies; or a special coagulation test, which can include one or more of a platelet aggregation assay, D-dimer assay, tissue plasminogen activator antigen assay, von Willebrand factor antigen assay, assays for specific factors (e.g., factors II, V, VII, VIII, IX, X, XI, and XII), alpha-2-antiplasmin assay, plasminogen activator inhibitor-1 assay, anticardiolipin antibody ELISA, platelet secretion assay, protein C activity assay, or antithrombin III activity assay.

The patient care plan(s) can be modified to account for level of bleeding risk. For example, if there is a high level of bleeding risk or an abnormal result from the first test panel, then a specialist in hematology can be consulted to further determine a patient care plan for the subject (e.g., FIG. 8F).

When the level of bleeding risk is based a history of bleeding that is not apparently medication related, the first test panel can include additional coagulation tests, such as activated partial thromboplastin time, prothrombin time with international normalized ratio, and plasma fibrinogen level. The first test panel can also include authorization to add on additional tests if abnormalities are detected, where additional tests can include a lupus anticoagulant assay, mixing studies, an assay for specific factors, and other studies as need be determined. When the level of bleeding risk is medication-related, no additional tests may be required (e.g., FIG. 8F).

First Test Panel and Patient Care Plans Based on Profile for Chronic Disease

Figure 3C:
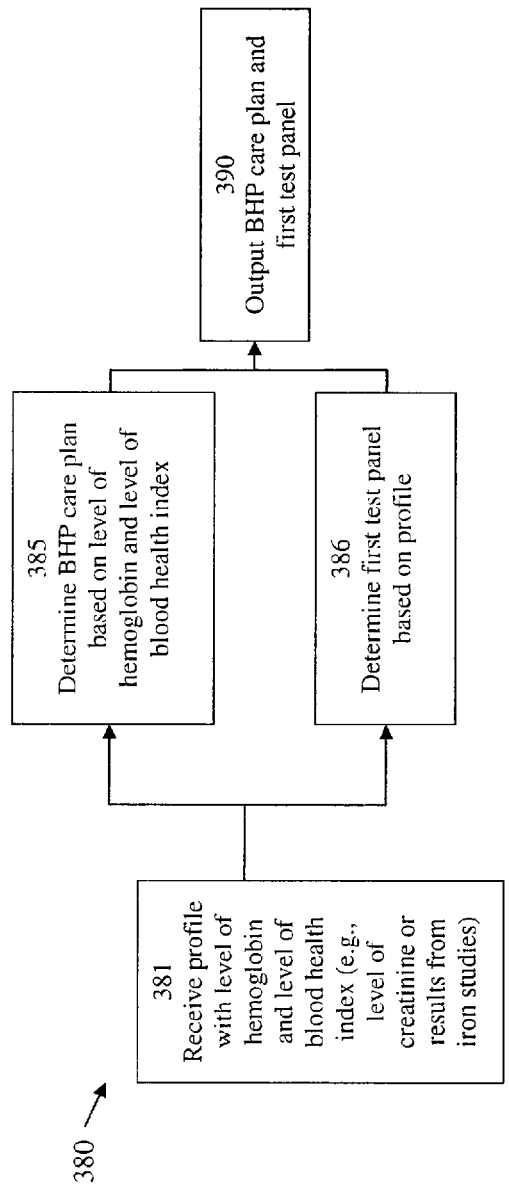

FIG. 3C is a flowchart of an exemplary method of treating a subject having a chronic disease by using a blood health preparedness ("BHP") protocol 380 and a first test panel. First, a profile is received 381. Then, a BHP care plan 385 and first test panel 386 is determined based on the profile 386. Finally, the protocol includes outputting the care plan and the test panel 390.

The first test panel can be based on any information of the profile (e.g., the level of hemoglobin or level of blood health index, as described herein). For example, if the level of hemoglobin or level of blood health index indicates anemia, as described herein, then the first test panel includes one or more tests selected from the group consisting of a creatinine test, glomerular filtration rate, a vitamin B12 test, and a folate test.

FIG. 3C also shows outputting a BHP patient care plan for a subject with a chronic disease. The care plan can be determined based on any information of the profile (e.g., the level of hemoglobin or level of blood health index, as described herein). For example, the care plan can be determined based on level of hemoglobin to indicate whether a subject is anemic or the results from iron studies to indicate whether the subject is iron-depleted or iron-deficient. Accordingly, the care plan would include one or more medication to treat anemia (e.g., intravenous iron or epoetin) or iron-depletion or iron-deficiency (e.g., ferric carboxymaltose, iron sucrose (Venofer®), iron dextran (InFeD®), erythropoietin, folate, vitamin B12, epoetin, epoetin alfa, darbepoetin alfa, epoetin delta, PDpoetin, or methoxy polyethylene glycol-epoetin beta). Further exemplary patient care plans are also described herein.

Exemplary Patient Care Plans Based on Information in Profile

Figure 4:
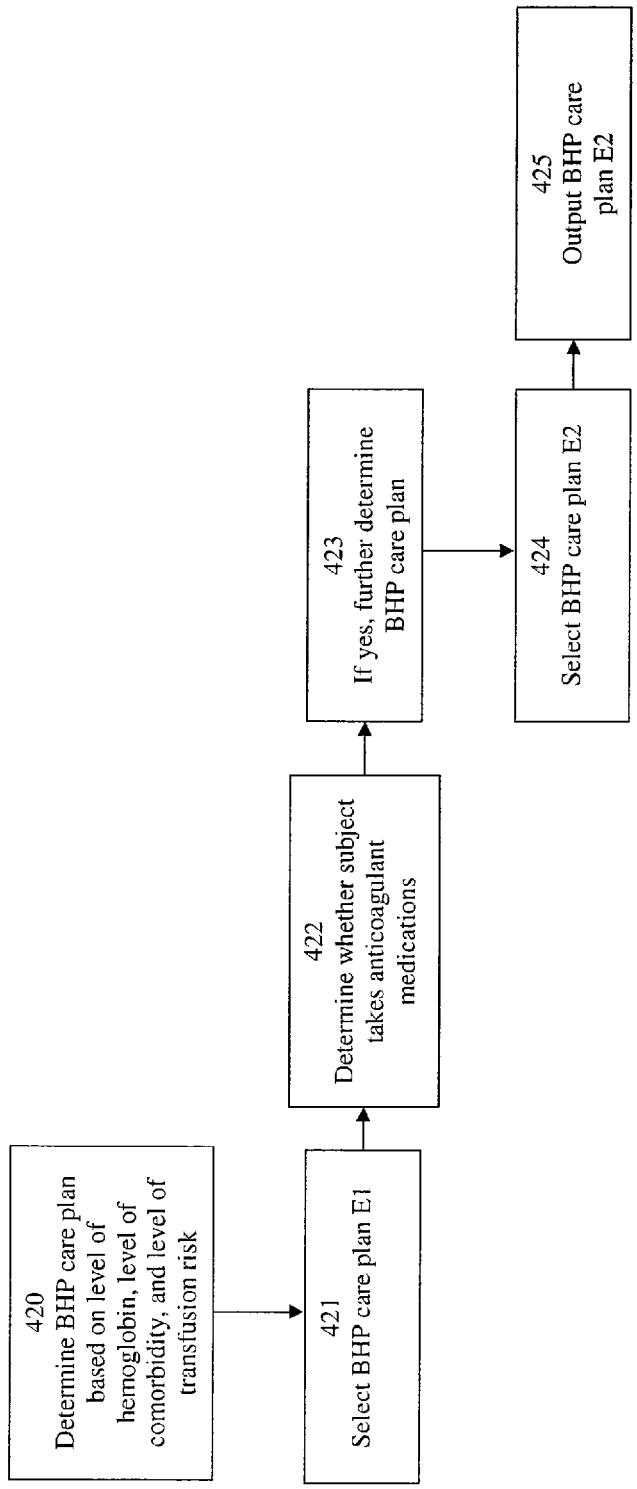
FIG. 4 is a flowchart of a non-limiting embodiment for further determining a BHP special care plan.
Figure 5:
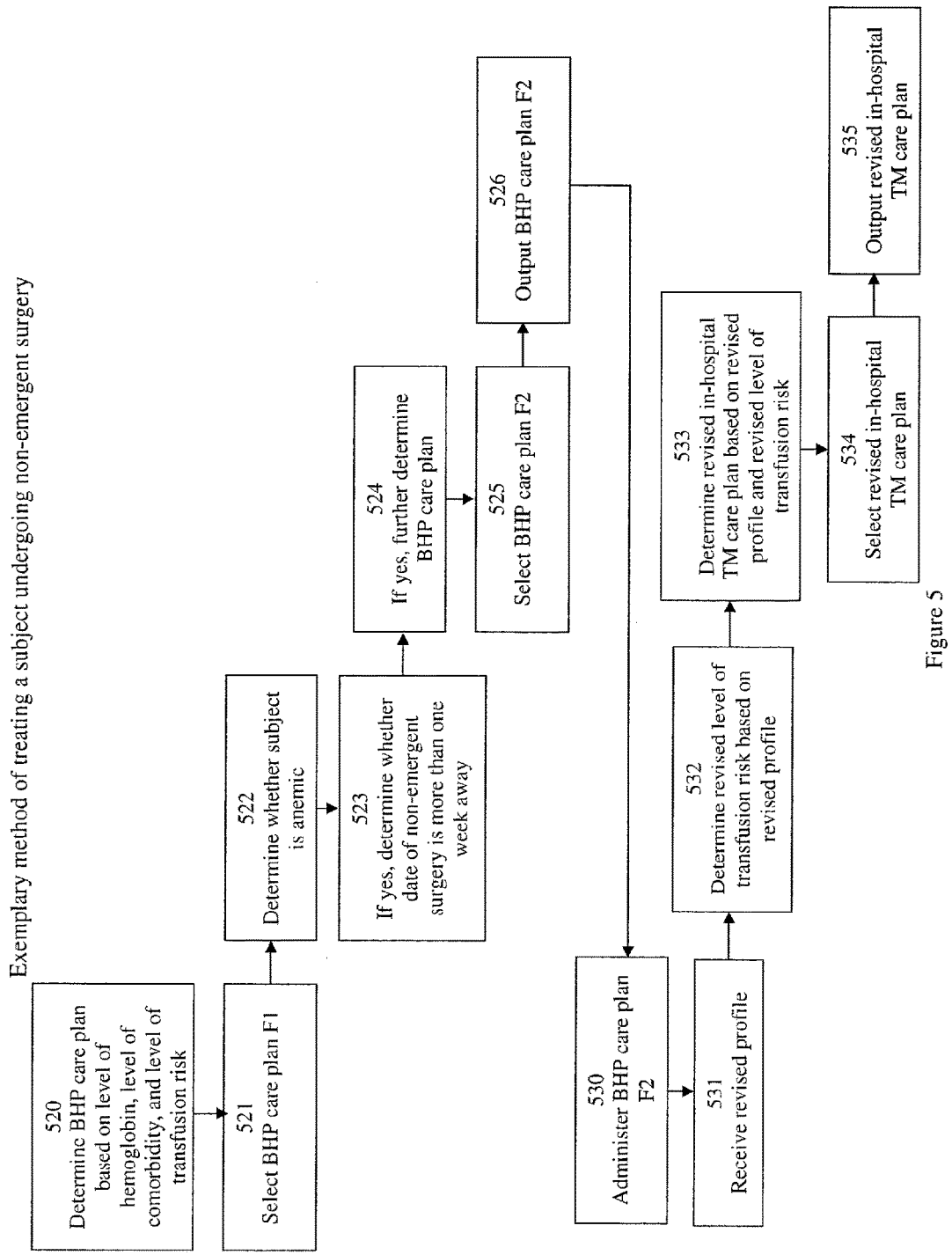
FIG. 5 is a flowchart of a second non-limiting embodiment for further determining a BHP care plan.

The patient care plan can include further determinations based on information available in the profile, such as shown in FIGS. 4 and 5. FIG. 4 shows a non-limiting embodiment of further determining an outpatient BHP care plan based on information regarding whether the subject takes one or more anticoagulant medications. First, the BHP protocol has been performed to determine 420 and select 421 patient care plan E1, which can be any patient care plan described herein. Then, information regarding the subject is used to determine whether the subject takes one or more anticoagulant medications 422. If the subject takes one or more anticoagulant medications 423, then the patient care plan is further determined to select 424 and output 425 patient care plan E2. Patient care plan E2 includes the treatment provided in patient care plan E1 and further includes any other treatment that addresses the information that the subject takes one or more anticoagulation medications. For example, if patient care plan E1 indicates that the subject takes oral iron, then patient care plan E2 indicates that the subject takes oral iron and that the subject discontinues one or more anticoagulation medications between about one week or two weeks before the date of the non-emergent surgery. Examples of anticoagulation medications include vitamin K antagonists, such as warfarin, acenocoumarol, or phenindione; heparins, such as low molecular weight heparin and pentasaccharide inhibitors; or direct thrombin inhibitors, such as argatroban, lepirudin, bivalirudin, and dabigatran. The step of determining whether the subject takes one or more anticoagulant medications 422 can optionally include determining the conditions for which these medications are being taken. Then, these conditions can be compared with the level of comorbidity or presence of a particular comorbid condition. This optional step could be used to determine increased risk associated with anemia treatment.

FIG. 5 shows a second non-limiting embodiment of further determining a patient care plan based on information regarding whether the subject is anemic. First, the BHP protocol has been performed to determine 520 and select 521 patient care plan F1, which can be any patient care plan described herein. Then, information regarding the subject is used to determine whether the subject is anemic 522. If the subject is anemic, then the date of the non-emergent surgery is applied to determine whether the surgery is more than one week away 523. After determining whether the surgery is more than one week away 523, the protocol may further include determining the level of comorbidity (not shown). If the surgery is more than one week away 524, then the patient care plan is further determined to select 525 and output 526 patient care plan F2. In an alternative embodiment, patient care plan F2 is determined based on whether or not there is sufficient time to implement the patient care plan. Though FIG. 5 shows that the surgery is more than one week away, other time periods can be used (e.g., more than two weeks away or between one or two weeks away).

Patient care plan F2 includes the instructions provided in patient care plan F1 and further includes another care plan that addresses anemia. For example, if patient care plan F1 indicates that the subject is a smoker, then patient care plan F1 indicates that the subject receives information to quit smoking and patient care plan F2 indicates that the subject takes oral iron with ascorbic acid, intravenous iron, and/or an erythropoietic medication to treat anemia. Examples of medications include, but are not restricted to, iron (e.g., oral iron with or without ascorbic acid or intravenous, such as ferric carboxymaltose, iron sucrose (Venofer®), iron dextran (InFeD®)), ascorbic acid, folate, vitamin B12, and erythropoietic medication (e.g., erythropoietin, epoetin, epoetin alfa, darbepoetin alfa, epoetin delta, PDpoetin, or methoxy polyethylene glycol-epoetin beta). After patient care plan F2 is administered to the subject before the date of the surgery 530, a revised profile is received 531. The revised profile includes information about the subject after having been administered the patient care plan. A revised level of transfusion risk is determined based on the revised profile 532, where the revised level of transfusion risk can be determined by any method described herein for determining level of transfusion risk. Then, the level of transfusion risk is applied to determine 533, select 534, and output 535 a revised patient care plan for inpatient care.

Transfusion Minimization Protocol

Figure 6:
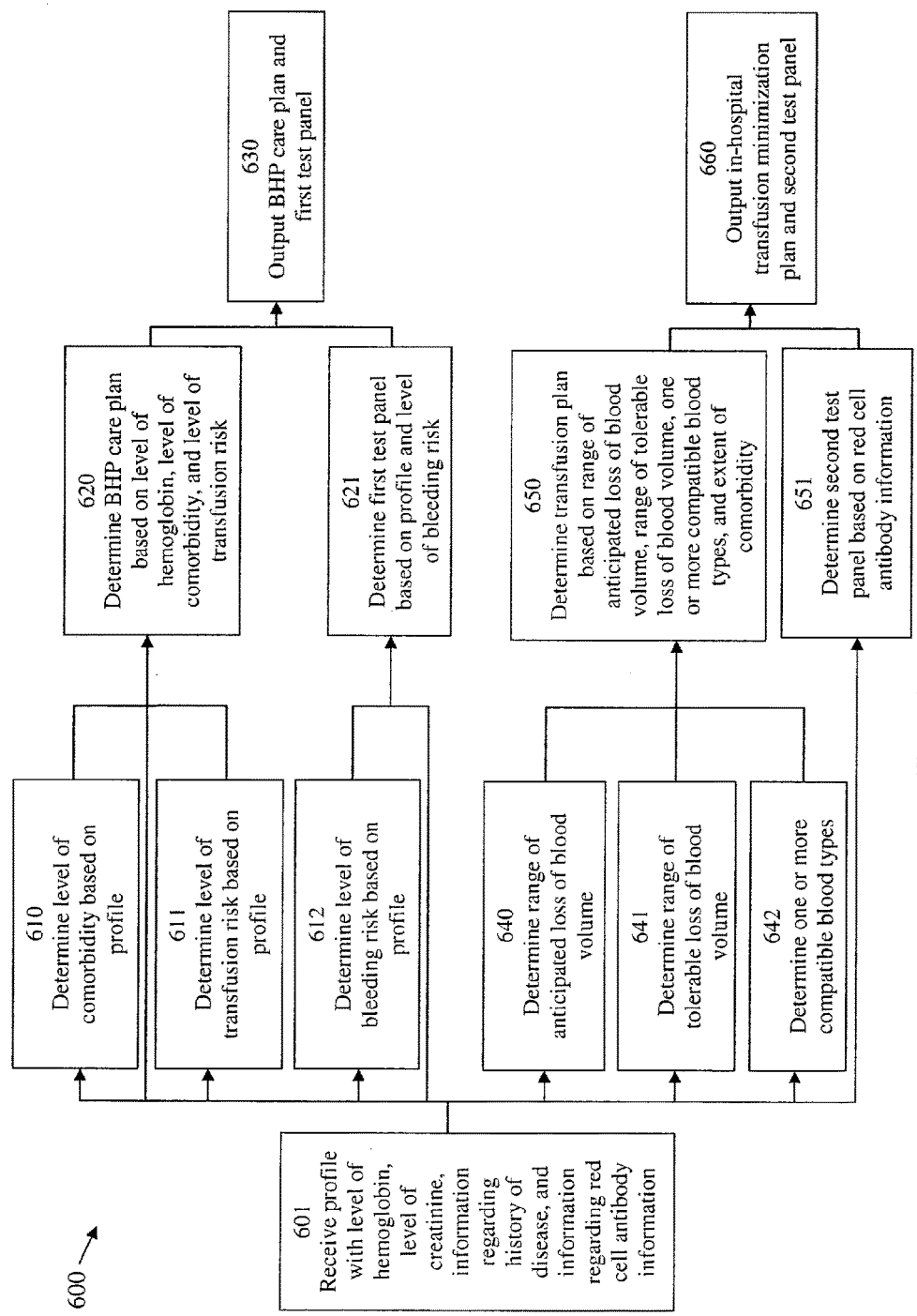
FIG. 6 is a flowchart of a second exemplary method of reducing transfusions by determining a preoperative BHP and an in-patient transfusion minimization ("TM") care plan.

The blood health management program can further comprise an in-hospital transfusion minimization protocol, including in-hospital TM plans (e.g., hospital plans A-G in FIGS. 8F-1 and 8F-2) or one or more test panels. FIG. 6 shows a further embodiment for a blood health management program 600 to output a BHP care plan, a first test panel, an in-hospital transfusion minimization care plan, and a second test panel. Briefly, the method 600 comprises receiving a profile 601, determining various levels of risk based on the profile 610-612, determining a preoperative BHP care plan 620 and a first test panel 621, outputting the BHP care plan and first test panel 630, determining various parameters based on the profile 640-642, determining an in-hospital transfusion minimization care plan 650 and a second test panel 651, and outputting the in-hospital transfusion minimization care plan and the second test panel 660.

The in-hospital transfusion minimization care plan(s) can include any information or treatment helpful for avoiding unnecessary or excessive allogeneic blood transfusion, determining when and what volume to transfuse, and administering a transfusion product. In FIG. 6, information from the profile is used to determine a range of anticipated loss of blood volume 640, a range of tolerable loss of blood volume 641, and one or more compatible blood types 642. The in-hospital transfusion minimization care plan(s) are determined based on a range of anticipated loss of blood volume, a range of tolerable loss of blood volume, one or more compatible blood types, and level of comorbidity 650. The in-hospital transfusion minimization care plan can be one or more any useful treatments that would address the determined range of anticipated loss of blood volume, a range of tolerable loss of blood volume, one or more compatible blood types, or level of comorbidity. For example, the in-hospital transfusion minimization care plan can provide when to transfuse the subject during surgery (e.g., after the subject has lost blood in excess of the range of tolerable loss of blood volume), what kind of transfusion product to be used (e.g., a transfusion product of one or more compatible blood types), or how much of the transfusion product to be used (e.g., an amount equal to the range of anticipated loss of blood volume). The in-hospital transfusion minimization care plan can be administered during a non-emergent surgery or on days following the non-emergent surgery.

The range of anticipated loss of blood volume can be determined by any useful method. For example, the range of anticipated loss of blood volume can be determined by statistical analysis of blood loss in previous patients undergoing a similar type of surgery. Anticipated loss can also depend on the surgeon performing the surgery. Therefore, the predetermined range of anticipated loss of blood volume can be determined from compiling a data set having measured loss of blood volumes for a particular surgery and/or a particular surgeon. Exemplary estimates of anticipated loss of blood volume include 2,000 mL-2,500 mL for cardiovascular surgery, 1,000 mL-3,000 mL for spinal surgery, and 500 mL-2,500 for hip and knee arthroplasty. Additional methods are described in Palmer et al., *Anesth. Analg.* 96:369-375 (2003); and McIvor, Establishing a Heart Failure Program: The Essential Guide, pp. 147 and 157 (3d ed., Blackwell Publishing, 2007), which are incorporated herein by reference.

The range of tolerable loss of blood volume can be determined by any useful method, such as by calculating the amount of blood volume that can be lost while maintaining sufficient minimum tolerable hematocrit within the subject. Generally, acute loss of blood volume of about 20% is tolerable for hematocrit of 21%-24% tolerated by males and females without significant comorbid conditions, such as active cardiovascular disease, and for hematocrit of 24%-30% considered reasonable for males and females with active cardiovascular disease. Exemplary methods are described in Singbartl et al., *Anesth. Analg.* 96:929-935 (2003); Gross, *Anesthesiology* 58:277-280 (1983); and Bourke et al., *Anesthesiology* 41:609-612 (1974). For example, tolerable loss of blood volume can be calculated from the following equation, where tolerable loss of blood volume=(blood volume×actual hematocrit)−(blood volume×minimum tolerable hematocrit). In another example, a minimum tolerable hematocrit associated with a level of comorbidity is 33% to 36% for a high level of comorbidity and 18% to 30% for a low level of comorbidity. Generally, lower levels of comorbidity (i.e., healthier patients) are associated with lower levels of minimum tolerable hematocrit because healthier patients can tolerate post-surgical anemia more so than patients having various comorbid conditions.

In-Hospital Transfusion Minimization Care Plan

Subjects who have one or more comorbid conditions are provided with an in-hospital transfusion minimization care plan that addresses this condition (e.g., hospital plan D in FIG. 8I-1). For example, a comorbid condition due to the presence of recent or past history of a myocardial infarction or heart disease results in an in-hospital transfusion minimization care plan that uses blood components that are less than 10 days old and transfuses patients at a higher hemoglobin threshold than patients without recent significant and active cardiac disease. In another example, a comorbid condition due to the presence of renal disease results in an in-hospital transfusion minimization care plan that indicates transfusing platelet components in addition to red cells should excessive bleeding occur during the surgery. The in-hospital transfusion minimization care plan(s) can include any useful method(s) to minimize blood loss, such as those described in Stainsby et al., *Br. J. Haematol.* 135: 634-641 (2006).

The in-hospital transfusion minimization care plan is also based on determining one or more compatible blood types. Approximately 5% of all patients will have antibodies to one or more common red cell antigens. Compatible blood components should be obtained or inventoried prior to the day of surgery (e.g., preoperative BHP special care plan 4 in FIG. 8H-2). If a patient with red cell antibodies is also anemic, then an in-hospital transfusion minimization care plan should be determined prior to the day of the surgery. Exemplary in-hospital transfusion minimization care plans for this anemic subject include testing blood from a family member, followed by donation by that family member; importing of rare units from select blood centers; or use of a cell saver during surgery, if the surgery type is appropriate for use of cell saver (e.g., see FIG. 8C). Exemplary blood typing tests include ABO and Rh typing, or a red blood cell antibody screen with antibody identification test, if the screen is positive. Other useful methods with respect to blood typing are described in Chapman et al., *Transfusion Medicine* 14: 59-73 (2004).

The transfusion product can be any useful composition that could be administered by a healthcare provider for a transfusion. The transfusion product can include one or more blood components in any useful combination. Specific examples of blood components include red blood cells, including hemoglobin; white blood cells; clotting factors; immunoglobulins; platelets; plasma; or plasma protein fractions, including albumin or fibrinogen (e.g., cryoprecipitate). The blood components and transfusion product can be obtained from any source, such as autologous, allogeneic, or synthetic sources. The transfusion product can optionally include one or more of salts, such as magnesium, calcium, or sodium salts; or cryoprotective agents, such as glucose, dimethylsulfoxide, or hydroxyethyl starch. Specific examples of blood substitutes include perfluorocarbons, such as Oxycyte®; or hemoglobin-derived products, such as Hemopure®. The transfusion product can be formed by any combination of blood components, buffers, salts, or blood substitutes in any useful ratio. The transfusion product can be of any useful shelf age. For example, some in-hospital transfusion minimization care plans may require a transfusion product that is less than 10-14 days old rather than towards the end of the 42 day shelf life.

Second Test Panel Based on Red Cell Antibody Information

As shown in FIG. 6, the blood health management program 600 further comprises determining a second test panel based on red cell antibody information 651. If the red cell antibody information includes the presence of one or more red cell antibodies, then the second test panel includes one or more laboratory tests that identify the one or more red cell antibodies. Specific examples of such laboratory tests include a red cell antibody identification test, a direct antiglobulin test, an indirect antiglobulin test, and a red cell antigen typing test (e.g., ABO and/or Rh).

Effect of Level of Renal Risk

Figure 7A:
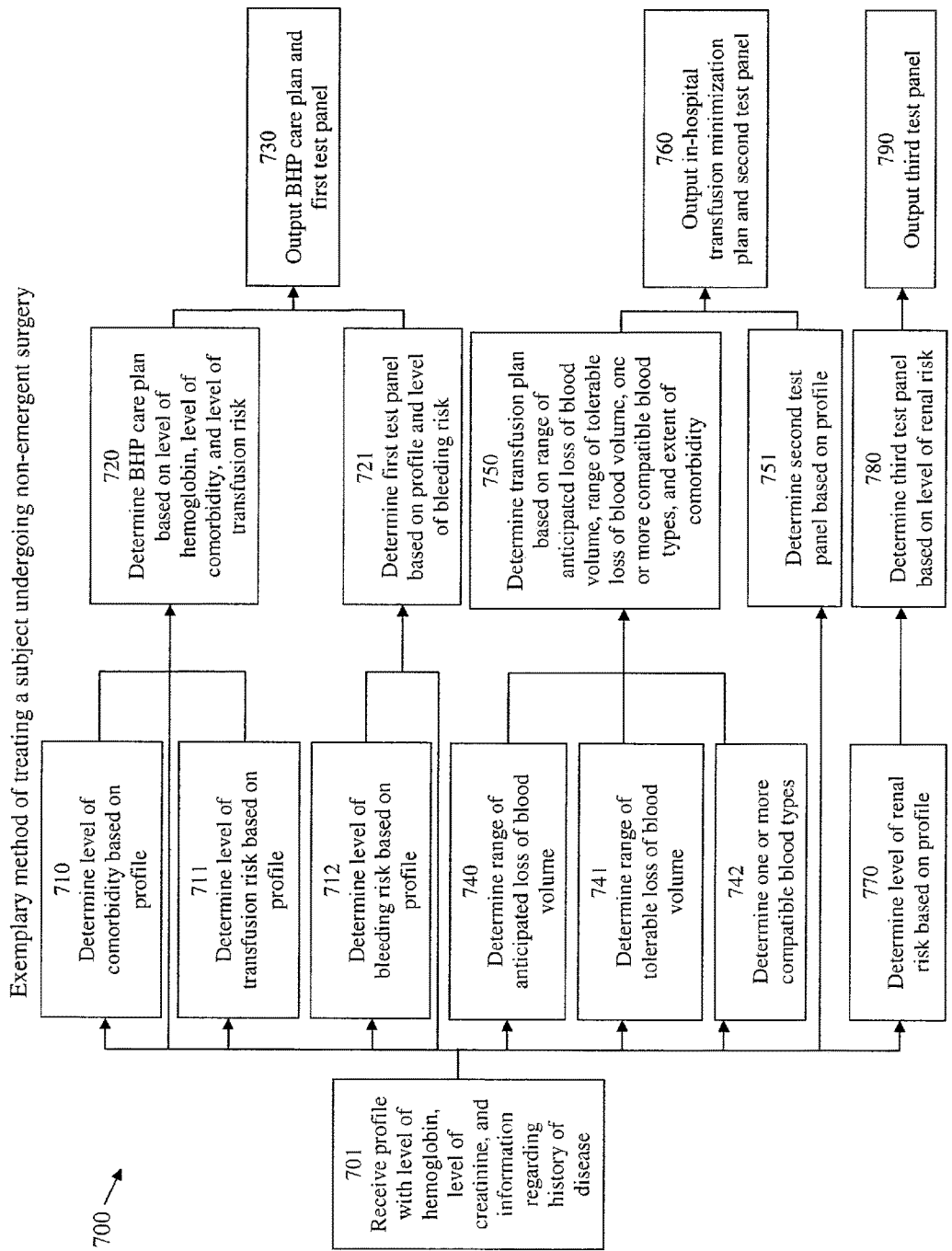
FIGS. 7A-7E are flowcharts of a third exemplary method of reducing transfusions by determining a preoperative BHP care plan, an in-patient transfusion minimization plan, and a third test panel (FIG. 7A).

FIG. 7A shows a further embodiment for a blood health management program 700 to output a BHP care plan, a first test panel, an in-hospital transfusion minimization care plan, a second test panel, and a third test panel. Briefly, the method 700 comprises receiving a profile 701, determining various levels of risk based on the profile 710-712, determining a BHP care plan 720 and a first test panel 721, outputting the BHP care plan and first test panel 730, determining various parameters based on the profile 740-742, determining an in-hospital transfusion minimization care plan 750 and a second test panel 751, outputting the in-hospital transfusion minimization care plan and the second test panel 760, determining a level of renal risk 770, determining a third test panel 780, and outputting the third test panel 790.

The level of renal risk can be determined 770 by any useful combination of risk factors that indicates evidence of renal dysfunction prior to the non-emergent surgery. Specific examples of risk factors include whether the subject has a current or past history of renal disease or diabetes. This third test panel based on renal risk 780 includes one or more laboratory tests that would be performed to more accurately assess renal risk. Specific examples of laboratory tests include a creatinine test, a blood urea nitrogen test, and/or a glomerular filtration rate. There are several implications of increased renal risk for a BHP care plan or in-hospital transfusion minimization care plan. For example, increased renal risk typically indicates increased risk of bleeding, where the patient care plan can include dialysis prior to surgery and/or administration of a vasopressin analogue, such as desmopressin acetate (DDAVP®). In further examples, if the level of renal risk is high, then the patient care plan further comprises a consultation with a renal specialist, and wherein if the level of creatinine is more than 2 mg/dL, then the patient care plan further comprises dialysis.

Effect of Renal Risk on BHP Care Plan for Subject with Chronic Disease

Figure 7B:
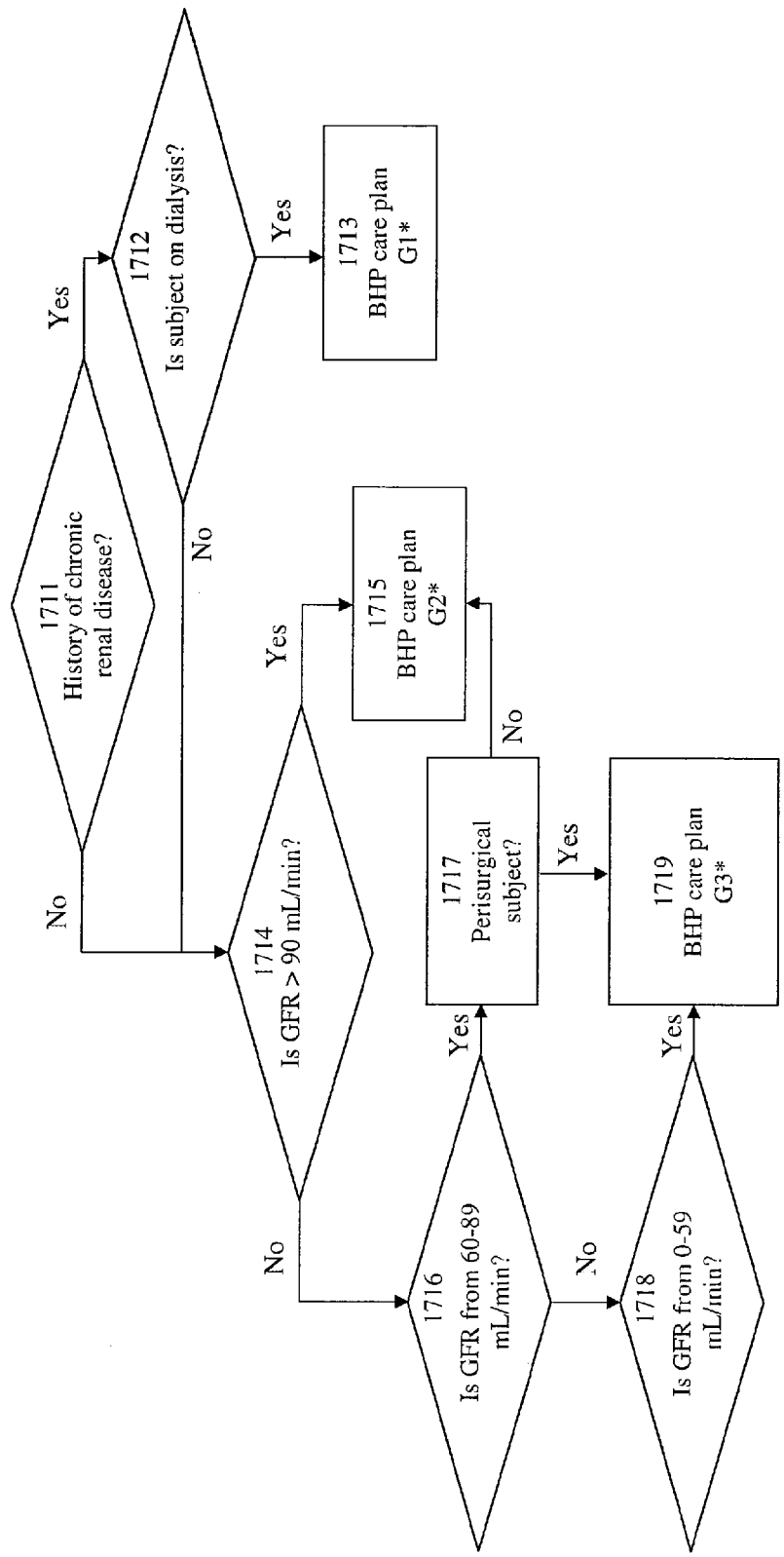

The level of renal risk, as determined by any useful method described herein, can also be used to determine a BHP care plan for a subject with chronic disease. For example, FIG. 7B is a flow diagram showing a non-limiting embodiment of determining a BHP care plan based on level of renal risk and other profile information 1710. Information about history of chronic disease is used to determine whether the subject has been diagnosed with a chronic disease 1711. If the subject has been diagnosed with chronic renal disease, then profile information is used to determine whether the subject is on dialysis 1712. If yes, then the subject is provided with patient care plan G1* that addresses the chronic disease state. Exemplary patient care plan G1* includes a combination of an erythropoietic medication (e.g., erythropoietin, epoetin, epoetin alfa, darbepoetin alfa, epoetin delta, PDpoetin, or methoxy polyethylene glycol-epoetin beta) and intravenous iron (e.g., ferric carboxymaltose, iron sucrose (Venofer®), or iron dextran (InFeD®)).

Information about glomerular filtration rate (GFR) is also used to determine the BHP care plan. If the subject has a GFR more than 90 mL/min 1714, then the subject is provided with patient care plan G2* 1715, which can include no further treatment based on no current symptoms of kidney function or include administration of oral iron and/or a multivitamin. If the subject has a GFR from 60 mL/min to 89 mL/min 1716 and if the subject will not undergo non-emergent surgery 1717, then the subject is provided with patient care plan G2*. In contrast, if the subject has a GFR from 60 mL/min to 89 mL/min 1716 and if the subject will undergo non-emergent surgery 1717, then the subject is provided with patient care plan G3*. Exemplary patient care plan G3* includes a plan to treat stage 2 chronic renal disease in a subject preparing to undergo non-emergent surgery, which is indicated by a GFR from 60 mL/min to 89 mL/min, such as a combination of an erythropoietic medication (e.g., erythropoietin, epoetin, epoetin alfa, darbepoetin alfa, epoetin delta, PDpoetin, or methoxy polyethylene glycol-epoetin beta) and intravenous iron (e.g., ferric carboxymaltose, iron sucrose (Venofer®), or iron dextran (InFeD®)). Generally, patient care plan G3* is not indicated or not covered by health insurance plans for subjects having stage 2 CKD but not undergoing surgery. Further stages of chronic renal disease can be assessed by using the GFR. If the subject has a GFR from 0 mL/min to 59 mL/min 1718, then the subject has stage 3, 4, or 5 chronic renal disease and can be provided with patient care plan G3*. Based on these advanced stages of chronic renal disease, patient care plan G3* is indicated or covered by health insurance plans for these subjects either undergoing or not undergoing surgery.

Figure 7C:
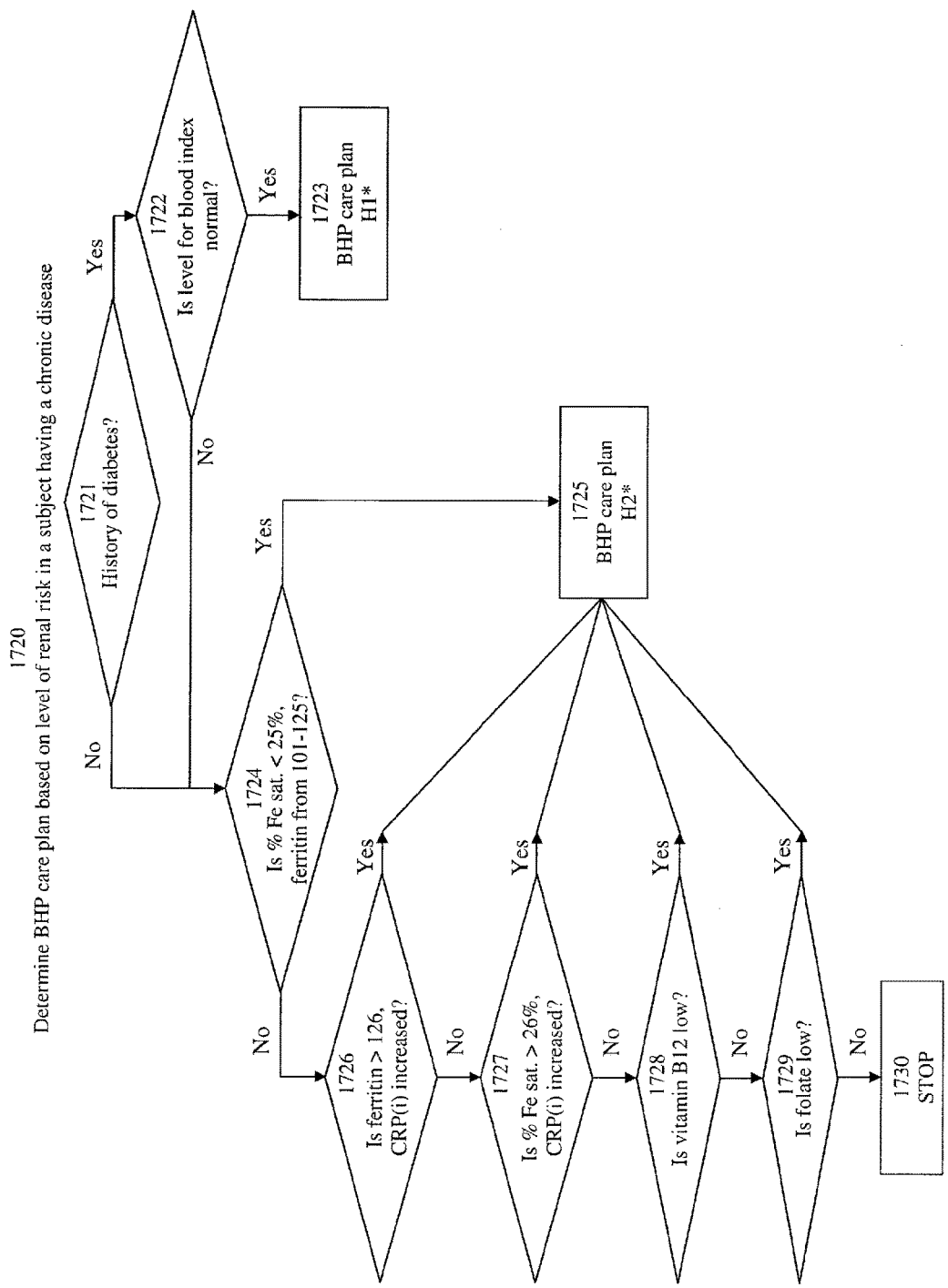

FIG. 7C shows another non-limiting embodiment of determining a BHP care plan based on level of renal risk and other profile information 1720. Information about history of diabetes is used to determine whether the subject has been diagnosed with diabetes 1721. If yes, then information regarding levels of a blood health index (e.g., levels of as determined by one or more of the following laboratory tests, including serum iron, % iron saturation, MCV, MCHC, a ferritin assay, a C reactive protein assay, a vitamin B12 test, or a folate test) is used to determine whether the subject may have symptoms related to anemia, iron-deficiency, or iron-depletion. If % iron saturation is less than 25% and/or ferritin is from 101-125 ng/mL 1724, then BHP care plan H2* is provided to the subject 1725. If ferritin is more than 126 ng/mL and C reactive protein is increased (e.g., >8 mg/L) 1726 or if vitamin B12 is low 1728 or if folate is low 1729, then BHP care plan H2* can also be provided to the subject 1725. If none of these conditions apply, then no treatment care plan is provided to the subject.

Exemplary patient care plan H2* includes one or more of an erythropoietic medication (e.g., erythropoietin, epoetin, epoetin alfa, darbepoetin alfa, epoetin delta, PDpoetin, and methoxy polyethylene glycol-epoetin beta), intravenous iron (e.g., ferric carboxymaltose, iron sucrose (Venofer®), iron dextran (InFeD®)), vitamin B12, or folate.

Figure 7D:
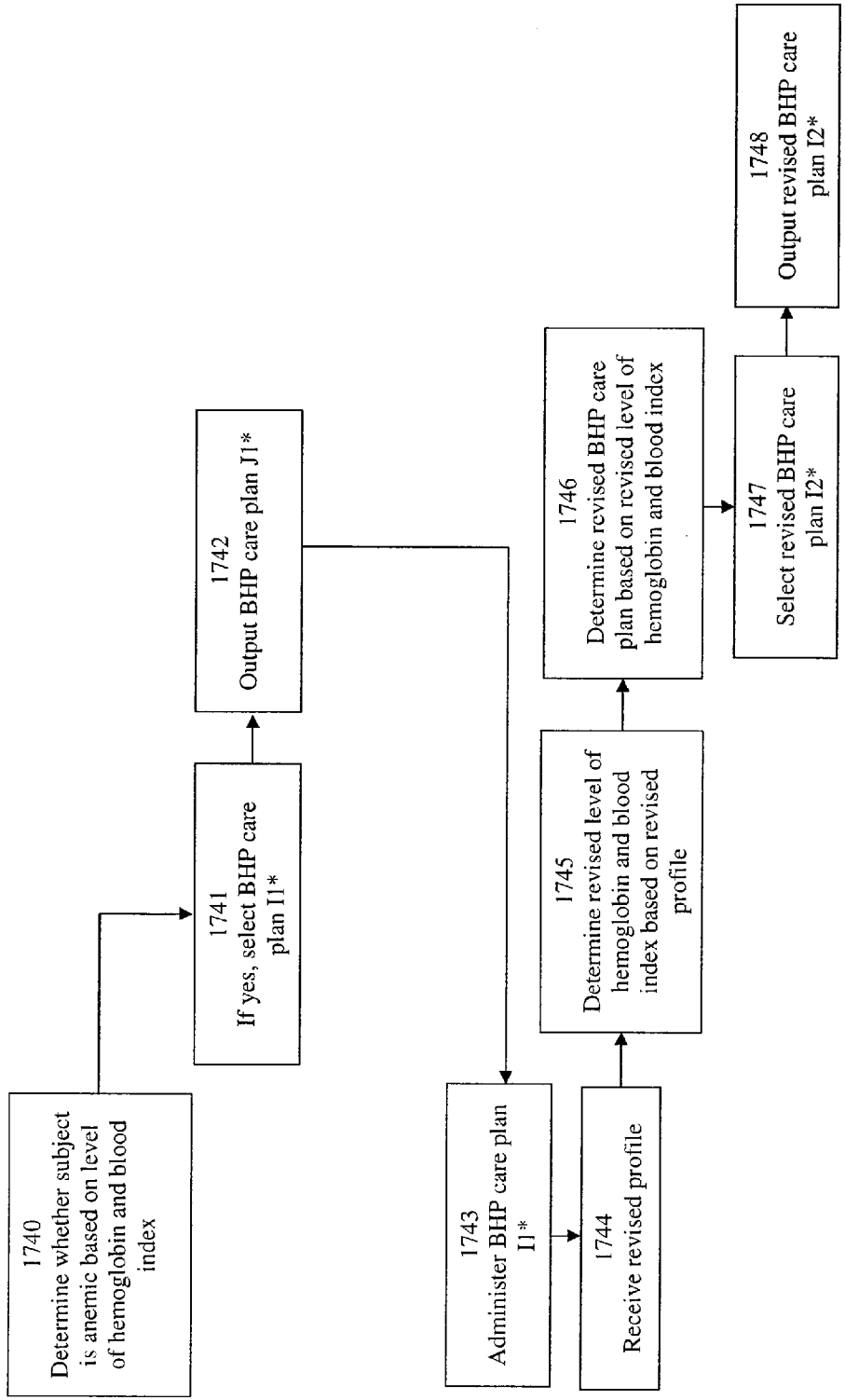

FIG. 7D shows a non-limiting embodiment of further determining a patient care plan for a subject having a chronic disease. First, the BHP protocol has been performed to determine whether the subject is anemic 1740. If the subject is anemic (e.g., using any of the methods described herein), then the protocol includes selecting 1741, outputting 1742, and administering 1743 BHP care plan I1*. Then, a revised profile is received 1744 including information about the subject after having been administered the patient care plan. The revised level of hemoglobin and blood health index is determined 1745, and these revised levels are applied to determine 1746, select 1747, and output 1748 a revised BHP care plan I2*.

Figure 7E:
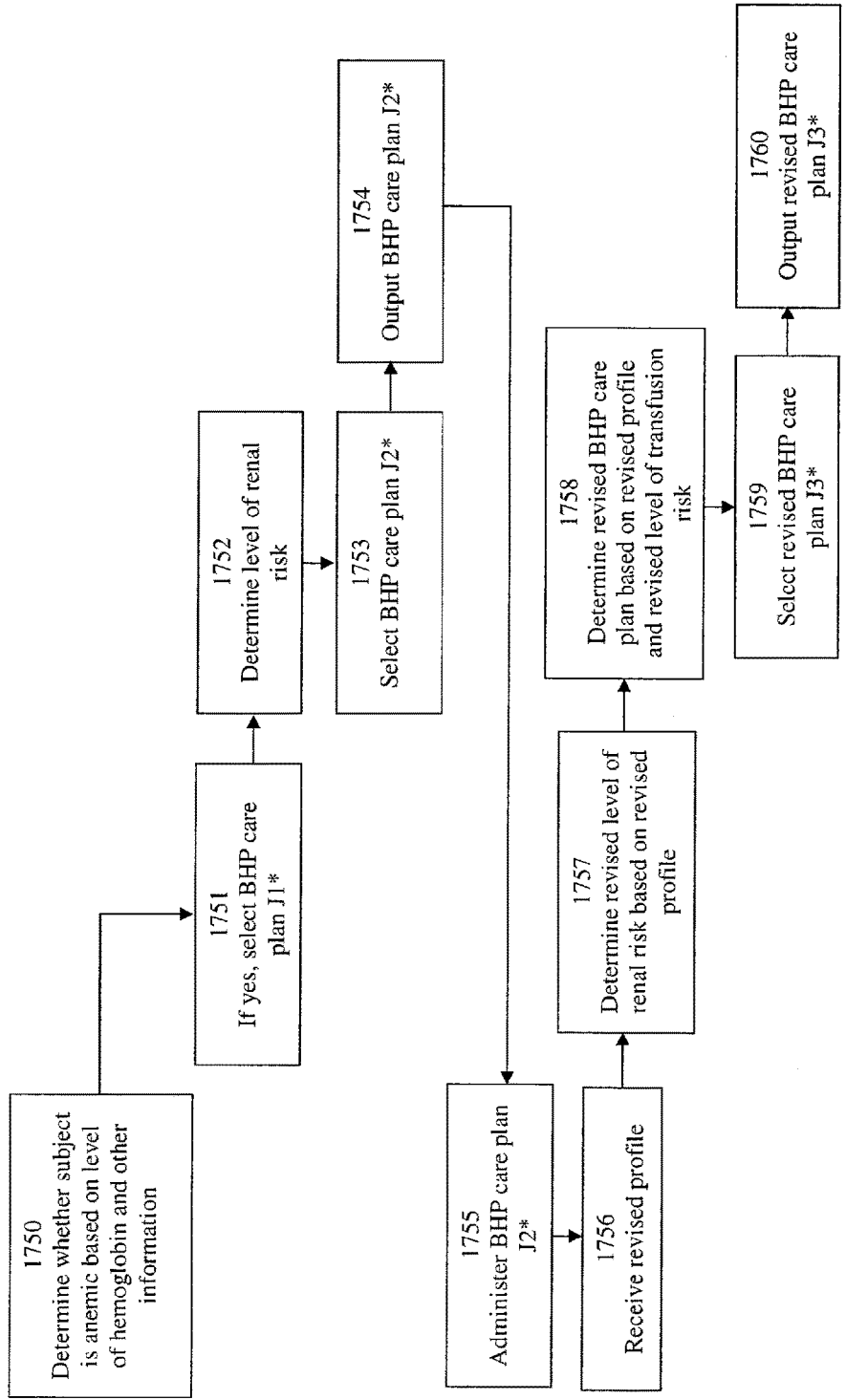

FIG. 7E shows another non-limiting embodiment of further determining a patient care plan for a subject having a chronic disease. First, the BHP protocol has been performed to determine whether the subject is anemic 1750. If the subject is anemic (e.g., using any of the methods described herein), then BHP care plan J1* is selected 1751. Then, information regarding the subject is used to determine the level of renal risk 1752, using any of the methods described herein. Based on the level of renal risk, the protocol includes selecting 1753 and outputting 1754 BHP care plan J2*, which may be the same as care plan J1* or may include one or more medications or treatments. Care plans J1* and J2* may be any patient care plan described herein.

After patient care plan J2* is administered to the subject having a chronic disease (e.g., chronic renal disease) 1755, a revised profile is received 1756. The revised profile includes information about the subject after having been administered the patient care plan. A revised level of renal risk is determined based on the revised profile 1757, where the revised level of renal risk can be determined by any method described herein. Then, the level of renal risk is applied to determine 1758, select 1759, and output 1760 a revised BHP care plan J3*.

Implementation of the Blood Health Preparedness Protocol and the Transfusion Minimization Protocol FIGS. 8A-8I provide an exemplary method for reducing transfusion risk. In particular, FIGS. 8A-8I provide details about the correlations between the level of transfusion risk, BHP care plans, and in-hospital transfusion minimization care plans. The method includes selecting patients with particularly high risk (FIG. 8A), determining transfusion risk by using a scoring system (FIG. 8B), determining which patients are considered for use of a cell saver (FIG. 8C), determining which patients are active smokers (FIG. 8D), determining which patients are take anticoagulant medication (FIG. 8E), determining bleeding risk in a patient (FIG. 8F), determining red cell antibodies in a patient (FIG. 8G), determining BHP care plan(s) (FIG. 8H), and determining in-hospital transfusion minimization care plan(s) (FIG. 8I).

FIG. 8A shows a method for identifying patients with such a high risk that the blood health management program should be halted and that the surgery should be reconsidered. Examples of such patients includes those with a level of hemoglobin (Hgb) less than or equal to 10.0 g/dL, those with new renal disease, those with a level of creatinine more than or equal to 2.0 mg/dL and known history of renal disease, or those not undergoing a non-emergent high blood loss (NEH-BLS) procedure.

After selecting appropriate patients for the blood health management program (as in FIG. 8A), a scoring system can be used to determine the transfusion risk of the patient based on information from the profile. FIGS. 8B-1 to 8B-3 show a scoring system based on the various information from the profile, such as level of hemoglobin (Hgb), gender, age, date of the surgery, level of creatinine (Cr), whether the surgery is a redo surgery, weight (wt), or whether the surgery is non-isolated (e.g., a multi-site procedure). Questions can be formulated based on the information from the profile (diamonds, in FIGS. 8B-1 to 8B-3). Alternatively, one or more other questions can be included in the scoring system. For example, the first diamond in FIG. 8B-1 can be replace "Hgb ≤12.9" with "Hgb ≤13.4." In another example, the second diamond in FIG. 8B-2 can be replace "Cr ≥2" with "GFR <59 or less", where GFR is glomerular filtration rate. A response of yes or no to the questions can correlate to a particular value (as shown in table in figure); to a particular patient care plan, such as consideration for cell saver or for a preoperative BHP plan (pre-op tx plan, such as shown in FIGS. 8H-1 to 8H-3); or to a particular in-hospital transfusion minimization care plan (in-hosp plan, such a shown in FIGS. 8I-1 to 8I-2).

FIG. 8C shows a method for determining whether use of a cell saver is appropriate. For example, the presence of an active malignancy or an active infection would contraindicate use of a cell saver. The type of surgery can also determine whether a cell saver (CS) should be used. For example, particular types of surgeries would usually already include use of a cell saver, such as cardiac surgery; other particular surgery types would be recommended for use of a cell saver, such as hip replacement surgery, spine surgery, or abdominal aortic aneurysm (AAA, where CS may also be included for AAA surgery); other types of surgery would be contraindicated for use of a cell saver, such as gastrointestinal surgery or gynecologic oncology surgery; and other types of surgery would require further determination, such as neurosurgery, prostatectomy, or postoperative use of CS for knee replacement surgery.

FIGS. 8D and 8E show additional determinations based on whether the patient is an active smoker (FIG. 8D) or takes anticoagulant medication (FIG. 8E). Smoking could have an adverse effect on surgical outcome. FIG. 8D shows a method to determine whether a patient is an active smoker based on their profile and whether the patient requires a preoperative patient care plan. If a patient care plan is not indicated for the patient, then information regarding the cessation of smoking before surgery is communicated to the patient with a recommendation to stop smoking. If a patient care plan is indicated, then the discussion to stop smoking is discussed during preoperative communication of the patient care plan.

FIG. 8E shows a method to determine the type of anticoagulant medication taken by the patient. Use of anticoagulant medications could lead to increased bleeding during surgery, thus increasing the likelihood of requiring a transfusion. If appropriate, the patient should cease taking anticoagulant medications at least one week prior to the surgery. As shown in FIG. 8E, over the counter (OTC) or herbal anticoagulants should be discontinued before surgery, either one week prior to surgery (e.g., for aspirin) or immediately (e.g., for other self-referred, over the counter, or herbal anticoagulants, such as dong quoi, bromelain, chamomile, dandelion root, garlic, ginger, gingko biloba, St. John's wort, or vitamin C). Prior to the surgery, the patient can be sent a reminder to discontinue use of the anticoagulant.

For prescription anticoagulant medications (e.g., Coumadin or Plavix®), further discussion with the prescribing physician may be needed before recommending that the patient discontinue use of the anticoagulant medication. A reminder can be sent to the patient one week before the surgery to check with their physician in timing the discontinued use of the medication.

FIG. 8F shows a method for determining bleeding risk. Known bleeding disorders and undiagnosed bleeding disorder could indicate that further referrals are needed with a hematologist or that the surgery may be delayed for additional patient workup. To determine whether an undiagnosed bleeding disorder is present, the patient can be asked questions with regard to history of bleeding. If any of the questions are positive, then a determination is made as to whether the patient is taking procoagulant medication, such as by asking the patient or by searching the profile of the patient. If the patient is taking a procoagulant medication, then no tests are done and the general blood management and BHP protocols are followed. If patient is not taking medication, then additional laboratory tests are requested and analyzed to determine whether the patient has a previously undiagnosed bleeding disorder. If the tests return negative, then the patient is tracked in the database (DB) to flag for any warning signs. If the tests return positive, then additional consults to surgery and/or hematology may be needed.

FIG. 8G shows a method for determining whether the patient has red cell antibodies and whether special or rare types of transfusion products may be necessary in the event of a transfusion. If a red cell antibody screen is negative, then further testing is not required. If the red cell antibody screen is positive, the further tests are needed to define the type of antibodies or to determine whether the initial screen was a false positive. If red cell antibodies are present, then use of cell saver should be considered and the patient blood type should be determined. For patients with red cell antibodies, information regarding the patient's blood type and the antibodies identified should be incorporated into a BHP care plan and/or in-hospital transfusion minimization care plan and communicated to the hospital and blood bank, so compatible transfusion products are available for surgery, obviating the need for surgery cancellation or surgery proceeding without compatible blood available. The plan can include results from the test panels, as well as the patient's name, date of surgery, type of procedure, whether the surgery is a redo or a de novo procedure, the name of the surgeon, the patient's blood type, and the type of red cell antibodies.

FIGS. 8H-1 to 8H-3 show various outpatient BHP care plans based on the blood health management program, as implemented obtained above. If the patient is not anemic, then a BHP specialized care plan for anemia is not necessary. If the level of comorbidity indicates elevated or significant risk (e.g., the presence of a severe comorbid condition or the presence of numerous comorbid conditions), then a surgeon may need to be consulted for follow-up or for rescheduling the surgery. If comorbidities do not indicate elevated or significant risk, then a preoperative patient care plan is created.

FIG. 8H-1 shows care plans for an anemic patient. For example, the basic patient care plan includes intravenous iron, where the plan is communicated to the surgeon and the surgeon orders the treatment. The dosing of the intravenous iron is patient-specific. If chronic renal failure is present with anemia, then special plan #1a includes use of erythropoietin (EPO), as well as possible consideration for dialysis for a high level of creatinine and possible consult with a nephrologist, in conjunction with the basic patient care plan. If an active non-bacterial (e.g., viral) infection or inflammatory disease is present with anemia, then the same special plan #1b can be used in conjunction with the basic patient care plan. The administration of EPO is indicated not only to treat anemia but also to treat active inflammation.

FIGS. 8H-2 and 8H-3 show preoperative patient care plans for other comorbid conditions. For example, the use of preoperative dialysis, such as special plan #2 for renal failure; use of preoperative coagulation therapy, such as special plan #3 for documented bleeding disorder; notification of patient, surgeon, and hospital blood bank of the presence of red cell antibodies, and consideration of preoperative autologous blood donation if multiple antibodies are present, such as in special plan #4; notifications with regard to ceasing use of anticoagulant medications before surgery, such as special plan #5 for patients taking over the counter or prescription anticoagulants; and notification with regard to ceasing smoking, such as in special plan #6. For all patients (those with or without increased risk of transfusion), a baseline patient care plan can be provided (e.g., daily administration of a multivitamin with iron or a multivitamin with iron and vitamin C separately), and the score, risk, and patient care plans are communicated to the patient, surgeon, and primary care physician.

FIGS. 8I-1 and 8I-2 show examples of in-hospital transfusion minimization care plans based on the presence of various risk factors. When no particular in-hospital plan is indicated, then the patient can be identified as being blood conscious, such as by use of an armband, as in hospital plan A. Various other hospital plans can be formulated to address the transfusion risk of the patient. For example, the communication of use of cell saver to the surgeon and hospital, as in hospital plan B; the use of pediatric tubes and determination of range of anticipated loss of blood volume and tolerable loss of blood volume, as in hospital plan C for patients with a weight of less than or equal to 75 kg; a hand-crafted patient care plan based on particularly high risk comorbidities (e.g., renal failure, active heart disease but not associated with cardiovascular surgery, pulmonary/CNS disease, but not undergoing heart surgery), determination of range of anticipated loss of blood volume and tolerable loss of blood volume, and consideration for use of a transfusion product that is less than 10-14 days old, as in hospital plan D; a hand-crafted BHP care plan or in-hospital transfusion minimization care plan for patients with documented coagulopathy, as in hospital plan E; use of DDAVP® to decrease blood loss or consideration of platelet transfusion for a patient with renal failure, as in hospital plan F; and completion of patient BHP care plan for anemia in-hospital or on outpatient basis as needed, as in hospital plan G.

Table 1 shows an exemplary implementation of the blood health management program in the form of a checklist. Each response to the question (Qn) can be answers to decision problems ("yes" or "no"), which can then be assigned an integer number (Xn), such as 0, 1, or 2, or answers requesting more information (e.g., what kind of anticoagulants is the subject taking?). Also shown is the effect of each response on the patient care plan and the in-hospital transfusion minimization care plan or on another step in the protocol. The patient questionnaire refers to a questionnaire provided to the subject regarding his or her health status, where this questionnaire can be provided by the subject's physician or by the transfusion management healthcare provider.

TABLE 1

Exemplary checklist implementing the blood health management program

| Question (Q) | Response | Effect on blood healthcare preparedness (BHP) or in-hospital transfusion minimization (TM) care plans | Effect on Blood Health Management Program |
|---|---|---|---|
| Q1. Is anemia present? | Yes or No | If yes, then treatment of anemia needs be considered as part of BHP. | If yes, then comorbidities may need to be evaluated (see Q20-Q22). |

TABLE 1-continued

Exemplary checklist implementing the blood health management program

| Question (Q) | Response | Effect on blood healthcare preparedness (BHP) or in-hospital transfusion minimization (TM) care plans | Effect on Blood Health Management Program |
|---|---|---|---|
| Q2. Is the gender male? | If yes, then X2 = 0. If no, then X2 = 1. | X2 will be used to determine level of transfusion risk (see Q19). | |
| Q3. Is the age more than 65 years? | If yes, then X3 = 1. If no, then X3 = 0. | X3 will be used to determine level of transfusion risk (see Q19). | |
| Q4. Is the non-elective surgery two or more weeks from scheduling to start date? | If yes, then X4 = 0. If no, then X4 = 1. | X4 will be used to determine level of transfusion risk (see Q19). | |
| Q5. Is anemia present? | If yes, then go to Q6-Q8. If no, then go to Q9. | The presence of anemia indicates that anemia should be considered in BHP. | |
| Q6. Is hemoglobin above 11.4 g/dL and below 13.0 g/dL (or between 11.5-12.9 g/dL)? | If yes, then X6 = 1. If no, then X6 = 0 and go to Q7. | X6 will be used to determine level of transfusion risk (see Q19). | |
| Q7. Is hemoglobin between 10-11.4 g/dL? | If yes, then X7 = 2. If no, then X7 = 0 and go to Q8. | X7 will be used to determine level of transfusion risk (see Q19). | |
| Q8. Is hemoglobin <10.0 g/dl? | If yes, then STOP. If no, then go to Q9. | Presence of severe anemia indicates that the subject's physician should be contacted to possibly delay the surgery until this underlying condition is treated, unless severe anemia is in keeping with the clinical history, i.e., severe anemia is common in colon cancer patients; anemia treatment should start immediately and surgery should not be delayed. | |
| Q9. Is creatinine <1.2 mg/dL? | If yes, then X9 = 0 and go to Q13. If no, then go to Q10. | X9 will be used to determine level of transfusion risk (see Q19). | |
| Q10. Is creatinine between 1.2-1.9 mg/dL? | If yes, then X10 = 1. If no, then go to Q11. | X10 will be used to determine level of transfusion risk (see Q19). | |
| Q11. Is creatinine ≥2.0 mg/dL? | If yes, then X11 = 2 and go to Q12. If no, then go to Q13. | X11 will be used to determine level of transfusion risk (see Q19). | |
| Q12. Is the renal failure new or chronic? | If new, then STOP. If chronic, then go to Q13. | Evidence of a new diagnosis for renal failure indicates that the subject's physician should be contacted to possible delay the surgery until this underlying condition is treated. | |
| Q13. Does patient have anemia and chronic renal failure? | Yes or No | If yes, then BHP includes treatment with erythropoietin. | |
| Q14. Does patient have anemia and renal disease? | Yes or No | If yes, then BHP includes treatment with erythropoietin. | |
| Q15. Is this a redo surgery? | If yes, then X15 = 1. If no, then X15 = 0. | If yes, then BHP possibly includes use of cell saver. X15 will be used to determine level of transfusion risk (see Q19). | If cell saver is to be used, then malignancy and infection may need to be evaluated. Presence of a malignant tumor or infection precludes use of cell saver or any other autologous blood donation. |

TABLE 1-continued

Exemplary checklist implementing the blood health management program

| Question (Q) | Response | Effect on blood healthcare preparedness (BHP) or in-hospital transfusion minimization (TM) care plans | Effect on Blood Health Management Program |
|---|---|---|---|
| Q16. Is weight between 50-75 kg (110-165 lbs)? | If yes, then X16 = 1 and go to Q18. If no, then go to Q17. | If yes, then BHP possible includes use of cell saver and/or use of any other strict blood minimization strategies (e.g., use of pediatric blood tubes for blood draws). X16 will be used to determine level of transfusion risk (see Q19). | If cell saver is to be used, then malignancy and infection may need to be evaluated. Presence of a malignant tumor or infection precludes use of cell saver or any other autologous blood donation. |
| Q17. Is weight <50 kg (110 lbs)? | If yes, then X17 = 2. If no, then go to Q18. | If yes, then BHP possible includes use of cell saver and/or use of any other strict blood minimization strategies (e.g., use of pediatric blood tubes for blood draws). X17 will be used to determine level of transfusion risk (see Q19). | If cell saver is to be used, then malignancy and infection may need to be evaluated. Presence of a malignant tumor or infection precludes use of cell saver or any other autologous blood donation |
| Q18. Is this a multisite (or non-isolated) procedure? | If yes, then X18 = 1. If no, then X18 = 0. | If yes, then BHP possibly includes use of cell saver. X18 will be used to determine level of transfusion risk (see Q19). | If cell saver is to be used, then malignancy and infection may need to be evaluated. Presence of a malignant tumor or infection precludes use of cell saver or any other autologous blood donation. |
| Q19. What is the sum for any integer provided for X1 to X18? Note: total is 11 points. | If sum is ≤3, then an in-hospital transfusion minimization care plan is not needed. If sum >3, then an in-hospital transfusion minimization care plan is needed. | The sum is related to the level of transfusion risk. Therefore, a level of risk of >3 indicates likelihood that the subject may need a transfusion and that an in-hospital transfusion minimization care plan should be determined. | If sum >3, then comorbidities may need to be evaluated and additional review of this subject's profile may be needed. |
| Q20. Is anemia present, creatinine >1.2 mg/dL, and/or weight <75 kg? | If yes, then subject needs a patient questionnaire correlation (PQC), a comorbidity check (CC), and consideration for cell saver as part of the care plan (CS). If no, then subject needs a PQC and may need a CC. | If the listed conditions are present, then further analysis is necessary to identify increased risk. Consideration for cell saver (CS) as part of the BHP during surgery may be indicated. Minimization of blood loss by use of cell saver should be considered in subjects with high level of transfusion risk or subjects with anemia. | The PQC would see whether the patient questionnaire included any other additional information or comorbidities that will affect the BHP, such as by using the questions in Q21-Q31. The CC would assess the comorbidities more in-depthly and determines whether the surgery would be more risky without a preoperative BHP, whether comorbidities should be considered in creating an in-hospital transfusion minimization care plan, or whether both a preoperative BHP and in-hospital transfusion minimization care plan are needed. |

TABLE 1-continued

Exemplary checklist implementing the blood health management program

| Question (Q) | Response | Effect on blood healthcare preparedness (BHP) or in-hospital transfusion minimization (TM) care plans | Effect on Blood Health Management Program |
|---|---|---|---|
| Q21. Is the surgery a redo procedure and a multisite surgery? | If yes, then go modify BHP. If no, then go to Q22. | If yes, then BHP possibly includes use of cell saver and/or use of any other strict blood minimization strategies (e.g., use of pediatric blood tubes for blood draws). If no, then further CC may not be needed. | |
| Q22. Is the subject taking anticoagulants? | If yes, then go to Q23. If no, then go to Q24. | If yes, then the subject should be reminded to discontinue the anticoagulants one week prior to the surgery if possible. | |
| Q23a. What kind of anticoagulants? Q23b. Is it over the counter (OTC) or prescriptive (P)? | Answer to Q23a should be a list. For Q23b, if OTC, then need to send personal reminder to discontinue. For Q23b, if P, then need to send personal reminder to discontinue after obtaining approval of subject's physician's approval. | For prescriptive medication, approval of the subject's physician is needed. | |
| Q24. Is there any history of bleeding? | If yes, then go to Q25. If no, then go to Q26. | | |
| Q25. Was the bleeding previously diagnosed? | If yes, then no further testing needed and need referral to subject's hematologist (via surgeon) for BHP and in-hospital transfusion minimization care plan. If no, then need further testing. Schedule subject for blood draw and coagulation studies. | Diagnosed bleeding disorders require that the subject's hematologist be consulted in determining the BHP and in-hospital transfusion minimization care plan (e.g., use of platelets, fresh frozen plasma, and/or factor concentrates). Non-diagnosed bleeding disorders should be evaluated. Further tests can include those that would identify the coagulation abnormality. After obtaining test results, a hematologist and/or primary care physician should be consulted. | |
| Q26. Is the subject an active smoker? | If yes, then provide subject with information regarding smoking and recovery after surgery. If no, then go to Q27. | If yes, then information can be provided to the subject or subject's physician. This information can provide reasons as why needs to stop prior to surgery and during recovery for best outcome. | |
| Q27. Is there a history of active infection? | If yes, then provide type of malignancy. If no, then go to Q28. | If yes, then BHP cannot include use of a cell saver. | |
| Q28. Is there presently an active infection? | If yes, then provide type of infection and go to Q29. If no, then go to Q30. | If yes, then BHP cannot include use of a cell saver. | |
| Q29. Is the subject anemic and has an active infection? | If yes, then need to modify BHP or in-hospital transfusion minimization care plan. If no, then go to Q30. | If yes, then anemia and the inflammatory component may signify the need for erythropoietin. | |

TABLE 1-continued

Exemplary checklist implementing the blood health management program

| Question (Q) | Response | Effect on blood healthcare preparedness (BHP) or in-hospital transfusion minimization (TM) care plans | Effect on Blood Health Management Program |
|---|---|---|---|
| Q30. Is the red cell antibody screen positive? | If yes, then provide type of antibody. If no, then go to Q31. | If yes, then BHP or in-hospital transfusion minimization care plan may include preoperative autologous blood donation and use of cell saver during the surgery, if applicable (e.g., no malignancy and no active infection). | |
| Q31. Is the subject anemic and was anemia treated? | If yes, provide with what type of medication, number of treatments, and results of treatment (e.g., hemoglobin levels). | | |
| Q32. Is this the first time that the subject has been assessed? | If yes, then go to Q34. If no, then go to Q33. | | This part of the checklist tracks when the subject's profile was first assessed with the blood health management program. |
| Q33. Was the surgery rescheduled or cancelled? | If yes, then provide surgery date to be used to determine level of transfusion risk in Q34. If no, then go to Q34. | | |
| Q34. Has updated laboratory test results been received? | If yes, then reiterate Q1-Q19 with new data to determine an updated level of transfusion risk. If no, then reiterate Q1-Q19 with available data to determine an updated level of transfusion risk. | | |
| Q35. Is there a difference between the previous and updated level of transfusion risk? | If yes, then describe and show in what area the points changed. If no, then STOP. | | |

Figures 1, 9:
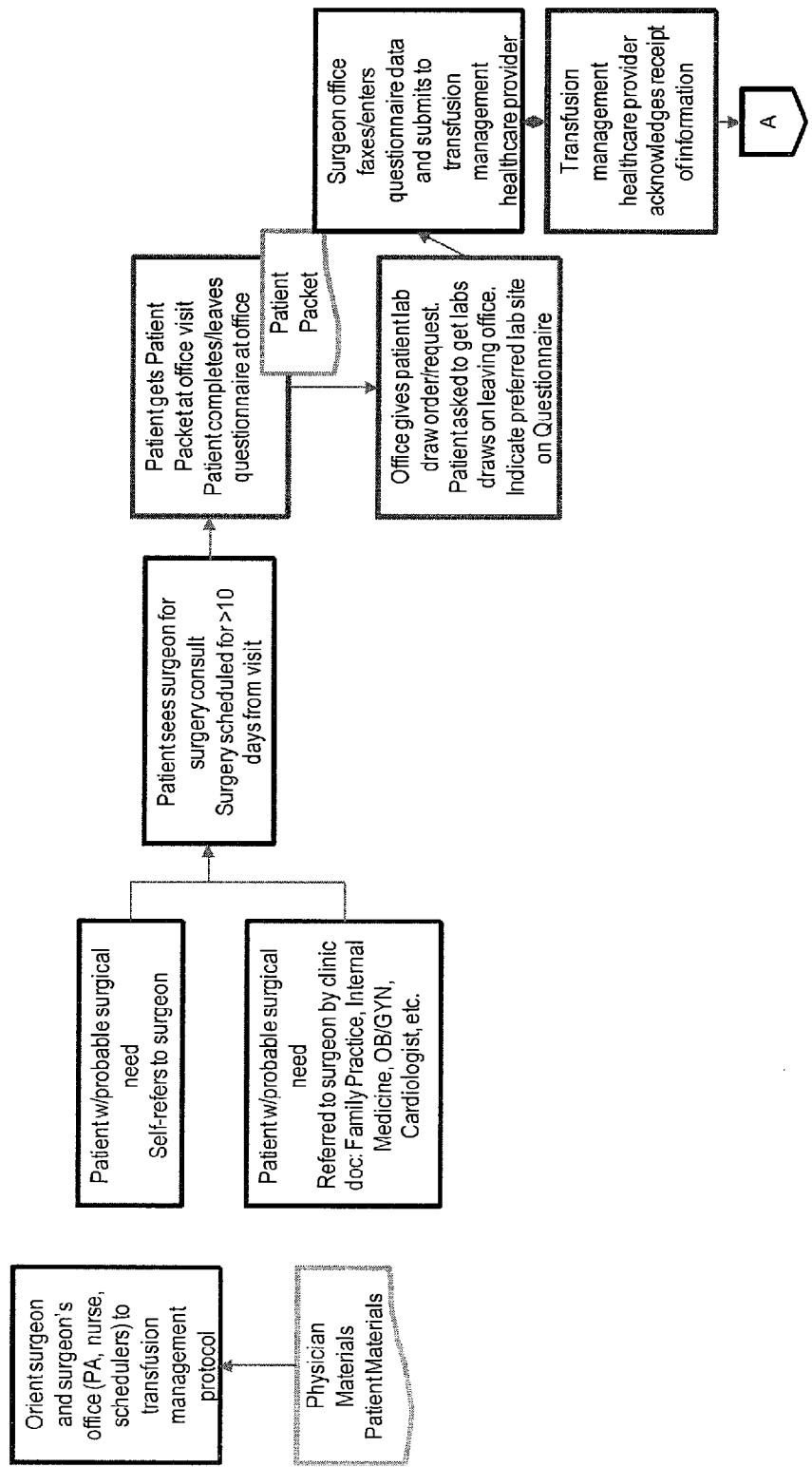
Figures 2, 9:
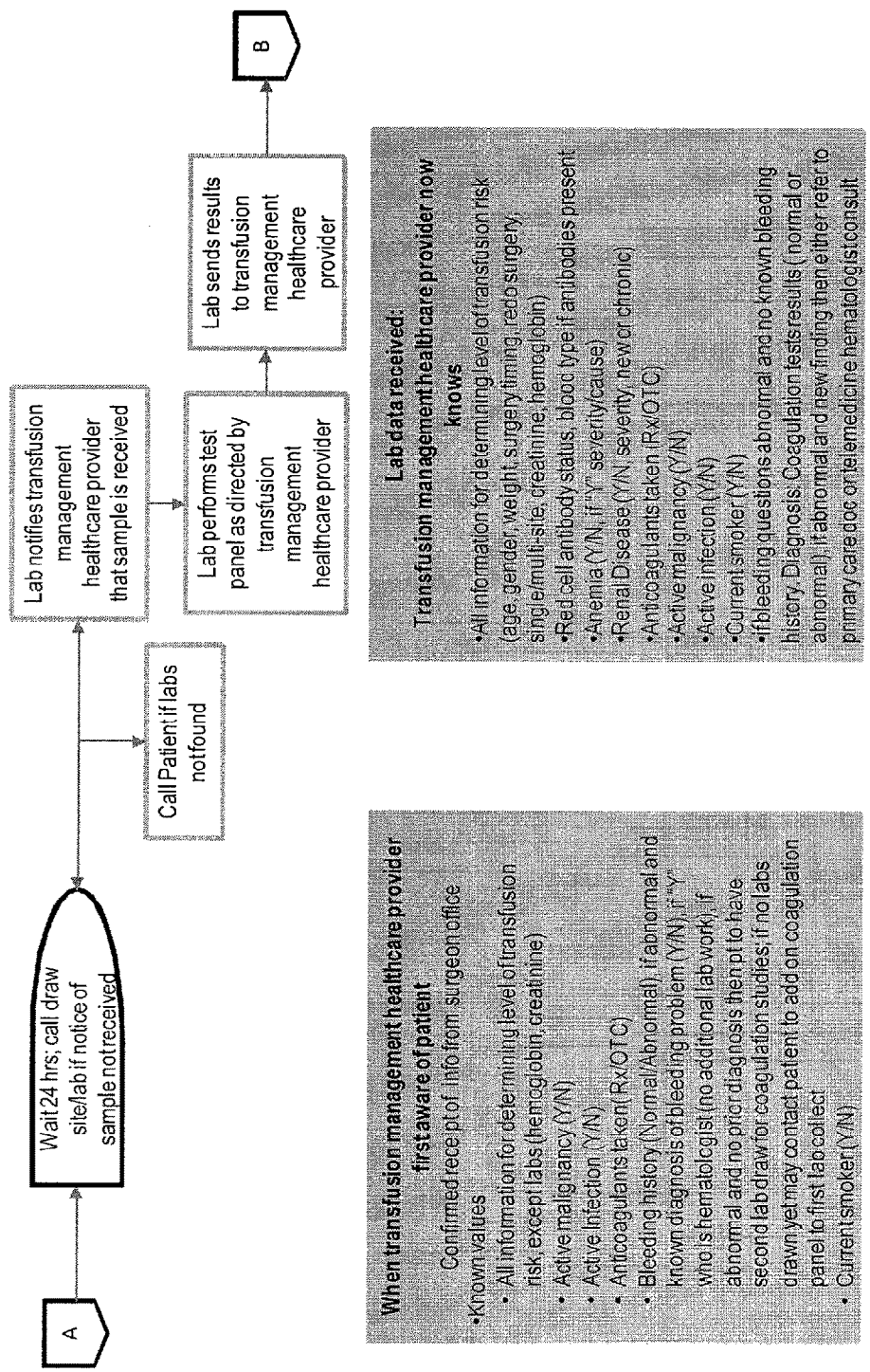
Figures 3, 9:
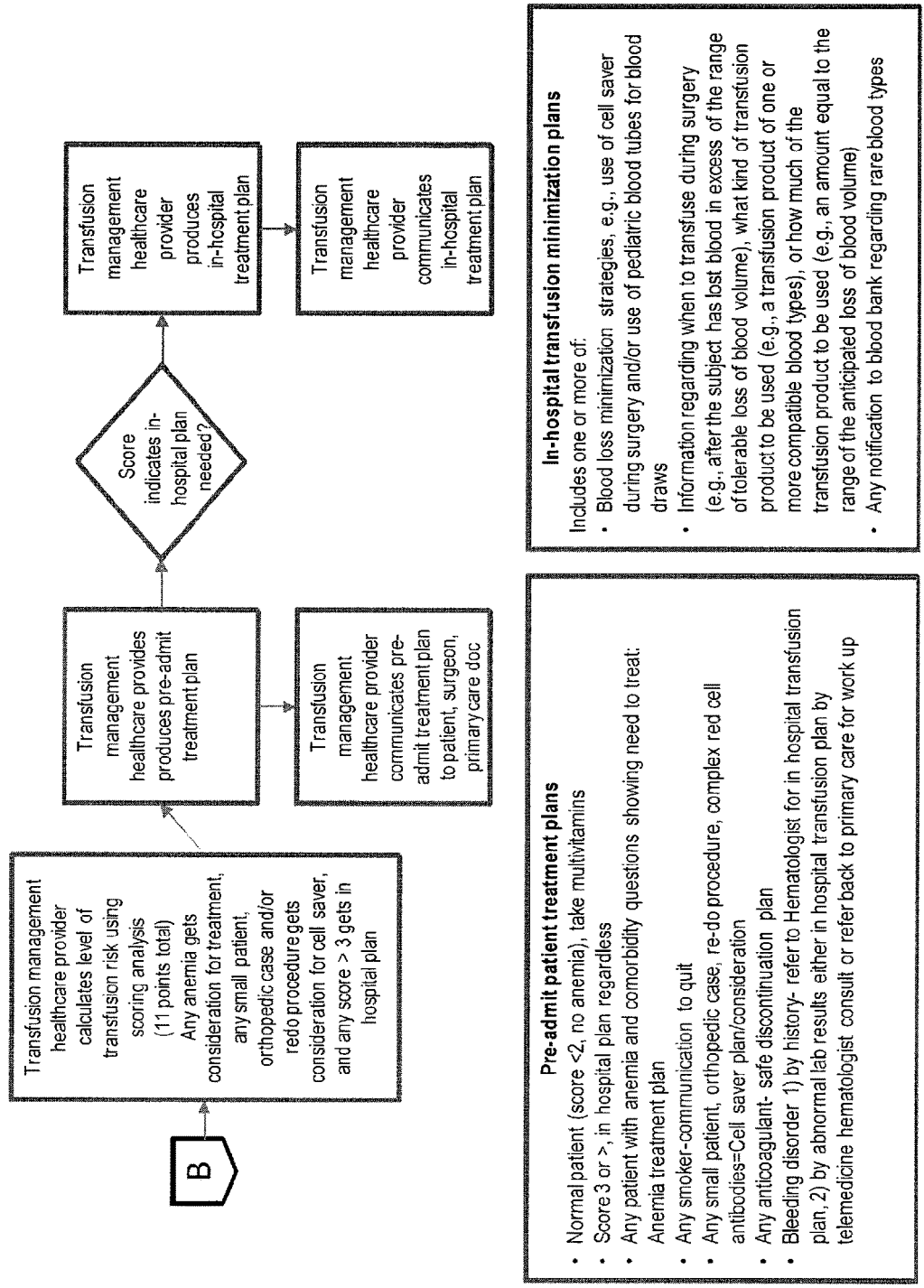
Figures 4, 9:
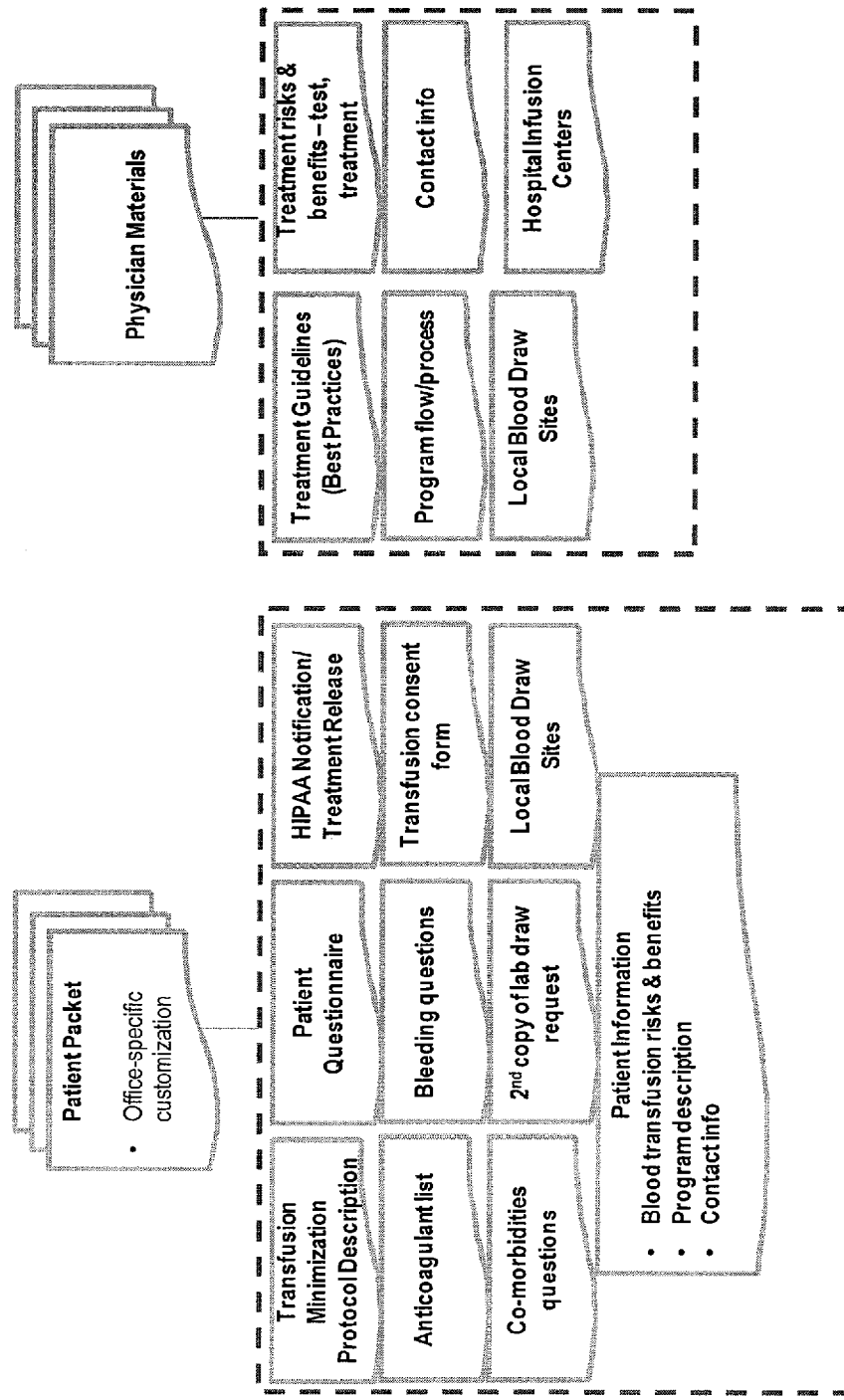

FIG. 9 is a flow diagram generally showing one embodiment of implementing the blood health management program. The transfusion management healthcare provider first contacts the surgeon and orients the surgeon and surgeon's office to the blood management program, including preoperative blood health preparedness and in-hospital transfusion minimization protocols. The blood health management program can optionally include various materials, which can be used to inform the subject or hospital employee, such as a physician. Examples of such materials are provided in FIG. 9-4 for the patient, as shown by the patient packet, and for the surgeon, as shown by physician materials.

Referring to FIG. 9-1, the patient with probable surgical needs contacts and sees the surgeon. The patient typically receives a patient packet including information about the BHP protocol and a patient questionnaire, which can be used to obtain information for the patient's profile. The surgeon's office provides the patient with an order to get laboratory tests at the patient's preferred laboratory site and submits information from the questionnaire to the transfusion management healthcare provider.

Referring to FIG. 9-2, the transfusion management healthcare provider will have some known values about the patient upon first becoming aware of the subject. The transfusion management healthcare provider will likely not have the most recent laboratory values for hemoglobin and creatinine, where recent values for these tests are preferred. Within 24 hours of being aware of the patient, the transfusion management healthcare provider will notify the laboratory site to determine whether the patient's sample was drawn. If the sample is not found, then the transfusion management healthcare provider contacts the patient. If sample is found and laboratory results are ready, then the laboratory site can input the results in the program's physical computing device and the results will be incorporated into the patient's profile and exported to the transfusion management healthcare provider, along with the medical history and other intakes questionnaire data points that are formatted on a computer dashboard. The transfusion management healthcare provider will then inform the laboratory site of which test panels should be conducted on the patient's sample. Some laboratories will have the testing profile for how to evaluate the samples, including, reflex tests to additional panels based on initial results (e.g., a positive red cell antibody screen would result in performing an antibody identification test, where a positive antibody identification test would result in ABO and Rh typing). Laboratory results will be forwarded to the transfusion management healthcare provider, so that the transfusion management healthcare provider will have all the information required to determine level of transfusion risk.

Referring to FIG. 9-3, the transfusion management healthcare provider will determine the level of transfusion risk, preferably by using a scoring system, such as described in Table 1 or FIG. 8. The presence of certain information in the profile may indicate a particular patient care plan. For example, a patient with anemia will be considered for a BHP plan that will treat anemia. Patients that are small (as determined by weight) or that will undergo an orthopedic surgery and/or a redo procedure will be considered for use of a cell saver during their procedure. Any patient with an increased level of transfusion risk, such as a score >3 for the scoring system provided in Table 1, will receive an in-hospital transfusion minimization care plan. Based on the level of transfusion risk, the transfusion management healthcare provider will produce a pre-admit BHP care plan and communicate this plan to the patient, surgeon, and primary care doctor. If needed, the transfusion management healthcare provider will also produce an in-hospital transfusion minimization care plan and communicate this plan to the patient, surgeon, and primary care physician.

Program Evaluation Protocol

To determine the effect of implementing a blood health management program (e.g., the BHP protocol and TM protocol), information about the subject after the non-emergent surgery can be obtained to determine a patient outcome report. Information regarding the subject after the non-emergent surgery may include, for example, information regarding loss of blood volume during the surgery, whether the subject had a transfusion during the surgery, or information regarding adverse events. Specific examples of adverse events include whether the subject was undertransfused during the surgery; whether there was excessive loss of blood volume by the subject during or after the surgery; whether there were any acute transfusion reactions, such as an acute hemolytic reaction, a febrile nonhemolytic transfusion reaction, transfusion-associated circulatory overload, transfusion-related acute lung injury, or post-transfusion purpura; whether there was an infection during or after the surgery; whether there were complications during the surgery; whether the subject required prolonged hospitalization, which can be determined by length of stay; whether there were any significant, persistent, or permanent change, impairment, or damage in the subject's bodily function, bodily structure, physical activities, or quality of life; death; or other events that are not related to the surgery, such as falls.

Information regarding the subject after the non-emergent surgery, as well as information from the profile, can then be used to determine a patient outcome report. For example, the patient outcome report can compare one or more of a patient care plan, an in-hospital transfusion minimization care plan, or a test panel with information about the subject after the non-emergent surgery. The patient outcome report can include any number of assessments or comparisons between the profile of the subject before the non-emergent surgery, one or more results of the blood management health protocol, or the profile of the subject after the non-emergent surgery. Specific examples of assessments include a comparison between the profile before the non-emergent surgery and the profile after the non-emergent surgery; a comparison between the level of transfusion risk and information regarding adverse events; a comparison between the level of transfusion risk and information regarding whether the subject had a transfusion during the non-emergent surgery; a comparison between level of comorbidity and information regarding adverse events; a comparison between the patient care plan and the profile of the subject after the non-emergent surgery; a comparison between the patient care plan and information regarding adverse events; or a comparison between the in-hospital transfusion minimization care plan and information regarding blood loss during the non-emergent surgery.

Patient Outcome Reports

Figure 10A:
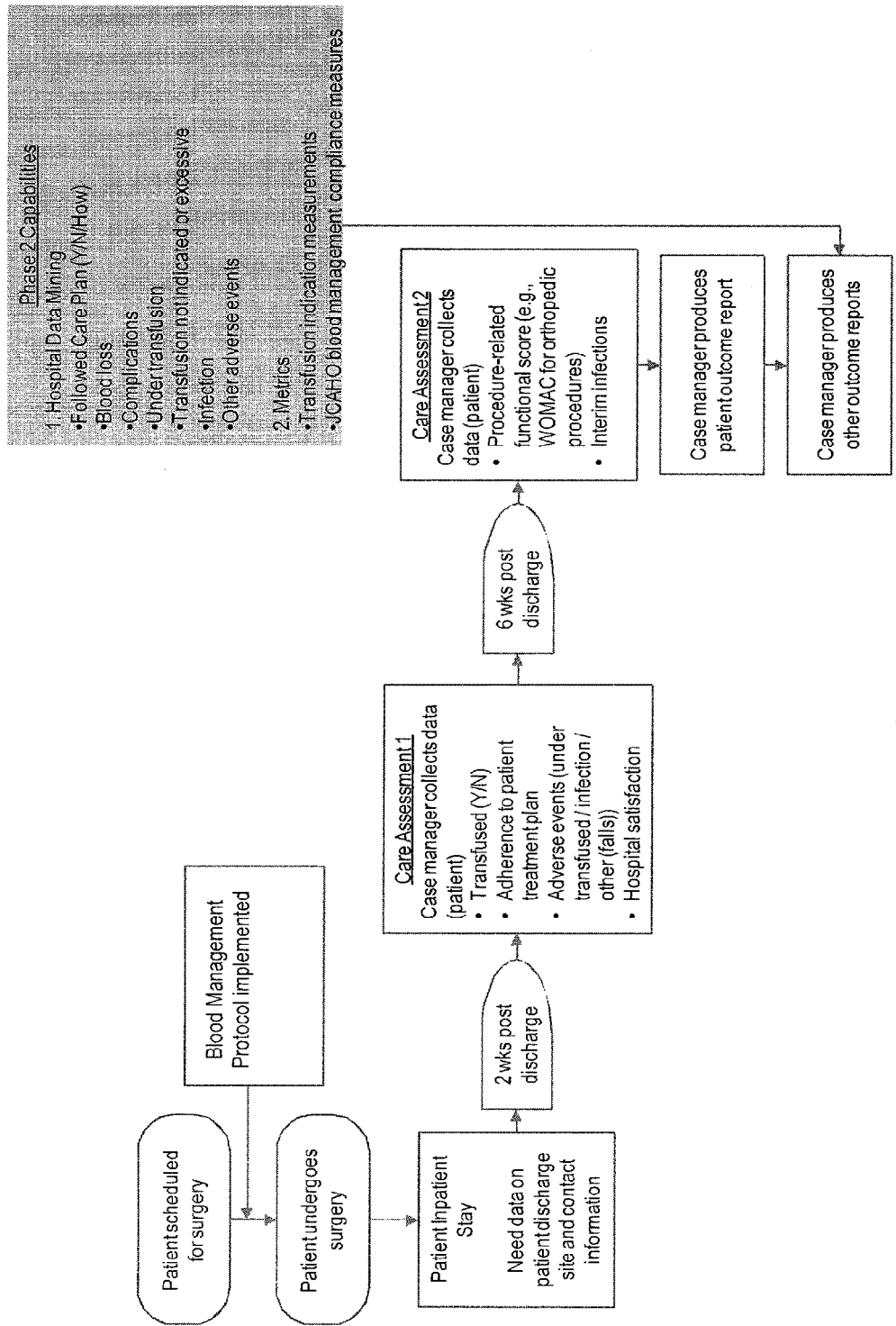
FIGS. 10A and 10B are flowcharts of a non-limiting embodiment for producing a patient outcome report and for refining the BHP protocol.

FIG. 10A is a flowchart showing an exemplary process for producing a patient outcome report. After the patient undergoes surgery, the patient stays within the hospital for inpatient recovery. Prior to discharge from the hospital, the transfusion management healthcare provider obtains patient discharge information and contact information. About two weeks post discharge, the transfusion management healthcare provider collects data about the patient, such as information regarding whether the patient was transfused, whether the patient or physician adhered to the patient care plan, adverse events, and hospital satisfaction. About six weeks post discharge, the transfusion management healthcare provider collects additional information about the patient, such as interim infections or WOMAC (Western Ontario and McMaster Universities) index for orthopedic procedures. Based on patient information, the transfusion management healthcare provider produces a patient outcome report. The process can also include other capabilities, such as hospital data mining and determining other indication metrics. These capabilities can be integrated with information from the patient outcome report to produce other types of outcome reports, such as reports that are not specific to the patient but relate generally to the hospital or DRG.

Relating to chronic diseases, the outcome report can include additional indexes used for quality of life and physical function assessment. Exemplary indexes include the general quality of life questionnaires (e.g., a Patient Global Assessment test or European Quality of Life-5 Dimensions test), Minnesota Living with Heart Failure Questionnaire (MLWHFQ), the Kansas City Cardiomyopathy Questionnaire (KCCQ), the minute walk test, or the New York Heart Association functional Class.

Figure 10B:
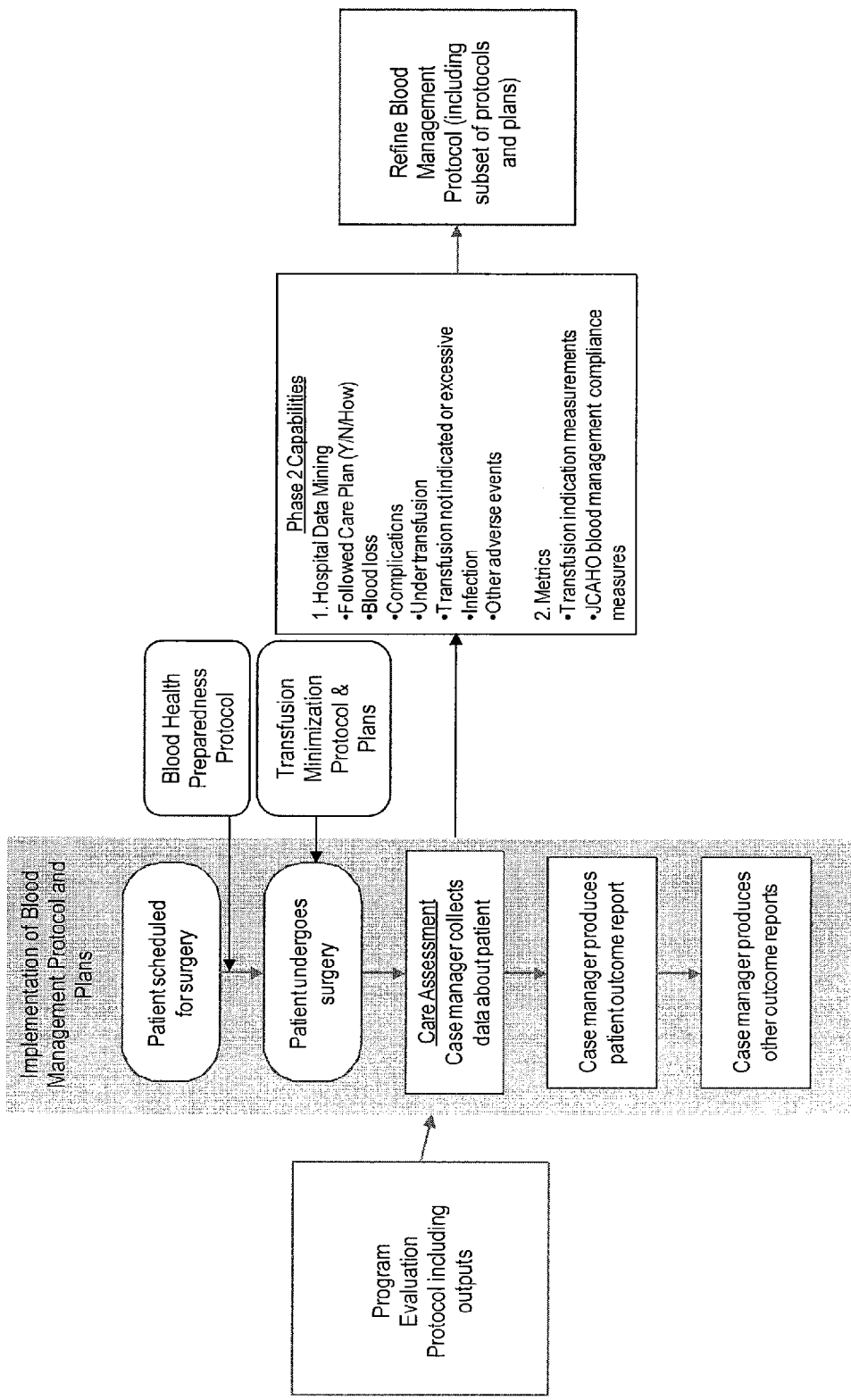

The results from the outcome reports or hospital data mining can be used to further refine the blood health management program. FIG. 10B is a flowchart of a non-limiting embodiment for refining the blood health management program. After implementing the complete blood health management program and producing one or more outcome reports (e.g., patient outcome report or other types of outcome reports), hospital data mining can be used to compare subjects that underwent the surgery with or without using the blood health management program and various metrics can be determined to assess the blood health management program. Based on the results of the data mining and the metrics, the blood health management program can be refined.

The patient outcome report can be used in any number of ways. For example, the patient outcome report can be outputted to one or more of a computer readable media, a server, a network, a display device, or a printed report. In another example, the patient outcome report can be used to treat a subject, such as by administrating an outpatient or inpatient care plan based on the results of the patient outcome report.

The patient outcome report can include statistical context, such as a comparison of the subject's information with other patient populations. Examples of other types of information include those related to the preoperative process, the in-hospital experience, and those related to any risk factors associated with the patient care plan or in-hospital transfusion minimization care plan. The patient outcome report can be specific to the subject, hospital, surgeon, surgical group, or DRG. The patient outcome report can also include data gathered over time, which can be used to further update or validate the blood health management program. The patient outcome report can include details about the surgery at the patient level, as well as validated comparisons with other clinical metrics. For example, the patient outcome report can include measurements of transfusion indication and appropriateness; Joint Commission on the Accreditation of Healthcare Organizations (JCAHO) blood management compliance measures; or a procedure-related functional score, such as the WOMAC index for orthopedic procedures.

Other Outcome Reports

Other types of outcome reports can be determined, where these reports are not specific to the subject but relate generally to the hospital or DRG. Examples of other types of outcome reports include patient satisfaction outcome reports, hospital satisfaction outcome reports, adverse event outcome reports, which can be related to transfusions and hospitalization in general, and surgical outcome-specific reports (e.g., the WOMAC index). The recipients of these outcome reports may include any interested party, such as a subject, consumer groups, health plans, the subject's primary care doctor, the subject's surgeon, surgical specialty organizations, and hospitals. Optionally, the information from these other types of outcome reports is incorporated into a patient outcome report.

The output reports can also focus on data obtained from the pre-hospital space (e.g., preoperative BHP protocol), such as before the surgery; hospital space (e.g., in-hospital TM protocol), such as during or right after the surgery; and post-hospital space (e.g., program evaluation protocol), such as after the subject had left the hospital. Those who can benefit from or use the pre-hospital output reports include: an individual patient, a patient's surgeon, a patient's primary care doctor, a hospital where the patient is being seen or where patients have high blood loss surgery (e.g., for aggregate data of patients by DRG or other demographic), a health plan (e.g., for proof that an individual patient went through protocol and was better prepared for surgery), consumer interest groups (e.g., for protocol results and for information regarding whether patients for high risk procedures were better prepared), device companies for products involved in high blood loss surgeries (e.g., heart valves, cell savers, cardiovascular perfusion equipment, and joint or spine prosthesis), health care safety and quality groups, Centers for Medicare & Medicaid Services (e.g., for aggregate data by DRG in their aged patient population), the Department for Veteran Affairs hospitals and hospital systems (e.g., for aggregate data by DRG in their relevant patient population), public health groups, employers, state and accreditation agencies, and surgical and hospital societies (e.g., the American Orthopedic Association, the American College of Thoracic Surgeons, the American Hospital Association, etc.).

The patient outcome report can also provide financial data, such as for hospitals, health plans, Centers for Medicare & Medicaid Services, the Department for Veteran Affairs hospitals and hospital systems, and consumer health groups. Those who can benefit from or use the hospital and post-hospital output reports include: hospital(s), health plan(s), Centers for Medicare & Medicaid Services, the Department for Veteran Affairs (e.g., VA hospitals and hospital systems), consumer watch groups (e.g., AARP), regulatory agencies, surgical and hospital societies (e.g., the American Orthopedic Association, the American College of Thoracic Surgeons, the American Hospital Association, etc.), and employers. Examples of the type of information included in these output reports are provided below in Table 2.

TABLE 2

| Pre-hospital space | Hospital space | Post-hospital space |
|---|---|---|
| individual, correlated, and aggregated data patient care plan(s) | individual, correlated, and aggregated data transfusion data (whether patient transfused, how much and with what) with comparison of patients based on level of hemoglobin; comparison of patient populations, such as those patients with patient care plans as opposed to those without, patients who went through the blood health management program (as compared to other non-participants or other matched controls) | individual, correlated, and aggregated data readmission rates, where program patients can be compared to other non-participants or other matched controls |
| treatment outcome data, such as in the preoperative space only (e.g., hemoglobin was increased when anemia was treated; patients stopped their anticoagulants before surgery reliably, patients stopped smoking before surgery to improve ability to heal postoperatively, patients had bleeding disorders diagnosed prior to surgery, patients with | length of stay data, where program patients can be compared to other non-participants or other matched controls | hospital and surgeon and program satisfaction data |

TABLE 2-continued

| Pre-hospital space | Hospital space | Post-hospital space |
|---|---|---|
| renal disease and other patients, such as those who may benefit from cell saver, and had a different plan of care with which to enter the surgery) financial data, such as providing outpatient processing and anemia treatment cost and % of patients that needed treatment | hospital cost for stay, where program patients can be compared to other non-participants or other matched controls regulatory information (American Association of Blood Banks, College of American Pathologists, Joint Commission), such as information on the appropriateness of transfusion in program patients (e.g., as measured with an algorithmic approach) and JCAHO measurements on preoperative assessment of orthopedic patients, which includes hemoglobin assessment 30-60 days preoperative and red cell antibody screen prior to the day of anesthesia addressed and reported on as a single metric for the hospital transfusion reactions and transfusion related adverse effects/events, where program patients can be compared to other non-participants or other matched controls non-transfusion adverse events, such as infections, myocardial infarct, new renal failure, unexpected need for ventilator, fall with injury, etc. in-hospital transfusion minimization care plans | procedure related improvement score assessment data (if applicable and validated tool exists, e.g., WOMAC score for hip replacement patients) complications and associated healthcare costs thereof as identified after patient has left hospital (i.e., as many post operative infections are identified after the patient has left the hospital as while they were an inpatient), where program patients can be compared to other non-participants or other matched controls |

Devices for Performing a Blood Health Management Program

The methods described herein can be implemented in a computer readable storage medium comprising executable code. Specific examples of computer readable storage media include tape, such as a magnetic tape; a disk or a diskette, such as a portable computer diskette, a magnetic disk, a magneto-optical disk, a removable disk, an optical disk, or an internal hard disk; memory, such as random access memory, read-only memory, an erasable programmable read-only memory (e.g., Flash memory), or a portable compact disc read-only memory. Specific examples of executable code include software or firmware.

The executable code can access data or information from a profile in any number of ways. For example, the data can be transmitted, entered, or stored in any component that can be accessed by the executable code. The data can be transmitted in any useful way, such as by use of a computer readable medium, a server, or a network. The data can be entered manually or downloaded electronically. The data can be stored in any form, such as in physical form, as written or printed on paper; in magnetic form, as stored on a tape, a card, or a disk; in electronic form, as stored in a database or on a memory; or in optical form, as stored on an optical disk.

A result from executing the executable code can be outputted in any number of a computer readable medium, a server, a network, a display device, or a printed report. A computer readable medium, as described herein, includes all computer readable storage media. Specific examples of servers include a web server, a network server, or a private server. Specific examples of networks include those of different architecture, such as peer-to-peer file sharing or client-server networking; or those of different scale, such as a personal area network; local area network; campus area network; metropolitan area network; wide area network; global area network; virtual private network; or internetworks, such as interne, intranet, or extranet. Examples of display devices include a digital display device, such as a liquid crystal display device; an electronic display device, such as an electronic ink display device; or a visual display device, such as a computer interface or a projector screen. Examples of printed reports include an electronically printed report, such onto a file or a disc; an optically printed report, such as onto an optical disc; or a physically printed report, such as onto paper.

Figure 11:
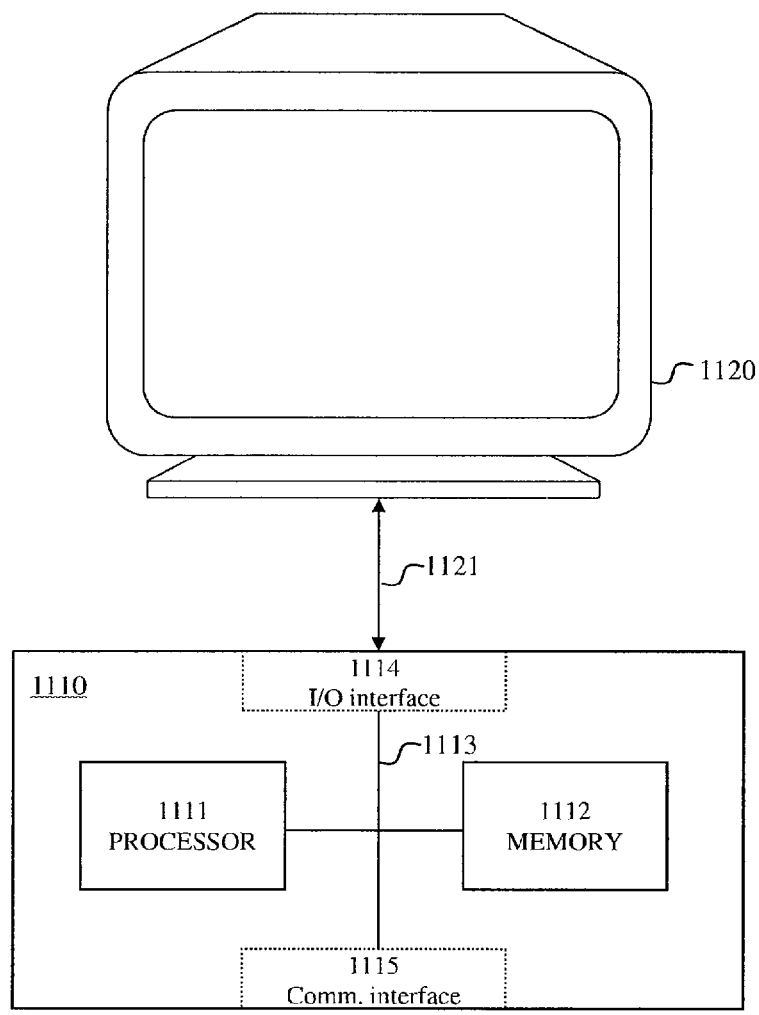
FIG. 11 is a schematic of an exemplary physical computing device for performing a method of reducing transfusions during or after a non-emergent surgery.

Also provided herein is a physical computing device to perform a blood health management program. FIG. 11 shows a schematic of an exemplary physical computing device 1110. The physical computing device 1110 comprises a processor 1111, a memory 1112, and an interconnection mechanism 1113 coupling the processor 1111 and the memory 1112. In order to perform the blood health management program, the memory 1112 is encoded with an executable code that causes the processor 1111 to perform the protocol. The interconnection mechanism 1113 allows the processor 1111 to launch, access, run, execute, interpret, or perform the executable code encoded in the memory 1112. The interconnection mechanism 1113 can have any useful form, such as a data bus or other circuitry. The physical computing device 1110 can optionally include an input/output interface 1114 that allows communication 1121 between the physical computing device 1110 and an external component, such as a display device 1120 or a computer readable medium (not shown). The physical computing device 1110 can also optionally include a communications interface 1115 that allow communication between the physical computing device and another external physical computing device, such as another machine, a server, or a network (not shown).

Figure 12:
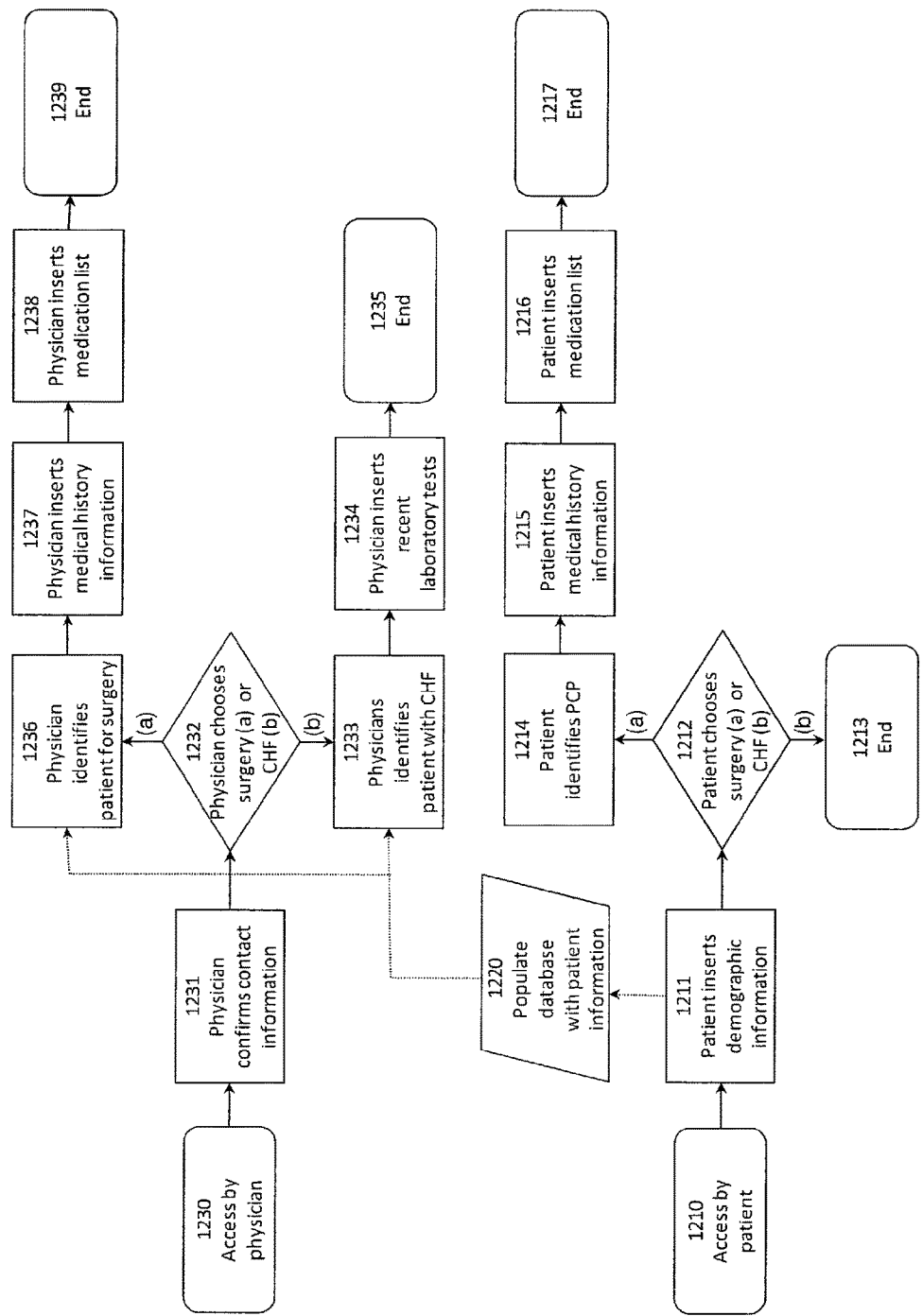
FIG. 12 is an exemplary flowchart for display screens on a physical computing device to implement the methods described herein.

FIG. 12 shows an exemplary flowchart for display screens on a physical computing device to implement a blood health management program for reducing transfusions and for treating congestive heart failure. Instead of providing information to a transfusion management healthcare provider (e.g., such as 13 in FIG. 1A), a physical computing device (e.g., a machine) can be used to obtain information from the subject (e.g., a patient) and the subject's healthcare provider (e.g., a physician) for the BHP protocol. As shown in FIG. 12, an exemplary physical computing device can be accessed by a patient 1210 or by a physician 1230. When accessed by a patient, the first display screen 1211 provides an interface for the patient to insert demographics information, including whether the patient will be undergoing non-emergent surgery or whether the patient has congestive heart failure (CHF). This screen 1211 can also include additional requirements related to privacy concerns and HIPAA for release of the provided demographics information. This screen 1211 can include radio buttons for various surgeries, including total knee replacement (single or bilateral), total hip replacement (single or bilateral), cardiac valve replacement, coronary artery bypass surgery (with or without valve repair or valve replacement), or other, and additional radio buttons to indicate whether the surgery is a primary procedure or a redo procedure.

Based on whether the patient will undergo surgery or require treatment for CHF 1212, different displays screens will be provided. If the patient chooses CHF (shown as (b) for 1212), then the next display screen 1213 shows that this protocol has ended.

If the patient chooses surgery (shown as (a) for 1212), then the next display screen 1214 requires the patient to identify their primary care provider (PCP). The following display screen 1215 prompts the patient to insert medical history information for their profile. Exemplary medical history information includes information regarding current and past history of bleeding (e.g., diagnosis of bleeding that is unrelated to medication use; history of prolonged bleeding, including one or more of having nose bleeds or bleeding for prolonged times after minor injuries, having prolonged menstrual bleeding (more than seven days), having prolonged bleeding after surgery, or having prolonged bleeding after a tooth extraction; history of bruises and black spots; familial history of bleeding abnormalities and diagnosis of bleeding disorders); information regarding medication taken by the subject (e.g., one or more anticoagulant medications, such as heparin and warfarin (i.e., Coumadin); one or more procoagulant medications, such as a zeolite, desmopressin, a coagulation factor, such as factor VII, tranexamic acid, aminocaproic acid, or aprotinin; insulin; or one or more antiplatelet medications, such as cyclooxygenase inhibitors, including aspirin); current and past history of disease, such as renal disease, liver disease, diabetes, heart disease (e.g., a heart attack); current and past history of treatment for a disease, such as treatment with dialysis or insulin; current and past history of smoking; and current and past history of drinking (e.g., more than 5 drinks per week).

The next display screen 1216 includes a prompt for a list of medications taken by the patient. For example, this display screen includes radio buttons for prescription medications, for common over the counter (OTC) medications, for herbal medications, or for activities (e.g., drinking more than five alcoholic drinks per week) that could lead to increased bleeding during surgery. Exemplary prescription medications include one or more anticoagulant medications, one or more thrombolytics, or one or more antiplatelet medications. Exemplary OTC and herbal medications include dong quoi, bromelain, chamomile, dandelion root, garlic, ginger, gingko biloba, St. John's wort, or vitamin C. This information could be used to suggest that the patient refrain from taking these OTC or herbal medications or from these activities prior to the surgery. The final display screen 1217 shows that this protocol has ended. Upon entry of this information by the patient, the database is populated with the information 1220 to provide the profile of the patient.

As also shown in FIG. 12, the physical computing device can be accessed by a physician 1230 for a patient's profile. When accessed by a physician, the first display screen 1231 prompts the physician to confirm contact information. The next display screen 1232 provides an interface for the physician to decide whether the patient will be undergoing non-emergent surgery or whether the patient has congestive heart failure (CHF).

Based on the whether the physician chooses surgery or treatment for CHF, different displays screens will be provided. If the physician chooses CHF (shown as (b) for 1232), then the next display screen 1233 prompts the physician to identify the patient having CHF. The following display screen 1234 prompts the physician to enter results from recent laboratory tests (e.g., one or more of hemoglobin, creatinine, and glomerular filtration rate (GFR)). The final display screen 1235 shows that this protocol has ended.

If the physician chooses surgery (shown as (a) for 1232), then the next display screen 1236 prompts the physician to identify the patient preparing to undergo non-emergent surgery. The following display screen 1237 prompts the physician to enter medical history information. Exemplary medical history information includes information regarding current and past history of bleeding (e.g., diagnosis of bleeding that is unrelated to medication use; history of prolonged bleeding, including one or more of having nose bleeds or bleeding for prolonged times after minor injuries, having prolonged menstrual bleeding (more than seven days), having prolonged bleeding after surgery, or having prolonged bleeding after a tooth extraction; history of bruises and black spots; familial history of bleeding abnormalities and diagnosis of bleeding disorders); information regarding medication taken by the subject (e.g., one or more anticoagulant medications, such as heparin and warfarin (i.e., Coumadin); insulin; one or more thrombolytics; or one or more antiplatelet medications, such as cyclooxygenase inhibitors, including aspirin); current and past history of disease, such as kidney disease, liver disease, diabetes, heart disease (e.g., a heart attack); current and past history of treatment for a disease, such as treatment with dialysis or insulin; current and past history of smoking; and current and past history of drinking (e.g., more than 5 drinks per week).

The next display screen 1238 includes a prompt for a list of prescription medications taken by the patient. For example, this display screen includes radio buttons for various prescription medications that could lead to increased bleeding during surgery, including one or more anticoagulant medications, one or more thrombolytics, or one or more antiplatelet medications. The final display screen 1239 shows that this protocol has ended.

EXAMPLE

Three patients with different profiles are submitted to the transfusion management healthcare provider. The patients are all scheduled for a primary hip surgery, where patient 1 is an elderly female patient with anemia, patient 2 is an elderly female patient with anemia and an active infection, and patient 3 is a healthy male patient. More details about the patient's profile are provided in Table 3, which also provides an evaluation using the blood health management program.

TABLE 3

| Question (Q) | Response | Patient 1 | Patient 2 | Patient 3 |
|---|---|---|---|---|
| Type of Procedure | | Primary hip | Primary hip | Primary hip |
| Q1. Is anemia present? | Yes (Y) or No (N) | Y | Y | N |
| Q2. Is the gender male? | If yes, then X2 = 0. If no, then X2 = 1. | 1 | 1 | 0 |
| Q3. Is the age more than 65 years? | If yes, then X3 = 1. If no, then X3 = 0. | 1 | 1 | 0 |
| Q4. Is the non-elective surgery two or more weeks from scheduling to start date? | If yes, then X4 = 0. If no, then X4 = 1. | 0 | 0 | 0 |
| Q5. Is anemia present? | If yes, then go to Q6-Q8. If no, then go to Q9. | Y | Y | N |
| Q6. Is hemoglobin above 11.4 g/dL or below 13.0 g/dL (or between 11.5-12.9 g/dL)? | If yes, then X6 = 1. If no, then X6 = 0 and go to Q7. | 0 | 0 | — |
| Q7. Is hemoglobin between 10-11.4 g/dL? | If yes, then X7 = 2. If no, then X7 = 0 and go to Q8. | 2 | 2 | — |
| Q8. Is hemoglobin <10.0 g/dl? | If yes, then STOP. If no, then go to Q9. | N | N | — |
| Q9. Is creatinine <1.2 mg/dL? | If yes, then X9 = 0 and go to Q13. If no, then go to Q10. | 0 | 0 | 0 |
| Q10. Is creatinine between 1.2-1.9 mg/dL? | If yes, then X10 = 1. If no, then go to Q11. | — | — | — |
| Q11. Is creatinine ≥2.0 mg/dL? | If yes, then X11 = 2 and go to Q12. If no, then go to Q13. | — | — | — |
| Q12. Is the renal failure new or chronic? | If new, then STOP. If chronic, then go to Q13. | — | — | — |
| Q13. Does patient have anemia and chronic renal failure? | Yes (Y) or No (N) | N | N | N |
| Q14. Does patient have anemia and renal disease? | Yes (Y) or No (N) | N | N | N |
| Q15. Is this a redo surgery? | If yes, then X15 = 1. If no, then X15 = 0. | 0 | 0 | 0 |
| Q16. Is weight between 50-75 kg (110-165 lbs)? | If yes, then X16 = 1 and go to Q18. If no, then go to Q17. | 1 | 1 | N |
| Q17. Is weight <50 kg (110 lbs)? | If yes, then X17 = 2. If no, then go to Q18. | — | — | N |
| Q18. Is this a multisite (or non-isolated) procedure? | If yes, then X18 = 1. If no, then X18 = 0. | 0 | 0 | 0 |
| Q19. What is the sum for any integer provided for X1 to X18? | If sum is ≤3, then an in-hospital transfusion minimization care plan is not needed. If sum >3, then an in-hospital transfusion minimization care plan is needed. | 5 | 5 | 0 |

TABLE 3-continued

| Question (Q) | Response | Patient 1 | Patient 2 | Patient 3 |
|---|---|---|---|---|
| Q20. Is anemia present, creatinine >1.2 mg/dL, and/or weight <75 kg? | If yes, then subject needs a patient questionnaire correlation (PQC), a comorbidity check (CC), and consideration for cell saver as part of the care plan (CS). If no, then subject needs a PQC and may need a CC. | PQC, CC, and CS: anemic patient and needs BHP and in-hospital transfusion minimization care plan | PQC, CC, and CS: anemic patient and needs BHP and in-hospital transfusion minimization care plan | PQC: generally health patient, where PQC sufficient to determine comorbidities and in-depth check of CC not required |
| Q21. Is the surgery a redo procedure and a multisite surgery? | If yes, then go modify BHP. If no, then go to Q22. | N | N | N |
| Q22. Is the subject taking anticoagulants? | If yes, then go to Q23. If no, then go to Q24. | N | Y | N |
| Q23a. What kind of anticoagulants? Q23b. Is it over the counter (OTC) or prescriptive (P)? | Answer to Q23a should be a list. For Q23b, if OTC, then need to send personal reminder to discontinue. For Q23b, if P, then need to send personal reminder to discontinue after obtaining approval of subject's physician's approval. | — | Q23b. P: need to send personal reminder to discontinue after obtaining approval of subject's physician's approval | — |
| Q24. Is there any history of bleeding? | If yes, then go to Q25. If no, then go to Q26. | N | N | N |
| Q25. Was the bleeding previously diagnosed? | If yes, then no further testing needed and need referral to subject's hematologist (via surgeon) for BHP and in-hospital transfusion minimization care plan. If no, then need further testing. Schedule subject for blood draw and coagulation studies. | — | — | — |
| Q26. Is the subject an active smoker? | If yes, then provide subject with information regarding smoking and recovery after surgery. If no, then go to Q27. | Y: need to send information regarding smoking | N | N |
| Q27. Is there a history of active infection? | If yes, then provide type of malignancy. If no, then go to Q28. | N | N | N |
| Q28. Is there presently an active infection? | If yes, then provide type of infection and go to Q29. If no, then go to Q30. | N | Y (MRSA) | N |
| Q29. Is the subject anemic and has an active infection? | If yes, then need to modify BHP or in-hospital transfusion minimization care plan. If no, then go to Q30. | — | BHP may include EPO (erythropoietin) and in-hospital transfusion minimization care plan cannot include cell saver | — |
| Q30. Is the red cell antibody screen positive? | If yes, then provide type of antibody. If no, then go to Q31. | Y (anti-D): need to call hospital blood bank and alert them about need for antigen negative units on hand | N | N |

TABLE 3-continued

| Question (Q) | Response | Patient 1 | Patient 2 | Patient 3 |
|---|---|---|---|---|
| Q31. Is the subject anemic and was anemia treated? | If yes, provide with what type of medication, number of treatments, and results of treatment (e.g., hemoglobin levels). | Y (Fe only, three treatments, hemoglobin = 14 g/dL) | Y (Fe and EPO, three treatments, hemoglobin = 12.9 g/dL) | — |
| Q32. Is this the first time that the subject has been assessed? | If yes, then go to Q34. If no, then go to Q33. | N | N | N |
| Q33. Was the surgery rescheduled or cancelled? | If yes, then provide surgery date to be used to determine level of transfusion risk in Q34. If no, then go to Q34. | N | N | N |
| Q34. Has updated laboratory test results been received? | If yes, then reiterate Q1-Q19 with new data to determine an updated level of transfusion risk (sum). If no, then reiterate Q1-Q19 with available data to determine an updated level of transfusion risk (sum). | Y: patient no longer anemic New sum = 3 | Y: hemoglobin = 12.9 g/dL New sum = 4 | N New sum = 0 |
| Q35. Is there a difference between the previous and updated level of transfusion risk? | If yes, then describe and show in what area the points changed. If no, then STOP.  Resulting Patient Care Plan (BHP and TM care plans) | Y: score decrease by 2 points as anemia is no longer present  Patient 1: BHP = Treatment of anemia, smoking cessation information, alert blood bank regarding need for antigen negative units, multivitamins recommended TM = includes cell saver | Y: score decrease by 1 point as severity of anemia has decreased  Patient 2: BHP = Treatment of anemia, needs an anticoagulant call one week prior to surgery to discontinue anticoagulant medications with doctor's permission, multivitamins recommended TM = use of pediatric tubes for blood draws (can't include use of cell saver due to MRSA infection) | N  Patient 3: BHP = Patient must take multivitamin TM = none |

OTHER EMBODIMENTS

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of providing treatment for a subject, said method comprising:
   a) receiving a profile of said subject said profile comprising a level of hemoglobin of said subject and information regarding current or past history of disease of said subject; and
   b) utilizing said level of hemoglobin to determine a level of anemia; and
   c) utilizing said level of hemoglobin to determine a level of transfusion risk; in said physical computing device; and
   d) utilizing said information regarding current or past history of disease of said subject to determine a level of comorbidity; and
   e) utilizing said level of anemia, said level of transfusion risk, and said level of comorbidity to create a preoperative patient care plan, wherein said preoperative patient care plan comprises one or more directives selected from the following: administration of oral iron, intravenous iron, an erythropoietic medication, ferric carboxymaltose, iron sucrose, ascorbic acid, folate, vitamin B12, tranexamic acid, or desmopressin acetate; preoperative dialysis, preoperative coagulation therapy, or preoperative autologous blood donation; wherein said directives are to initiate treatment of said subject at least one week prior to a non-emergent surgery, wherein said preoperative patient care plan is included in a patient care plan; and wherein said subject is treated in accordance with at least one of said directives of said preoperative patient care plan and wherein said patient care plan is configured to reduce a risk associated with the non-emergent surgery.

2. The method of claim 1, wherein said method further comprises receiving a type of non-emergent surgery information and red cell antibody information, wherein said method comprises:

f) utilizing said type of said non-emergent surgery information to determine a range of anticipated loss of blood volume;

g) utilizing said range of anticipated loss of blood volume and said level of comorbidity to determine a range of tolerable loss of blood volume;

h) utilizing said red cell antibody information to determine one or more compatible blood types; and i) utilizing said range of anticipated loss of blood volume, said range of tolerable loss of blood volume, and said one or more compatible blood types to create directives for an in-hospital blood management or transfusion minimization care plan, wherein said in-hospital blood management or transfusion minimization care plan is included in said patient care plan.

3. The method of claim 1, wherein said non-emergent surgery is an orthopedic surgery, a cardiovascular surgery, a genitourinary surgery, a gastrointestinal surgery, other vascular surgery, a gynecology surgery, a neurosurgery, an oncologic thoracic surgery, a high-risk caesarian delivery, or any combination thereof.

4. The method of claim 3, wherein said non-emergent surgery is said orthopedic surgery selected from the group consisting of primary or revision total knee replacement surgery that is single or bilateral, primary or revision partial knee replacement surgery that is single or bilateral, primary or revision total hip joint arthroplasty, and spine surgery; said non-emergent surgery is said cardiovascular surgery selected from the group consisting of cardiac valve replacement, cardiac valve repair, coronary artery bypass surgery, coronary artery bypass surgery with cardiac valve repair or replacement, and aortic replacement surgery; said non-emergent surgery is said genitourinary surgery selected from the group consisting of radical retropubic prostatectomy and cystectomy; said non-emergent surgery is said gastrointestinal surgery, and said gastrointestinal surgery treats a cancer or an inflammatory bowel disease; said non-emergent surgery is said vascular surgery for aneurysm repair; said non-emergent surgery is said gynecology surgery selected from the group consisting of hysterectomy with or without bilateral salpingo-oophorectomy, tumor debulking, omentectomy, and lymph node sampling; said non-emergent surgery is said neurosurgery selected from the group consisting of meningioma resection and surgery to correct vascular malformation; or said non-emergent surgery is said oncologic thoracic surgery for removal of a lung tumor.

5. The method of claim 1, wherein said patient care plan comprises a directive for use of a transfusion product having a shelf age of less than 14 days.

6. The method of claim 1, wherein said level of transfusion risk of said subject is determined to be low, intermediate, high, or very high.

7. The method of claim 1, wherein said preoperative patient care plan comprises one or more directives selected from the following: administration of epoetin, epoetin alfa, darbepoetin alfa, epoetin delta, PDpoetin, or methoxy polyethylene glycol-epoetin beta.

8. The method of claim 1, further comprising repeating steps (a)-(d) to provide a revised patient care plan prior to said non-emergent surgery.

9. The method of claim 8, wherein said revised profile further comprises revised weight, gender, revised age, revised date of non-emergent surgery, revised information regarding whether or not said non-emergent surgery is a repeat procedure, and/or revised information regarding whether or not said non-emergent surgery is a non-isolated procedure.

10. The method of claim 2, wherein said in-hospital blood management or said transfusion minimization comprises the directive that if said one or more comorbid conditions are present, then said in-hospital blood management or transfusion minimization care plan comprises providing said patient with a transfusion product that has a shelf age of less than 14 days.

11. The method of claim 1, wherein said method, following step e), comprises: utilizing information regarding said subject after undergoing said non-emergent surgery, wherein said information regarding said subject after undergoing said non-emergent surgery comprises information regarding loss of blood volume during said non-emergent surgery, information regarding whether said subject had a transfusion during said non-emergent surgery, and information regarding adverse events; and utilizing said information regarding said subject after undergoing said non-emergent surgery, said profile, said level of transfusion risk, said level of comorbidity, said preoperative patient care plan, and said in-hospital transfusion minimization care plan to create a patient outcome report.

12. The method of claim 2, wherein said method further comprises utilizing said level of hemoglobin to determine a level of bleeding risk.

13. The method of claim 12, wherein said level of bleeding risk is determined to be high if said subject is taking one or more procoagulant medications.

14. The method of claim 13, wherein if said level of bleeding risk is high, said one or more directives comprises obtaining information from one or more laboratory tests selected from the group consisting of a screening coagulation panel and a special coagulation test.

15. The method of claim 12, wherein if said subject is anemic then said one or more directives comprises obtaining a determination of one or more laboratory tests selected from the group consisting of an iron assessment panel, a complete blood count, a reticulocyte count, a hemoglobin test, a vitamin B12 test, a folate test, and a C reactive protein assay.

16. The method of claim 12, wherein said one or more directives comprises obtaining information from a second test panel, wherein said second test panel comprises: one or more laboratory tests selected from the group consisting of a red cell antibody identification test, a direct antiglobulin test, an indirect antiglobulin test, and a blood typing test.

17. The method of claim 16, wherein if the one or more red cell antibodies are present, then said patient care plan comprises providing a directive that blood components compatible with the one or more red cell antibodies are available for transfusion during said non-emergent surgery.

18. The method of claim 1, wherein said method further comprises: utilizing said information regarding current or past history of disease to determine a level of renal risk, wherein if said information regarding current or past history of disease comprises current or past history of renal disease or current or past history of diabetes, then said level of renal risk is high; and wherein if said level of renal risk is high, then one or more directives comprises utilizing a creatinine test with calculated glomerular filtration rate or a blood urea nitrogen test.

19. The method of claim 18, wherein if said level of creatinine is more than 2 mg/dL, then said patient care plan comprises dialysis.

20. The method of claim 1, further comprising outputting a patient satisfaction outcome report, a hospital satisfaction outcome report, an adverse event outcome report, or a surgical outcome-specific report comprising said preoperative patient care plan.

21. The method of claim 1, wherein said profile further comprises a level of blood health index of said subject, and wherein said level of blood health index is determined from one or more laboratory tests selected from the group consisting of a creatinine test, a glomerular filtration rate test, a vitamin B12 test, and a folate test.

22. The method of claim 21, wherein said level of blood health index comprises one or more of level of serum iron, level of % iron saturation, level of ferritin, level of C reactive protein, mean corpuscular volume, mean corpuscular hemoglobin, level of vitamin B12, or level of folate.

23. The method of claim 21, wherein said method further comprises: utilizing said profile and said level of blood health index to determine a level of renal risk, wherein if said level of renal risk is high, then said patient care plan for treating said high level of renal risk comprises one or more directives selected from the following: administration of oral iron, intravenous iron, ferric carboxymaltose, iron sucrose, iron dextran, erythropoietin, folate, vitamin B12, epoetin, epoetin alfa, darbepoetin alfa, epoetin delta, PDpoetin, or methoxy polyethylene glycol-epoetin beta.

24. The method of claim 1, wherein said profile comprises a level of creatinine of said subject, wherein said method comprises applying said level of creatinine to determine said level of transfusion risk.

25. The method of claim 24, wherein said profile comprises a level of creatinine if said patient has been determined to have low hemoglobin.

26. The method of claim 1, wherein said method comprises comparing said level of hemoglobin to a predetermined value of hemoglobin indicative of anemia.

27. The method of claim 26, wherein said patient is determined to have anemia.

28. The method of claim 27, wherein said patient is determined to have chronic anemia.

29. The method of claim 27, wherein if said anemia is profound, then said directives comprise consideration to cancel surgery.

30. The method of claim 1, wherein said method comprises applying surgical demographics and clinical information to identify risks which may be mitigated prior to surgery.

31. The method of claim 1, wherein the subject has a chronic disease selected from the group consisting of a chronic heart failure, an inflammatory gastrointestinal disease, a rheumatologic inflammatory disease, a chronic viral disease, a chronic inflammatory state, a gynecological state, and a post-surgical state; wherein said chronic inflammatory state is selected from the group consisting of diabetes, chronic renal disease, and obesity; wherein said chronic viral disease is selected from the group consisting of hepatitis C infection, hepatitis B infection, and HIV infection; and wherein said gynecological state is pregnancy.

32. The method of claim 1, wherein the patient care plan is communicated to the subject, a surgeon, and/or a hospital.

33. The method of claim 1, wherein said patient care plan comprises a surgical patient care plan comprising one or more directives selected from the group consisting of use of a cell saver, acute normovolemic hemodilution (ANH), administration of tranexamic acid (TXA), and cautious use of hemodilution for patients.

34. The method of claim 2, wherein said patient care plan comprises a surgical patient care plan comprising one or more directives selected from the group consisting of use of a cell saver, acute normovolemic hemodilution (ANH), administration of tranexamic acid (TXA), and cautious use of hemodilution for patients.

35. The method of claim 1, wherein said patient care plan comprises an in-hospital and post-surgical patient care plan comprising one or more directives selected from the group consisting of TXA, pediatric blood tubes, minimization of lab draws, administration of oral iron, administration of intravenous iron, and administration of erythropoietin-stimulating agents.

36. The method of claim 2, wherein said patient care plan comprises an in-hospital and post-surgical patient care plan comprising one or more directives selected from the group consisting of administration of TXA, pediatric blood tubes, minimization of lab draws, administration of oral iron, administration of intravenous iron, and administration of erythropoietin-stimulating agents.

37. The method of claim 34, wherein said patient care plan comprises an in-hospital and post-surgical patient care plan comprising one or more directives selected from the group consisting of administration of TXA, pediatric blood tubes, minimization of lab draws, administration of oral iron, administration of intravenous iron, and administration of erythropoietin-stimulating agents.

38. The method of claim 1, wherein said patient care plan comprises a post-discharge patient care plan comprising one or more postoperative directives selected from the group consisting of administration of oral iron, administration of intravenous iron, and administration of erythropoietin-stimulating agents.

39. The method of claim 2, wherein said patient care plan comprises a post-discharge patient care plan comprising one or more postoperative directives selected from the group consisting of administration of oral iron, administration of intravenous iron, and administration of erythropoietin-stimulating agents.

40. The method of claim 34, wherein said patient care plan comprises a post-discharge patient care plan comprising one or more postoperative directives selected from the group consisting of administration of oral iron, administration of intravenous iron, and administration of erythropoietin-stimulating agents.

41. The method of claim 36, wherein said patient care plan comprises a post-discharge patient care plan comprising one or more postoperative directives selected from the group consisting of administration of oral iron, administration of intravenous iron, and administration of erythropoietin-stimulating agents.

42. The method of claim 1, wherein said patient care plan comprises administration of erythropoietin.

43. The method of claim 1, wherein said information regarding current or past history of disease comprises past history of cardiovascular disease, cerebrovascular disease, pulmonary disease, renal disease, cancer, autoimmune disease, gastrointestinal disease, pregnancy, bleeding disorder, inflammatory disease, active infection, blood clotting disorder, or use of over the counter or prescribed medications.

44. The method of claim 1, wherein said patient care plan comprises two, three, four, five, six, seven, eight, nine, ten, or more of said directives.

45. The method of claim 1, wherein said risk is selected from the group consisting of a transfusion risk, a comorbidity risk, and a surgical risk.

46. A method of preparing a subject for a non-emergent surgery, said method comprising:
   a) obtaining a determination of a level of anemia and a level of transfusion risk of said subject, each of which has been determined using a level of hemoglobin of said subject; and
   b) obtaining a determination of a level of comorbidity of said subject, which has been determined using information regarding current or past history of disease of said subject; and
   c) obtaining a preoperative patient care plan for said subject comprising one or more directives selected from the following: administration of oral iron, intravenous iron, an erythropoietic medication, ferric carboxymaltose, iron sucrose, ascorbic acid, folate, vitamin B12, tranexamic acid, or desmopressin acetate; preoperative dialysis, preoperative coagulation therapy, or preoperative autologous blood donation; which has been created using said level of anemia, said level of transfusion risk, and said level of comorbidity, wherein said preoperative patient care plan is included in a patient care plan; and
   d) following step (c), treating said subject in accordance with at least one of said directives of said preoperative patient care plan at least one week prior to said non-emergent surgery,
   wherein a risk associated with the non-emergent surgery is reduced.

47. The method of claim 46, wherein said patient care plan comprises an in-hospital blood management or transfusion minimization care plan comprising:
   (a1) obtaining a determination of a range of anticipated loss of blood volume for said subject, which was determined using a type of non-emergent surgery information of said subject; or
   (a2) obtaining a determination of a range of tolerable loss of blood volume for said subject, which was determined using said range of anticipated loss of blood volume and a level of comorbidity.

48. The method of claim 46, further comprising performing said non-emergent surgery on said subject, wherein said non-emergent surgery is an orthopedic surgery, a cardiovascular surgery, a genitourinary surgery, a gastrointestinal surgery, other vascular surgery, a gynecology surgery, a neurosurgery, an oncologic thoracic surgery, a high-risk caesarian delivery, or any combination thereof.

49. The method of claim 48, wherein said non-emergent surgery is said orthopedic surgery selected from the group consisting of primary or revision total knee replacement surgery that is single or bilateral, primary or revision partial knee replacement surgery that is single or bilateral, primary or revision total hip joint arthroplasty, and spine surgery; said non-emergent surgery is said cardiovascular surgery selected from the group consisting of cardiac valve replacement, cardiac valve repair, coronary artery bypass surgery, coronary artery bypass surgery with cardiac valve repair or replacement, and aortic replacement surgery; said non-emergent surgery is said genitourinary surgery selected from the group consisting of radical retropubic prostatectomy and cystectomy; said non-emergent surgery is said gastrointestinal surgery, and said gastrointestinal surgery treats a cancer or an inflammatory bowel disease; said non-emergent surgery is said vascular surgery for aneurysm repair; said non-emergent surgery is said gynecology surgery selected from the group consisting of hysterectomy with or without bilateral salpingo-oophorectomy, tumor debulking, omentectomy, and lymph node sampling; said non-emergent surgery is said neurosurgery selected from the group consisting of meningioma resection and surgery to correct vascular malformation; or said non-emergent surgery is said oncologic thoracic surgery for removal of a lung tumor.

50. The method of claim 46, wherein step (a) further comprises obtaining a determination of a level of transfusion risk of said subject, wherein said level of transfusion risk is low, intermediate, high, or very high.

51. The method of claim 50, wherein step (c) further comprises, as part of the patient care plan, the following: if said level of transfusion risk is low or intermediate and said one or more comorbid conditions are not present, then said preoperative patient care plan comprises one or more of administration of oral iron, ascorbic acid, or a multivitamin.

52. The method of claim 50, wherein step (c) further comprises, as part of the patient care plan, the following: if said one or more comorbid conditions are present, then said preoperative patient care plan comprises one or more of administration of an erythropoietic medication, intravenous iron, oral iron, tranexamic acid, or desmopressin acetate; preoperative dialysis, preoperative coagulation therapy, or preoperative autologous blood donation.

53. The method of claim 50, wherein step (c) further comprises, as part of the patient care plan, the following: if said level of transfusion risk is high or very high, then said patient care plan comprises administration of intravenous iron, erythropoietic stimulating factor, or tranexamic acid; use of a cell saver, preoperative autologous blood donation, postoperative iron, or use of pediatric blood tubes for blood draws.

54. The method of claim 46, wherein step (c) further comprises, as part of the one or more directives and prior to step (e), administration of oral iron, intravenous iron, ferric carboxymaltose, iron sucrose, iron dextran, ascorbic acid, erythropoietin, folate, vitamin B12, epoetin, epoetin alfa, darbepoetin alfa, epoetin delta, PDpoetin, or methoxy polyethylene glycol-epoetin beta.

55. The method of claim 46, further comprising repeating steps (a) and (b) to provide a revised patient care plan prior to step (e).

56. The method of claim 55, wherein said revised patient care plan has been created using a revised weight, gender, revised age, revised date of non-emergent surgery, revised level of creatinine, revised information regarding whether or not said non-emergent surgery is a repeat procedure, and/or revised information regarding whether or not said non-emergent surgery is a non-isolated procedure.

57. The method of claim 47, wherein said in-hospital blood management or said transfusion minimization care plan comprises the directive that if said one or more comorbid conditions are present, then said in-hospital blood management or transfusion minimization care plan comprises providing said patient with a transfusion product having a shelf age of less than 14 days.

58. The method of claim 47, wherein said method further comprises obtaining a patient outcome report, which was produced using information regarding said subject after undergoing said non-emergent surgery, said level of transfusion risk, said level of comorbidity, said preoperative patient care plan, and said in-hospital blood management or transfusion minimization care plan, and wherein said information regarding said subject after undergoing said non-emergent surgery comprises information regarding loss of blood volume during said non-emergent surgery, information regarding whether said subject had a transfusion during said non-emergent surgery, and information regarding adverse events.

59. The method of claim 58, wherein said method further comprises obtaining a determination of a bleeding risk, wherein said bleeding risk was determined using said level of hemoglobin and said level of transfusion risk.

60. The method of claim 59, wherein said level of bleeding risk is high if said subject is taking one or more procoagulant medications.

61. The method of claim 60, wherein if said determination of level of bleeding risk is high, said one or more directives comprises obtaining information from one or more laboratory tests selected from the group consisting of a screening coagulation panel and a special coagulation test.

62. The method of claim 61, wherein if said subject is anemic, then said one or more directives comprises obtaining a determination of one or more laboratory tests from the group consisting of an iron assessment panel, a complete blood count, a hemoglobin test, a vitamin B12 test, a folate test, and a C reactive protein assay.

63. The method of claim 47, wherein said patient care plan further comprises a directive for obtaining a determination of results of a second test panel, wherein said second test panel comprises obtaining a determination of one or more laboratory tests selected from the group consisting of a red cell antibody identification test, a direct antiglobulin test, an indirect antiglobulin test, and a blood typing test.

64. The method of claim 63, wherein if one or more of the red cell antibodies are present, said patient care plan comprises, as part of the one or more directives, that blood components compatible with the one or more red cell antibodies should be available for transfusion during said non-emergent surgery.

65. The method of claim 46, wherein said patient care plan comprises a directive for a determination of a level of renal risk based upon information regarding current or past history of disease in the subject, wherein if said information regarding current or past history of disease comprises current or past history of renal disease or current or past history of diabetes, then said level of renal risk is high, wherein if said level of renal risk is high, said method comprises obtaining a result of a creatinine test with calculated glomerular filtration rate or a blood urea nitrogen test.

66. The method of claim 65, wherein if said level of creatinine is more than 2 mg/dL, then said patient care plan comprises a directive for dialysis.

67. The method of claim 46, further comprising obtaining a patient satisfaction outcome report, a hospital satisfaction outcome report, an adverse event outcome report, or a surgical outcome-specific report comprising said preoperative patient care plan or said revised patient care plan.

68. The method of claim 46, wherein said patient care plan comprises a directive for obtaining a determination of a level of blood health index of said subject, which was determined from one or more laboratory tests selected from the group consisting of a creatinine test, a glomerular filtration rate test, a vitamin B12 test, and a folate test.

69. The method of claim 68, wherein said patient care plan comprises a directive for obtaining one or more of a level of serum iron, level of % of iron saturation, level of ferritin, level of C reactive protein, mean corpuscular volume, mean corpuscular hemoglobin, level of vitamin B12, or level of folate.

70. The method of claim 69, wherein if said renal risk is high said patient care plan comprises a directive for administration of oral iron, intravenous iron, ferric carboxymaltose, iron sucrose, iron dextran, erythropoietin, folate, vitamin B12, epoetin, epoetin alfa, darbepoetin alfa, epoetin delta, PDpoetin, or methoxy polyethylene glycol-epoetin beta.

71. The method of claim 46, wherein said patient care plan comprises a directive for obtaining a determination of a level of transfusion risk determined using a level of creatinine of said subject.

72. The method of claim 71, wherein said level of creatinine was determined in a patient with a low level of hemoglobin.

73. The method of claim 71, wherein said level of hemoglobin was determined using a predetermined value of hemoglobin indicative of anemia.

74. The method of claim 71, wherein said patient was determined to have anemia.

75. The method of claim 74, wherein said patient was determined to have chronic anemia.

76. The method of claim 74, wherein if said anemia was determined to be profound, then said patient care plan comprises a directive for consideration to cancel surgery.

77. The method of claim 46, wherein said patient care plan comprises a directive for obtaining a determination of surgical demographics and clinical information to identify risks which may be mitigated prior to surgery.

78. The method of claim 46, wherein the subject has a chronic disease selected from the group consisting of a chronic heart failure, an inflammatory gastrointestinal disease, a rheumatologic inflammatory disease, a chronic viral disease, a chronic inflammatory state, a gynecological state, and a post-surgical state; wherein said chronic inflammatory state is selected from the group consisting of diabetes, chronic renal disease, and obesity; wherein said chronic viral disease is selected from the group consisting of hepatitis C infection, hepatitis B infection, and HIV infection; and wherein said gynecological state is pregnancy.

79. The method of claim 46, wherein the patient care plan is communicated to the subject, a surgeon, and/or a hospital.

80. The method of claim 46, wherein said patient care plan comprises directives for treating said subject during surgery selected from (i) use of a cell saver, (ii) acute normovolemic hemodilution (ANH), (iii) administration of tranexamic acid (TXA), and (iv) cautious use of hemodilution for patients that are small.

81. The method of claim 47, wherein said patient care plan comprises directives for treating said subject during surgery selected from (i) use of a cell saver, (ii) acute normovolemic hemodilution (ANH), (iii) administration of tranexamic acid (TXA), and (iv) cautious use of hemodilution for patients that are small.

82. The method of claim 46, wherein said patient care plan comprises directives for treating said subject said subject following surgery and prior to discharge from a hospital selected from (i) administration of TXA, (ii) minimization of lab draws, (iii) administration of oral iron, (iv) administration of intravenous iron, (v) administration of erythropoietin-stimulating agents, and (vi) use of pediatric blood tubes.

83. The method of claim 47, wherein said patient care plan comprises directives for treating said subject said subject following surgery and prior to discharge from a hospital selected from (i) administration of TXA, (ii) minimization of lab draws, (iii) administration of oral iron, (iv) administration of intravenous iron, (v) administration of erythropoietin-stimulating agents, and (vi) use of pediatric blood tubes.

84. The method of claim 81, wherein said patient care plan comprises directives for treating said subject said subject following surgery and prior to discharge from a hospital selected from (i) administration of TXA, (ii) minimization of lab draws, (iii) administration of oral iron, (iv) administration of intravenous iron, (v) administration of erythropoietin-stimulating agents, and (vi) use of pediatric blood tubes.

85. The method of claim 46, wherein said patient care plan comprises one or more postoperative directives selected from (i) administration of oral iron, (ii) administration of intravenous iron, and (iii) administration of erythropoietin-stimulating agents, wherein said directives are for treating said subject following discharge from a hospital.

86. The method of claim 47, wherein said patient care plan comprises one or more postoperative directives selected from (i) administration of oral iron, (ii) administration of intravenous iron, and (iii) administration of erythropoietin-stimulating agents, wherein said directives are for treating said subject following discharge from a hospital.

87. The method of claim 81, wherein said patient care plan comprises one or more postoperative directives selected from (i) administration of oral iron, (ii) administration of administration of intravenous iron, and (iii) administration of erythropoietin-stimulating agents, wherein said directives are for treating said subject following discharge from a hospital.

88. The method of claim 83, wherein said patient care plan comprises one or more postoperative directives selected from (i) administration of oral iron, (ii) administration of intravenous iron, and (iii) administration of erythropoietin-stimulating agents, wherein said directives are for treating said subject following discharge from a hospital.

89. The method of claim 46, wherein said patient care plan comprises a directive for administering erythropoietin.

90. The method of claim 46, wherein said information regarding current or past history of disease comprises past history of cardiovascular disease, cerebrovascular disease, pulmonary disease, renal disease, cancer, autoimmune disease, gastrointestinal disease, pregnancy, bleeding disorder, inflammatory disease, active infection, blood clotting disorder, or use of over the counter or prescribed medications.

91. The method of claim 46, wherein said patient care plan comprises two, three, four, five, six, seven, eight, nine, ten, or more of said directives.

\* \* \* \* \*